(12) United States Patent
Hayter, II

(10) Patent No.: US 9,715,576 B2
(45) Date of Patent: Jul. 25, 2017

(54) METHOD FOR SEARCHING A TEXT (OR ALPHANUMERIC STRING) DATABASE, RESTRUCTURING AND PARSING TEXT DATA (OR ALPHANUMERIC STRING), CREATION/APPLICATION OF A NATURAL LANGUAGE PROCESSING ENGINE, AND THE CREATION/APPLICATION OF AN AUTOMATED ANALYZER FOR THE CREATION OF MEDICAL REPORTS

(71) Applicant: Robert G. Hayter, II, Glenn Allen, VA (US)

(72) Inventor: Robert G. Hayter, II, Glenn Allen, VA (US)

(*) Notice: Subject to any disclaimer, the term of this patent is extended or adjusted under 35 U.S.C. 154(b) by 518 days.

(21) Appl. No.: 14/214,753

(22) Filed: Mar. 15, 2014

(65) Prior Publication Data
US 2015/0025909 A1    Jan. 22, 2015

Related U.S. Application Data

(60) Provisional application No. 61/790,817, filed on Mar. 15, 2013.

(51) Int. Cl.
| | | |
|---|---|---|
| *G06F 17/28* | (2006.01) | |
| *G06F 17/27* | (2006.01) | |
| *G06F 17/21* | (2006.01) | |
| *G06F 19/00* | (2011.01) | |

(52) U.S. Cl.
CPC .......... *G06F 19/321* (2013.01); *G06F 19/328* (2013.01); *G06F 19/345* (2013.01); *G06F 19/3443* (2013.01)

(58) Field of Classification Search
CPC ............... G06F 17/2785; G06F 17/289; G06F 17/2735; G06F 17/2775; G06F 17/2705; G06F 17/2241; G06F 17/2755; G06F 17/21; G06F 17/30616; G06F 17/30864
USPC ....................................................... 704/1–10
See application file for complete search history.

(56) References Cited

U.S. PATENT DOCUMENTS

| | | |
|---|---|---|
| 5,642,502 A | 6/1997 | Driscoll |
| 6,625,599 B1 | 9/2003 | Bera |
| 7,024,351 B2 | 4/2006 | Wang |
| 7,231,383 B2 | 6/2007 | Andreev et al. |

(Continued)

FOREIGN PATENT DOCUMENTS

WO    WO/2010/045463    4/2010

OTHER PUBLICATIONS

Samuel Kuttner, "Development of a spreadsheet and a database for recording, reporting and archiving data from quality assurance tests of radiological equipment", Department of Radiology UNN, Tromso, Norway 2012, retrieved from: http://www.medfys.no/nfmf-documents/Opplastet/downloads/2012/07/Samuel_Kuttner_Medfys_2012_QA_Database_1_Final.pdf.*

(Continued)

*Primary Examiner* — Edgar Guerra-Erazo
(74) *Attorney, Agent, or Firm* — John J. Skinner, Jr.

(57) ABSTRACT

A sequential series of methods for optimized searching within a text (or alphanumeric string) database to retrieve specific and relevant results, followed by optimized restructuring and parsing of text data (or alphanumeric string), followed by creation/application of a natural language processing engine, followed by the creation/application of an automated analyzer is presented.

14 Claims, 51 Drawing Sheets

(56) References Cited

U.S. PATENT DOCUMENTS

| | | | |
|---|---|---|---|
| 7,251,776 B2* | 7/2007 | Handsaker | G06F 17/246 |
| | | | 715/212 |
| 7,321,861 B1* | 1/2008 | Oon | G06F 19/322 |
| | | | 704/9 |
| 7,523,098 B2 | 4/2009 | Hirsch et al. | |
| 7,542,996 B2 | 6/2009 | Fanning et al. | |
| 7,574,347 B2 | 8/2009 | Wang | |
| 8,073,840 B2 | 12/2011 | Smith et al. | |
| 8,180,783 B1 | 5/2012 | Fletcher et al. | |
| 8,190,556 B2 | 5/2012 | Pappas | |
| 8,275,755 B2 | 9/2012 | Hirsch et al. | |
| 8,375,021 B2 | 2/2013 | Sokolan et al. | |
| 8,407,165 B2 | 3/2013 | Monroe et al. | |
| 8,782,088 B2* | 7/2014 | Carus | G06F 19/3487 |
| | | | 707/608 |
| 8,799,013 B2* | 8/2014 | Gustafson | A61B 5/4312 |
| | | | 382/128 |
| 9,152,763 B2* | 10/2015 | Carus | G06F 19/3487 |
| 9,286,061 B2* | 3/2016 | Zhang | G06F 8/73 |
| 2004/0024756 A1 | 2/2004 | Rickard | |
| 2005/0050030 A1* | 3/2005 | Gudbjartsson | G06F 17/30595 |
| 2005/0228815 A1* | 10/2005 | Carus | G06F 19/3487 |
| 2006/0143157 A1 | 6/2006 | Landsman | |
| 2006/0224579 A1 | 10/2006 | Zheng | |
| 2007/0214017 A1* | 9/2007 | Profio | A61B 6/465 |
| | | | 705/3 |
| 2008/0059486 A1 | 3/2008 | Pappas | |
| 2009/0248442 A1 | 10/2009 | Pacheco et al. | |
| 2011/0137132 A1* | 6/2011 | Gustafson | A61B 5/4312 |
| | | | 600/300 |
| 2011/0179074 A1 | 7/2011 | Lee et al. | |
| 2011/0289035 A1 | 11/2011 | Stojadinovic et al. | |
| 2011/0289036 A1 | 11/2011 | Stojadinovic et al. | |
| 2011/0295782 A1 | 12/2011 | Stojadinovic et al. | |
| 2011/0301977 A1 | 12/2011 | Belcher et al. | |
| 2012/0130730 A1 | 5/2012 | Setlur et al. | |
| 2012/0212337 A1 | 8/2012 | Montyne et al. | |
| 2012/0215782 A1 | 8/2012 | Jagannathan et al. | |
| 2012/0245926 A1 | 9/2012 | Montyne et al. | |
| 2012/0245961 A1 | 9/2012 | Yegnanarayanan | |

OTHER PUBLICATIONS

Dang, P. A., Kalra, M. K., Blake, M. A., Schultz, T. J., Halpern, E. F., & Dreyer, K. J. (2008). Extraction of recommendation features in radiology with natural language processing: exploratory study. American Journal of Roentgenology, 191(2), 313-320.*

Hayter, R. G., Rhea, J. T., Small, A., Tafazoli, F. S., & Novelline, R. A. (2006). Suspected Aortic Dissection and Other Aortic Disorders: Multi-Detector Row CT in 373 Cases in the Emergency Setting 1. Radiology, 238(3), 841-852.*

Montage Healthcare Solutions, Inc., "Growing Your Radiology Practice: The Role of Search-Driven Analytics", 2013, www.montagehealthcare.com.

* cited by examiner

~290

| | A | B | C | D | E | F | G | H | I | J |
|---|---|---|---|---|---|---|---|---|---|---|
| 1 | NAME | ID | Date of service | Date of birth | Age | SEX | Status | Accession number | EXAM Type | EXAM Description |
| 2 | XXXX | XXXX | XXXX | XXXX | XXXX | XXXX | XXXX | XXXX | XXXX | XXXX |
| 3 | | | | | | | | | | |
| 4 | | | | | | | | | | |
| 5 | | | | | | | | | | |

| | K | L | M | N | O | P | Q |
|---|---|---|---|---|---|---|---|
| | Ordering Physician | Radiologist #1 | Radiologist #2 | Radiologist #3 | CT REPORT -- HISTORY | CT REPORT -- TECHNIQUE |
| | XXXX | XXXX | XXXX | XXXX | XXXX | XXXX |

| | R | S | T | U |
|---|---|---|---|---|
| | CT REPORT -- FINDINGS | CT REPORT -- IMPRESSION | CT REPORT -- PROCESSED (processed 23 times for AAC3 NLP decoding) | |
| | XXXX | XXXX | XXXX | |

*dissection protocol*
*evaluation of aortic dissection*
*aorta were obtained per departmental protocol*
*Rule out aortic dissection*
*ASSESS FOR AORDIC, DISSECTION*
*evaluate the entire aorta*
*obtained from the aortic arch through the iliac*
*valuate for aortic dissection*
*DISECTION PROTO*
*images of the aorta*
*aortic dissection protocol*
*evaluate for aortic dissection*
*dissection CT*
*from the thoracic inlet to the iliac bifurcation*
*protocol for evaluation of aortic dissection*
*CT images from the aortic arch through the aortic bifurcation*
*AORTIC DISSECTION VASCULAR PROTOCOL*
*scans were obtained from the apex of the lungs to the femoral heads*
*arch of the aorta through the pubic symphysis*
*apex of the lungs to the femoral heads*
*domes of the diaphragm to the iliac*
*scan of the chest abdomen and pelvis*
*scan of the chest, abdomen pelvis*
*scans of both the chest, abdomen and pelvis*
*scans were obtained from the apex of the lungs to the femoral heads*
*aortic arch through the aortic bifurcation*
*performed for the evaluation of aortic dissection*
*CT of the chest abdomen and pelvis*
*scan of the chest abdomen and pelvis*
*protocol for evaluation of aortic dissection*
*to assess for aortic dissection*
*apex of the lungs to the femoral heads*
*to the specific evaluation of aortic dissection*
*CT OF THE CHEST, ABDOMEN AND PELVIS*
*protocol for evaluation of suspected thoracic aortic dissection*
*from the apex of the lungs to the femoral heads*
*for evaluation of aortic dissection*
*CT of the thorax, abdomen and pelvis*
*scans were obtained from the apex of the lungs to the femoral heads*
*scan of the chest abdomen pelvis*
*performed from the aortic arch to the iliac*
*performed throughout the thorax, abdomen and pelvis*
*to assess for dissection* dissection protocol (repeated for each line)

| Phrase | Code |
|---|---|
| "An aortic dissection" | POSAAD |
| "Extensive aortic dissection" | POSAAD |
| "Positive aortic dissection" | POSAAD |
| "Type III" | POSAAD |
| "Type II" | POSAAD |
| "Type I" | POSAAD |
| "suggestive of thrombosed dissection" | POSAAD |
| "CONSISTENT WITH AORTIC DISSECTION" | POSAAD |
| "Large aortic dissection" | POSAAD |
| "FOCAL DISSECTION" | POSAAD |
| "is evidence of a flap within the aorta" | POSAAD |
| "Dissection extending from proximal descending aorta to" | POSAAD |
| "Type 1 aortic dissection" | POSAAD |
| "Type 2 aortic dissection" | POSAAD |
| "Type 3 aortic dissection" | POSAAD |
| "Type A aortic dissection" | POSAAD |
| "Type B aortic dissection" | POSAAD |
| "Focal dissection" | POSAAD |
| "An intimal flap is noted" | POSAAD |
| "Type I aortic dissection" | POSAAD |
| "intimal flap is" | POSAAD |
| "Focal dissection of the infrarenal abdominal aorta" | POSAAD |
| "Focal dissection of the suprarenal abdominal aorta" | POSAAD |
| "Focal dissection of the thoracic aorta" | POSAAD |
| "Extensive aortic dissection" | POSAAD |
| "Small aortic dissection" | POSAAD |
| "Tiny aortic dissection" | POSAAD |
| "Positive intimal flap" | POSAAD |
| "Intimal flap consistent" | POSAAD |
| "Type 1 dissection" | POSAAD |
| "Type 2 dissection" | POSAAD |
| "Type 3 dissection" | POSAAD |
| "Type A dissection" | POSAAD |
| "Type B dissection" | POSAAD |
| "thrombosed aortic dissection" | POSAAD |
| "thoracic aortic dissection" | POSAAD |
| "abdominal aortic dissection" | POSAAD |
| "thoracic dissection" | POSAAD |
| "abdominal dissection" | POSAAD |
| "dissection of the aorta" | POSAAD |
| "type A dissection" | POSAAD |
| "intimal flap extending" | POSAAD |
| "an intimal flap" | POSAAD |
| "The aortic dissection" | POSAAD |
| "The dissection flap" | POSAAD |
| "TYPE A DISSECTION" | POSAAD |
| "large aortic dissection" | POSAAD |
| "intimal flap originating" | POSAAD |
| "TYPE 1 AORTIC DISSECTION" | POSAAD |
| "Type 1 thrombosed aortic dissection" | POSAAD |
| "is an intimal aortic flap" | POSAAD |
| "Ascending thoracic aortic dissection" | POSAAD |
| "type A aortic dissection" | POSAAD |
| "dissection of the aorta extending" | POSAAD |
| "represents intramural hematoma" | POSAAD |
| "Penetrating ulcer of the ascending aorta" | POSAAD |
| "ascending aorta there is evidence of ulceration" | POSAAD |
| "PLAQUE ULCERATION" | POSAAD |
| "outpouching of contrast" | POSAAD |

| Phrase | Label |
|---|---|
| "a dissection" | PCSAAD |
| "focal outpouching of contrast" | PCSAAD |
| "Type IIIb aortic dissection" | PCSAAD |
| "The dissection" | PCSAAD |
| "segment intimal flap" | PCSAAD |
| "is an aortic dissection" | PCSAAD |
| "Type B Dissection" | PCSAAD |
| "an aortic dissection" | PCSAAD |
| "is a dissection" | PCSAAD |
| "TYPE B DISSECTION" | PCSAAD |
| "type B aortic dissection" | PCSAAD |
| "a penetrating aortic ulcer" | PCSAAD |
| "an intimal flap" | PCSAAD |
| "consistent with focal dissection" | PCSAAD |
| "dissection of the infrarenal aorta" | PCSAAD |
| "intimal dissection flap" | PCSAAD |
| "is a intramural hematoma" | PCSAAD |
| "suggestive of intramural hematoma" | PCSAAD |
| "hemorrhage into the aortic wall" | PCSAAD |
| "HYPERDENSE CRESCENT SIGN" | PCSAAD |
| "represent an intramural hematoma" | PCSAAD |
| "crescentic region of increased attenuation" | PCSAAD |
| "false lumen from dissection" | PCSAAD |
| "increased crescentic attenuation" | PCSAAD |
| "thrombosed dissection" | PCSAAD |
| "aneurysm/pseudo aneurysm" | PCSAAD |
| "a focal intramural hematoma" | PCSAAD |
| "focal mural hematoma" | PCSAAD |
| "eccentric bulge" | PCSAAD |
| "intramural hemorrhage" | PCSAAD |
| "which suggests intramural hematoma" | PCSAAD |
| "is focal ectasia" | PCSAAD |
| "An anterior intramural hematoma" | PCSAAD |
| "an invagination of contrast" | PCSAAD |
| "extends along the wall of the aorta" | PCSAAD |
| "consistent with a aortic wall ulceration/aortic dissection" | PCSAAD |
| "FOCAL INVAGINATION" | PCSAAD |
| "CONSISTENT WITH AORTIC ULCERATION/DISSECTION" | PCSAAD |
| "represent an ulcerated plaque" | PCSAAD |
| "with intramural thrombus" | PCSAAD |
| "is a penetrating atherosclerotic ulcer" | PCSAAD |
| "consistent with acute intramural hematoma" | PCSAAD |
| "tiny aortic ulcer" | PCSAAD |
| "likely associated intramural hematoma" | PCSAAD |
| "crescentic of intramural high density" | PCSAAD |
| "consistent with an acute intramural hemorrhage" | PCSAAD |
| "are outpouchings of contrast" | PCSAAD |
| "consistent with penetrating ulcers" | PCSAAD |
| "intramural leak of contrast" | PCSAAD |
| "medial displacement of the calcified intima" | PCSAAD |
| "numerous ulcerations from the true aortic" | PCSAAD |
| "into intramural hematoma" | PCSAAD |
| "indicated penetrating aortic ulcer" | PCSAAD |
| "with focal intramural dissection" | PCSAAD |
| "multiple ulcerated plaques" | PCSAAD |
| "is focal penetration of a single ulcer of the aorta" | PCSAAD |
| "with associated intramural hemorrhage" | PCSAAD |
| "some penetrating aortic ulcers" | PCSAAD |
| "Aortic ulcers" | PCSAAD |

```
"strongly suggest ulcerative plaque"                                    POSAAD
"CONSISTENT WITH AORTIC ULCERATION"                                     POSAAD
"A focal penetration ulceration"                                        POSAAD
"FOCAL PENETRATING ULCERATION"                                          POSAAD
"a penetrating ulcer"                                                   POSAAD
"PENETRATING ULCER IS SEEN"                                             POSAAD
"penetrating aortic ulcer"                                              POSAAD
"penetrating atherosclerotic ulcers"                                    POSAAD
"suggesting ulceration"                                                 POSAAD
"linear extension of contrast"                                          POSAAD
"likely represents a focal ulceration"                                  POSAAD
"focal region suggestive of ulceration"                                 POSAAD
"penetrating atherosclerotic ulcers"                                    POSAAD
"with multiple penetrating atherosclerotic ulcers"                      POSAAD
"representing a focal ulcerated plaque"                                 POSAAD
"penetrating ulcer"                                                     POSAAD
"focal penetration of a single ulcer"                                   POSAAD
"focal ulcerated plaque"                                                POSAAD
"PLAQUE ULCERATION"                                                     POSAAD
"outpouching of contrast"                                               POSAAD
"?outpouching of contrast"                                              POSAAD
"saccular aneurysm"                                                     POSAAD
"ascending thoracic aortic aneurysm"                                    POSAAD
"ascending thoracic aorta aneurysm"                                     POSAAD
"descending thoracic aortic aneurysm"                                   POSAAD
"descending thoracic aorta aneurysm"                                    POSAAD
"abdominal aortic aneurysm"                                             POSAAD
"abdominal aorta aneurysm"                                              POSAAD
"ascending aortic aneurysm"                                             POSAAD
"descending aortic aneurysm"                                            POSAAD
"thoracoabdominal aortic aneurysm"                                      POSAAD
"aneurysmal dilation of ascending aorta"                                POSAAD
"aneurysmal dilatation of the infrarenal abdominal aorta"               POSAAD
"aneurysmal dilatation of the infrarenal aorta"                         POSAAD
"infrarenal abdominal aortic aneurysm"                                  POSAAD
"infrarenal aortic aneurysm"                                            POSAAD
"abdominal aortic aneurysm"                                             POSAAD
"aorta measures 5 cm at the root"                                       POSAAD
"is a abdominal aortic aneurysm"                                        POSAAD
"aneurysm of the abdominal aorta"                                       POSAAD
"ascending aortic aneurysm"                                             POSAAD
"abdominal aortic aneurysm"                                             POSAAD
"thoracic and abdominal aortic aneurysm"                                POSAAD
"suprarenal aortic aneurysm"                                            POSAAD
"aneurysm of the arch"                                                  POSAAD
"aneurysmal at the level of the main pulmonary artery"                  POSAAD
"Thoracoabdominal aortic aneurysm"                                      POSAAD
"aneurysm of the ascending aorta, arch and mid descending aorta"        POSAAD
"infrarenal abdominal aortic aneurysm"                                  POSAAD
"thoracoabdominal aneurysm"                                             POSAAD
"ectasia of the descending aorta"                                       POSAAD
"aneurysm of the suprarenal aorta"                                      POSAAD
"ANEURYSMAL DILATATION OF THE SUPRARENAL AORTA"                         POSAAD
"prominence of aortic root"                                             POSAAD
"infrarenal abdominal aortic aneurysm"                                  POSAAD
"proximal descending aorta are measures approximately 4"                POSAAD
"is an infrarenal fusiform abdominal aortic aneurysm"                   POSAAD
"aneurysmal dilatation of the thoracic aorta"                           POSAAD
"abdominal aortic aneurysm"                                             POSAAD
```

*infrarenal atherosclerotic aortic aneurysm* — POSAAD
*The AAA* — POSAAD
*infrarenal aneurysm* — POSAAD
*saccular aneurysm that originates just distal to the origin of the left subclavian artery* — POSAAD
*descending aorta measures 3* — POSAAD
*aortic hiatus, the aorta measures 4* — POSAAD
*level of the superior mesenteric artery, the aorta measures 3* — POSAAD
*At the level of the renal arteries, the aorta measures approximately 6* — POSAAD
*THORACIC ABDOMINAL AORTIC ANEURYSM* — POSAAD
*aortic hiatus, the aorta measures 4* — POSAAD
*THORACIC ABDOMINAL AORTIC ANEURYSM* — POSAAD
*aneurysm of the ascending thoracic aorta* — POSAAD
*DESCENDING THORACIC AORTIC ANEURYSM* — POSAAD
*infrarenal abdominal aortic aneurysm* — POSAAD
*ascending aorta is ectatic* — POSAAD
*infrarenal AAA* — POSAAD
*ascending thoracic aorta is aneurysmal* — POSAAD
*Aneurysmal ascending thoracic aorta* — POSAAD
*infrarenal fusiform aortic aneurysm* — POSAAD
*ascending aorta measures 4* — POSAAD
*abdominal aorta is aneurysmal* — POSAAD
*SACCULAR ANEURYSM OFF THE LEFT POSTEROLATERAL ASPECT OF THE AORTIC ROOT* — POSAAD
*below the renal arteries there is aneurysmal dilatation* — POSAAD
*aneurysmal dilatation of the infrarenal aorta* — POSAAD
*infrarenal aortic aneurysm* — POSAAD
*infrarenal abdominal aortic aneurysm* — POSAAD
*is a descending thoracic aortic aneurysm* — POSAAD
*Small abdominal aortic aneurysm* — POSAAD
*pararenal aortic aneurysm* — POSAAD
*aorta from the level of the IMA take off to the aortic graft is dilated* — POSAAD
*aorta from the level of the celiac axis take off to the aortic graft is dilated* — POSAAD
*aorta from the level of the SMA take off to the aortic graft is dilated* — POSAAD
*aneurysm of the descending thoracic aorta* — POSAAD
*juxtarenal abdominal aortic aneurysm* — POSAAD
*transverse aortic arch is a saccular aneurysm* — POSAAD
*saccular aneurysm arising from the aortic arch* — POSAAD
*infrarenal abdominal aortic aneurysm* — POSAAD
*ectasia of the thoracic aorta distal to take off of the left subclavian* — POSAAD
*infrarenal abdominal aortic aneurysm* — POSAAD
*descending thoracic aorta aneurysm* — POSAAD
*infrarenal abdominal aneurysm* — POSAAD
*descending thoracic aortic aneurysm* — POSAAD
*infrarenal abdominal aortic aneurysm* — POSAAD
*descending thoracic aorta becomes aneurysmal* — POSAAD
*hiatus the aorta measures 4* — POSAAD
*ectasia of the proximal infrarenal aorta* — POSAAD
*Soft tissue attenuation pericardial collection* — POSAAD
*may represent hemopericardium* — POSAAD
*small hemopericardium* — POSAAD
*Hemopericardium consistent* — POSAAD
*moderate pericardial fluid collection* — POSAAD
*consistent with hemopericardium* — POSAAD
*moderate hemomediastinum* — POSAAD
*suggesting acute leak* — POSAAD
*represents mediastinal hematoma* — POSAAD
*perforation of the ascending aortic aneurysm* — POSAAD
*High-density pericardial effusion* — POSAAD
*high attenuation pericardial fluid* — POSAAD
*element of hemorrhage* — POSAAD

| Phrase | Type |
|---|---|
| *ascending arch to the aortic bifurcation* | TYPE A |
| *ascending arch into* | TYPE A |
| *ascending arch into the right external* | TYPE A |
| * from proximal descending aorta to* | TYPE A |
| *proximal to the takeoff of the left subclavian artery and extend* | TYPE A |
| *aortic arch and extending inferiorly* | TYPE A |
| *aortic arch to* | TYPE A |
| *type A dissection* | TYPE A |
| *ascending aorta, aortic arch and descending aorta* | TYPE A |
| *from the ascending aorta across the aortic arch and* | TYPE A |
| *involves the right brachiocephalic artery, left common carotid and left subclavian artery* | TYPE A |
| *ASCENDINGA AORTA, ARCH AND DESCENDING EXTENDING* | TYPE A |
| *from the aortic valves to the aortic bifurcation* | TYPE A |
| *from the aortic valves to the bifurcation* | TYPE A |
| *flap continues into the descending* | TYPE A |
| *from the root of the aorta and extends into the abdom* | TYPE A |
| *from the aortic valve cusp to the mid ascending thoracic aorta* | TYPE A |
| *brachiocephalic artery and extending into the left external iliac* | TYPE A |
| *from the aortic valve to location just above the aortic bifurcation* | TYPE A |
| *from the aortic root to approximately the bifurcation* | TYPE A |
| *intramural hematoma of the ascending aorta* | TYPE A |
| *ulcer of the ascending aorta* | TYPE A |
| *ascending aorta there is evidence of ulceration* | TYPE A |
| *of the ascending thoracic aorta* | TYPE A |
| *aorta wall below the level of the renal arteries* | |
| *of the descending thoracic aorta with obvious extension* | |
| *in the infrarenal abdominal aorta* | |
| *from the descending thoracic aorta down through* | |
| *mid descending aorta which extends* | |
| *posterior right aspect of the aorta* | |
| *proximal descending thoracic aorta* | |
| *Type B Dissection* | |
| *distal to take off the left subclavian artery* | |
| *TYPE B. AORTIC DISSECTION* | |
| *FROM THE PROXIMAL DESCENDING THORACIC AORTA TO* | |
| *thoracic aorta beginning distal to the origin of the left subclavian* | |
| *TYPE B DISSECTION* | |
| *ORIGIN OF THE LEFT SUBCLAVIAN ARTERY AND EXTENDING* | |
| *type B aortic dissection* | |
| *proximal descending aorta* | |
| *descending or aorta* | |
| *of the infrarenal aorta* | |
| *of the descending aorta* | |
| *INFRARENAL AORTIC ANEURYSM WITH HYPERDENSE CRESCENT SIGN* | |
| *in the proximal descending aorta* | |
| *of the proximal descending aorta* | |
| *in the descending aorta* | |
| *At the diaphragmatic hiatus* | |
| *At the level of the celiac axis* | |
| *Just below the level of the renal arteries* | |
| *at the level of the diaphragmatic crus* | |
| *distal to the left subclavian* | |
| *Infrarenal penetrating aortic ulcer* | |
| *in the descending aorta* | |
| *distal to the origin of the left subclavian artery* | |
| *in the posterolateral descending aorta* | |

*IN DESCENDING AORTA*
*The descending thoracic aorta demonstrates*
*ulcers prior to the bifurcation*
*ulcers in the distal aorta*
*involving the descending thoracic aorta*
*ulcers involving the descending aorta*
*of the distal abdominal aorta*

| | |
|---|---|
| "ascending arch to the aortic bifurcation" | TYPE 1 |
| "ascending arch into" | TYPE 1 |
| "ascending arch into the right external" | TYPE 1 |
| " from proximal descending aorta to" | TYPE 1 |
| "proximal to the takeoff of the left subclavian artery and extend" | TYPE 1 |
| "aortic arch and extending inferiorly" | TYPE 1 |
| "aortic arch to" | TYPE 1 |
| "type A dissection" | TYPE 1 |
| "ascending aorta, aortic arch and descending aorta" | TYPE 1 |
| "from the ascending aorta across the aortic arch and" | TYPE 1 |
| "involves the right brachiocephalic artery, left common carotid and left subclavian artery" | TYPE 1 |
| "ASCENDINGA AORTA, ARCH AND DESCENDING EXTENDING" | TYPE 1 |
| "from the aortic valves to the aortic bifurcation" | TYPE 1 |
| "from the aortic valves to the bifurcation" | TYPE 1 |
| "flap continues into the descending" | TYPE 1 |
| "from the root of the aorta and extends into the abdom" | TYPE 1 |
| "from the aortic valve cusp to the mid ascending thoracic aorta" | TYPE 1 |
| "brachiocephalic artery and extending into the left external iliac" | TYPE 1 |
| "from the aortic valve to location just above the aortic bifurcation" | TYPE 1 |
| "from the aortic root to approximately the bifurcation" | TYPE 1 |
| "intramural hematoma of the ascending aorta" | TYPE 2 |
| "ulcer of the ascending aorta" | TYPE 2 |
| "ascending aorta there is evidence of ulceration" | TYPE 2 |
| "of the ascending thoracic aorta" | TYPE 2 |
| "aorta wall below the level of the renal arteries" | TYPE 3 |
| "of the descending thoracic aorta  with obvious extension" | TYPE 3 |
| "in the infrarenal abdominal aorta" | TYPE 3 |
| "from the descending thoracic aorta down through" | TYPE 3 |
| "mid descending aorta which extends" | TYPE 3 |
| "posterior right aspect of the aorta" | TYPE 3 |
| "proximal descending thoracic aorta" | TYPE 3 |
| "Type B Dissection" | TYPE 3 |
| "distal to take off the left subclavian artery" | TYPE 3 |
| "TYPE B. AORTIC DISSECTION" | TYPE 3 |
| "FROM THE PROXIMAL DESCENDING THORACIC AORTA TO" | TYPE 3 |
| "thoracic aorta beginning distal to the origin of the left subclavian" | TYPE 3 |
| "TYPE B DISSECTION" | TYPE 3 |
| "ORIGIN OF THE LEFT SUBCLAVIAN ARTERY AND EXTENDING" | TYPE 3 |
| "type B aortic dissection" | TYPE 3 |
| "proximal descending aorta" | TYPE 3 |
| "descending or aorta" | TYPE 3 |
| "of the infrarenal aorta" | TYPE 3 |
| "of the descending aorta" | TYPE 3 |
| "INFRARENAL AORTIC ANEURYSM WITH HYPERDENSE CRESCENT SIGN" | TYPE 3 |
| "in the proximal descending aorta" | TYPE 3 |
| "of the proximal descending aorta" | TYPE 3 |
| "in the descending aorta" | TYPE 3 |
| "At the diaphragmatic hiatus" | TYPE 3 |
| "At the level of the celiac axis" | TYPE 3 |
| "Just below the level of the renal arteries" | TYPE 3 |
| "at the level of the diaphragmatic crus" | TYPE 3 |
| "distal to the left subclavian" | TYPE 3 |
| "Infrarenal penetrating aortic ulcer" | TYPE 3 |
| "in the descending aorta" | TYPE 3 |
| "distal to the origin of the left subclavian artery" | TYPE 3 |
| "in the posterolateral descending aorta" | TYPE 3 |

"IN DESCENDING AORTA"         TYPE 3
"The descending thoracic aorta demonstrates"    TYPE 3
"ulcers prior to the bifurcation"    TYPE 3
"ulcers in the distal aorta"    TYPE 3
"involving the descending thoracic aorta"    TYPE 3
"ulcers involving the descending aorta"    TYPE 3
"of the distal abdominal aorta"    TYPE 3

FIGURE 15B

| | |
|---|---|
| *An aortic dissection* | CLASS 2 |
| *Extensive aortic dissection* | CLASS 2 |
| *Positive aortic dissection* | CLASS 2 |
| *Type III* | CLASS 1 |
| *Type II* | CLASS 1 |
| *Type I* | CLASS 1 |
| *suggestive of thrombosed dissection* | CLASS 1 |
| *CONSISTENT WITH AORTIC DISSECTION* | CLASS 2 |
| *Large aortic dissection* | CLASS 2 |
| *FOCAL DISSECTION* | CLASS 2 |
| is evidence of a flap within the aorta | CLASS 2 |
| Dissection extending from proximal descending aorta to | CLASS 2 |
| *Type 1 aortic dissection* | CLASS 1 |
| *Type 2 aortic dissection* | CLASS 1 |
| *Type 3 aortic dissection* | CLASS 1 |
| *Type A aortic dissection* | CLASS 1 |
| *Type B aortic dissection* | CLASS 1 |
| *Focal dissection* | CLASS 1 |
| *An intimal flap is noted* | CLASS 1 |
| *Type I aortic dissection* | CLASS 1 |
| *intimal flap is* | CLASS 1 |
| *Focal dissection of the infrarenal abdominal aorta* | CLASS 1 |
| *Focal dissection of the suprarenal abdominal aorta* | CLASS 1 |
| *Focal dissection of the thoracic aorta* | CLASS 1 |
| *Extensive aortic dissection* | CLASS 2 |
| *Small aortic dissection* | CLASS 1 |
| *Tiny aortic dissection* | CLASS 1 |
| *Positive intimal flap* | CLASS 1 |
| *Intimal flap consistent* | CLASS 1 |
| *Type 1 dissection* | CLASS 1 |
| *Type 2 dissection* | CLASS 1 |
| *Type 3 dissection* | CLASS 1 |
| *Type A dissection* | CLASS 1 |
| *Type B dissection* | CLASS 1 |
| *thrombosed aortic dissection* | CLASS 1 |
| *thoracic aortic dissection* | CLASS 1 |
| *abdominal aortic dissection* | CLASS 1 |
| *thoracic dissection* | CLASS 1 |
| *abdominal dissection* | CLASS 1 |
| *dissection of the aorta* | CLASS 1 |
| *type A dissection* | CLASS 1 |
| *intimal flap extending* | CLASS 1 |
| *an intimal flap* | CLASS 1 |
| *The aortic dissection* | CLASS 1 |
| *The dissection flap* | CLASS 1 |
| *TYPE A DISSECTION* | CLASS 1 |
| *large aortic dissection* | CLASS 1 |
| *intimal flap originating* | CLASS 1 |
| *TYPE 1 AORTIC DISSECTION* | CLASS 1 |
| *Type 1 thrombosed aortic dissection* | CLASS 1 |
| *is an intimal aortic flap* | CLASS 1 |
| *Ascending thoracic aortic dissection* | CLASS 1 |
| *type A aortic dissection* | CLASS 1 |
| *dissection of the aorta extending* | CLASS 1 |

| | |
|---|---|
| 'No evidence of an An aortic dissection' | NEG CLASS 1 |
| 'No evidence of an Extensive aortic dissection' | NEG CLASS 1 |
| 'No evidence of an Positive aortic dissection' | NEG CLASS 1 |
| 'No evidence of an Type III' | NEG CLASS 1 |
| 'No evidence of an Type II' | NEG CLASS 1 |
| 'No evidence of an Type I' | NEG CLASS 1 |
| 'No evidence of an suggestive of thrombosed dissection' | NEG CLASS 1 |
| 'No evidence of an CONSISTENT WITH AORTIC DISSECTION' | NEG CLASS 1 |
| 'No evidence of an Large aortic dissection' | NEG CLASS 1 |
| 'No evidence of an FOCAL DISSECTION' | NEG CLASS 1 |
| 'No evidence of an is evidence of a flap within the aorta' | NEG CLASS 1 |
| 'No evidence of an Dissection extending from proximal descending aorta to' | NEG CLASS 1 |
| 'No evidence of an Type 1 aortic dissection' | NEG CLASS 1 |
| 'No evidence of an Type 2 aortic dissection' | NEG CLASS 1 |
| 'No evidence of an Type 3 aortic dissection' | NEG CLASS 1 |
| 'No evidence of an Type A aortic dissection' | NEG CLASS 1 |
| 'No evidence of an Type B aortic dissection' | NEG CLASS 1 |
| 'No evidence of an Focal dissection' | NEG CLASS 1 |
| 'No evidence of an An intimal flap is noted' | NEG CLASS 1 |
| 'No evidence of an Type I aortic dissection' | NEG CLASS 1 |
| 'No evidence of an intimal flap is' | NEG CLASS 1 |
| 'No evidence of an Focal dissection of the infrarenal abdominal aorta' | NEG CLASS 1 |
| 'No evidence of an Focal dissection of the suprarenal abdominal aorta' | NEG CLASS 1 |
| 'No evidence of an Focal dissection of the thoracic aorta' | NEG CLASS 1 |
| 'No evidence of an Extensive aortic dissection' | NEG CLASS 1 |
| 'No evidence of an Small aortic dissection' | NEG CLASS 1 |
| 'No evidence of an Tiny aortic dissection' | NEG CLASS 1 |
| 'No evidence of an Positive intimal flap' | NEG CLASS 1 |
| 'No evidence of an Intimal flap consistent' | NEG CLASS 1 |
| 'No evidence of an Type 1 dissection' | NEG CLASS 1 |
| 'No evidence of an Type 2 dissection' | NEG CLASS 1 |
| 'No evidence of an Type 3 dissection' | NEG CLASS 1 |
| 'No evidence of an Type A dissection' | NEG CLASS 1 |
| 'No evidence of an Type B dissection' | NEG CLASS 1 |
| 'No evidence of an thrombosed aortic dissection' | NEG CLASS 1 |
| 'No evidence of an thoracic aortic dissection' | NEG CLASS 1 |
| 'No evidence of an abdominal aortic dissection' | NEG CLASS 1 |
| 'No evidence of an thoracic dissection' | NEG CLASS 1 |
| 'No evidence of an abdominal dissection' | NEG CLASS 1 |
| 'No evidence of an dissection of the aorta' | NEG CLASS 1 |
| 'No evidence of an type A dissection' | NEG CLASS 1 |
| 'No evidence of an intimal flap extending' | NEG CLASS 1 |
| 'No evidence of an an intimal flap' | NEG CLASS 1 |
| 'No evidence of an The aortic dissection' | NEG CLASS 1 |
| 'No evidence of an The dissection flap' | NEG CLASS 1 |
| 'No evidence of an TYPE A DISSECTION' | NEG CLASS 1 |
| 'No evidence of an large aortic dissection' | NEG CLASS 1 |
| 'No evidence of an intimal flap originating' | NEG CLASS 1 |
| 'No evidence of an TYPE 1 AORTIC DISSECTION' | NEG CLASS 1 |
| 'No evidence of an Type 1 thrombosed aortic dissection' | NEG CLASS 1 |
| 'No evidence of an is an intimal aortic flap' | NEG CLASS 1 |
| 'No evidence of an Ascending thoracic aortic dissection' | NEG CLASS 1 |
| 'No evidence of an type A aortic dissection' | NEG CLASS 1 |
| 'No evidence of an dissection of the aorta extending' | NEG CLASS 1 |
| 'No evidence of a An aortic dissection' | NEG CLASS 1 |
| 'No evidence of a Extensive aortic dissection' | NEG CLASS 1 |

FIGURE 17A

| | | |
|---|---|---|
| *No evidence of a Positive aortic dissection* | NEG CLASS 1 | |
| *No evidence of a Type III* | NEG CLASS 1 | |
| *No evidence of a Type II* | NEG CLASS 1 | |
| *No evidence of a Type I* | NEG CLASS 1 | |
| *No evidence of a suggestive of thrombosed dissection* | NEG CLASS 1 | ~353 |
| *No evidence of a CONSISTENT WITH AORTIC DISSECTION* | NEG CLASS 1 | |
| *No evidence of a Large aortic dissection* | NEG CLASS 1 | |
| *No evidence of a FOCAL DISSECTION* | NEG CLASS 1 | |
| *No evidence of a is evidence of a flap within the aorta* | NEG CLASS 1 | |
| *No evidence of a Dissection extending from proximal descending aorta to* | NEG CLASS 1 | |
| *No evidence of a Type 1 aortic dissection* | NEG CLASS 1 | |
| *No evidence of a Type 2 aortic dissection* | NEG CLASS 1 | |
| *No evidence of a Type 3 aortic dissection* | NEG CLASS 1 | |
| *No evidence of a Type A aortic dissection* | NEG CLASS 1 | |
| *No evidence of a Type B aortic dissection* | NEG CLASS 1 | |
| *No evidence of a Focal dissection* | NEG CLASS 1 | |
| *No evidence of a An intimal flap is noted* | NEG CLASS 1 | |
| *No evidence of a Type I aortic dissection* | NEG CLASS 1 | |
| *No evidence of a intimal flap is* | NEG CLASS 1 | |
| *No evidence of a Focal dissection of the infrarenal abdominal aorta* | NEG CLASS 1 | |
| *No evidence of a Focal dissection of the suprarenal abdominal aorta* | NEG CLASS 1 | |
| *No evidence of a Focal dissection of the thoracic aorta* | NEG CLASS 1 | |
| *No evidence of a Extensive aortic dissection* | NEG CLASS 1 | |
| *No evidence of a Small aortic dissection* | NEG CLASS 1 | |
| *No evidence of a Tiny aortic dissection* | NEG CLASS 1 | |
| *No evidence of a Positive intimal flap* | NEG CLASS 1 | |
| *No evidence of a Intimal flap consistent* | NEG CLASS 1 | |
| *No evidence of a Type 1 dissection* | NEG CLASS 1 | |
| *No evidence of a Type 2 dissection* | NEG CLASS 1 | |
| *No evidence of a Type 3 dissection* | NEG CLASS 1 | |
| *No evidence of a Type A dissection* | NEG CLASS 1 | |
| *No evidence of a Type B dissection* | NEG CLASS 1 | |
| *No evidence of a thrombosed aortic dissection* | NEG CLASS 1 | |
| *No evidence of a thoracic aortic dissection* | NEG CLASS 1 | |
| *No evidence of a abdominal aortic dissection* | NEG CLASS 1 | |
| *No evidence of a thoracic dissection* | NEG CLASS 1 | |
| *No evidence of a abdominal dissection* | NEG CLASS 1 | |
| *No evidence of a dissection of the aorta* | NEG CLASS 1 | |
| *No evidence of a type A dissection* | NEG CLASS 1 | |
| *No evidence of a intimal flap extending* | NEG CLASS 1 | |
| *No evidence of a an intimal flap* | NEG CLASS 1 | |
| *No evidence of a The aortic dissection* | NEG CLASS 1 | |
| *No evidence of a The dissection flap* | NEG CLASS 1 | |
| *No evidence of a TYPE A DISSECTION* | NEG CLASS 1 | |
| *No evidence of a large aortic dissection* | NEG CLASS 1 | |
| *No evidence of a intimal flap originating* | NEG CLASS 1 | |
| *No evidence of a TYPE 1 AORTIC DISSECTION* | NEG CLASS 1 | |
| *No evidence of a Type 1 thrombosed aortic dissection* | NEG CLASS 1 | |
| *No evidence of a is an intimal aortic flap* | NEG CLASS 1 | |
| *No evidence of a Ascending thoracic aortic dissection* | NEG CLASS 1 | |
| *No evidence of a type A aortic dissection* | NEG CLASS 1 | |
| *No evidence of a dissection of the aorta extending* | NEG CLASS 1 | |
| *No evidence of An aortic dissection* | NEG CLASS 1 | |
| *No evidence of Extensive aortic dissection* | NEG CLASS 1 | |
| *No evidence of Positive aortic dissection* | NEG CLASS 1 | |
| *No evidence of Type III* | NEG CLASS 1 | |

FIGURE 17B

| | |
|---|---|
| *No evidence of Type II* | NEG CLASS 1 |
| *No evidence of Type I* | NEG CLASS 1 |
| *No evidence of suggestive of thrombosed dissection* | NEG CLASS 1 |
| *No evidence of CONSISTENT WITH AORTIC DISSECTION* | NEG CLASS 1 |
| *No evidence of Large aortic dissection* | NEG CLASS 1 |
| *No evidence of FOCAL DISSECTION* | NEG CLASS 1 |
| *No evidence of is evidence of a flap within the aorta* | NEG CLASS 1 |
| *No evidence of Dissection extending from proximal descending aorta to* | NEG CLASS 1 |
| *No evidence of Type 1 aortic dissection* | NEG CLASS 1 |
| *No evidence of Type 2 aortic dissection* | NEG CLASS 1 |
| *No evidence of Type 3 aortic dissection* | NEG CLASS 1 |
| *No evidence of Type A aortic dissection* | NEG CLASS 1 |
| *No evidence of Type B aortic dissection* | NEG CLASS 1 |
| *No evidence of Focal dissection* | NEG CLASS 1 |
| *No evidence of An intimal flap is noted* | NEG CLASS 1 |
| *No evidence of Type I aortic dissection* | NEG CLASS 1 |
| *No evidence of intimal flap is* | NEG CLASS 1 |
| *No evidence of Focal dissection of the infrarenal abdominal aorta* | NEG CLASS 1 |
| *No evidence of Focal dissection of the suprarenal abdominal aorta* | NEG CLASS 1 |
| *No evidence of Focal dissection of the thoracic aorta* | NEG CLASS 1 |
| *No evidence of Extensive aortic dissection* | NEG CLASS 1 |
| *No evidence of Small aortic dissection* | NEG CLASS 1 |
| *No evidence of Tiny aortic dissection* | NEG CLASS 1 |
| *No evidence of Positive intimal flap* | NEG CLASS 1 |
| *No evidence of Intimal flap consistent* | NEG CLASS 1 |
| *No evidence of Type 1 dissection* | NEG CLASS 1 |
| *No evidence of Type 2 dissection* | NEG CLASS 1 |
| *No evidence of Type 3 dissection* | NEG CLASS 1 |
| *No evidence of Type A dissection* | NEG CLASS 1 |
| *No evidence of Type B dissection* | NEG CLASS 1 |
| *No evidence of thrombosed aortic dissection* | NEG CLASS 1 |
| *No evidence of thoracic aortic dissection* | NEG CLASS 1 |
| *No evidence of abdominal aortic dissection* | NEG CLASS 1 |
| *No evidence of thoracic dissection* | NEG CLASS 1 |
| *No evidence of abdominal dissection* | NEG CLASS 1 |
| *No evidence of dissection of the aorta* | NEG CLASS 1 |
| *No evidence of type A dissection* | NEG CLASS 1 |
| *No evidence of intimal flap extending* | NEG CLASS 1 |
| *No evidence of an intimal flap* | NEG CLASS 1 |
| *No evidence of The aortic dissection* | NEG CLASS 1 |
| *No evidence of The dissection flap* | NEG CLASS 1 |
| *No evidence of TYPE A DISSECTION* | NEG CLASS 1 |
| *No evidence of large aortic dissection* | NEG CLASS 1 |
| *No evidence of intimal flap originating* | NEG CLASS 1 |
| *No evidence of TYPE 1 AORTIC DISSECTION* | NEG CLASS 1 |
| *No evidence of Type 1 thrombosed aortic dissection* | NEG CLASS 1 |
| *No evidence of is an intimal aortic flap* | NEG CLASS 1 |
| *No evidence of Ascending thoracic aortic dissection* | NEG CLASS 1 |
| *No evidence of type A aortic dissection* | NEG CLASS 1 |
| *No evidence of dissection of the aorta extending* | NEG CLASS 1 |
| *No dissection* | NEG CLASS 1 |
| *No aortic dissection* | NEG CLASS 1 |
| *No intimal* | NEG CLASS 1 |

*represents intramural hematoma*
*is a intramural hematoma*
*suggestive of intramural hematoma*
*hemorrhage into the aortic wall*
*HYPERDENSE CRESCENT SIGN*
*represent an intramural hematoma*
*crescentic region of increased attenuation*
*increased crescentic attenuation*
*aneurysm/pseudo aneurysm*
*a focal intramural hematoma*
*focal mural hematoma*
*eccentric bulge*
*intramural hemorrhage*
*which suggests intramural hematoma*
*is focal ectasia*
*An anterior intramural hematoma*
*extends along the wall of the aorta*
*consistent with a aortic wall ulceration/aortic dissection*
*CONSISTENT WITH AORTIC ULCERATION/DISSECTION*
*with intramural thrombus*
*consistent with acute intramural hematoma*
*likely associated intramural hematoma*
*crescentic of intramural high density*
*consistent with an acute intramural hemorrhage*
*intramural leak of contrast*
*medial displacement of the calcified intima*
*into intramural hematoma*
*with focal intramural dissection*
*with associated intramural hemorrhage*

| | |
|---|---|
| "hematoma without change" | STABLE CLASS 2 |
| "hematoma stable compared to prior" | STABLE CLASS 2 |
| "hematoma is unchanged" | STABLE CLASS 2 |
| "hematoma stable since last" | STABLE CLASS 2 |
| "hematoma no change" | STABLE CLASS 2 |
| "hematoma not increased in size" | STABLE CLASS 2 |
| "hematoma unchanged in size" | STABLE CLASS 2 |
| "hematoma essentially unchanged" | STABLE CLASS 2 |
| *No change in appearance of hematoma* | STABLE CLASS 2 |
| "hemorrhage without change" | STABLE CLASS 2 |
| "hemorrhage stable compared to prior" | STABLE CLASS 2 |
| "hemorrhage is unchanged" | STABLE CLASS 2 |
| "hemorrhage stable since last" | STABLE CLASS 2 |
| "hemorrhage no change" | STABLE CLASS 2 |
| "hemmorrhage not increased in size" | STABLE CLASS 2 |
| "hemorrhage unchanged in size" | STABLE CLASS 2 |
| "hemorrhage essentially unchanged" | STABLE CLASS 2 |
| *No change in appearance of hemorrhage* | STABLE CLASS 2 |
| "eccentric bulge without change" | STABLE CLASS 2 |
| "eccentric bulge stable compared to prior" | STABLE CLASS 2 |
| "eccentric bulge is unchanged" | STABLE CLASS 2 |
| "eccentric bulge stable since last" | STABLE CLASS 2 |
| "eccentric bulge no change" | STABLE CLASS 2 |
| "represents intramural hematoma without change" | STABLE CLASS 2 |
| "is a intramural hematoma without change" | STABLE CLASS 2 |
| "suggestive of intramural hematoma without change" | STABLE CLASS 2 |
| "hemorrhage into the aortic wall without change" | STABLE CLASS 2 |
| "HYPERDENSE CRESCENT SIGN without change" | STABLE CLASS 2 |
| "represent an intramural hematoma without change" | STABLE CLASS 2 |
| "crescentic region of increased attenuation without change" | STABLE CLASS 2 |
| "increased crescentic attenuation without change" | STABLE CLASS 2 |
| "aneurysm/pseudo aneurysm without change" | STABLE CLASS 2 |
| "a focal intramural hematoma without change" | STABLE CLASS 2 |
| "focal mural hematoma without change" | STABLE CLASS 2 |
| "eccentric bulge without change" | STABLE CLASS 2 |
| "Intramural hemorrhage without change" | STABLE CLASS 2 |
| "which suggests intramural hematoma without change" | STABLE CLASS 2 |
| "is focal ectasia without change" | STABLE CLASS 2 |
| "An anterior intramural hematoma without change" | STABLE CLASS 2 |
| "extends along the wall of the aorta without change" | STABLE CLASS 2 |
| "consistent with a aortic wall ulceration/aortic dissection without change" | STABLE CLASS 2 |
| "CONSISTENT WITH AORTIC ULCERATION/DISSECTION without change" | STABLE CLASS 2 |
| "with intramural thrombus without change" | STABLE CLASS 2 |
| "consistent with acute intramural hematoma without change" | STABLE CLASS 2 |
| "likely associated intramural hematoma without change" | STABLE CLASS 2 |
| "crescentic of intramural high density without change" | STABLE CLASS 2 |
| "consistent with an acute intramural hemorrhage without change" | STABLE CLASS 2 |
| "intramural leak of contrast without change" | STABLE CLASS 2 |
| "medial displacement of the calcified intima without change" | STABLE CLASS 2 |
| "into intramural hematoma without change" | STABLE CLASS 2 |
| "with focal intramural dissection without change" | STABLE CLASS 2 |
| "with associated intramural hemorrhage without change" | STABLE CLASS 2 |
| "represents intramural hematoma stable compared to prior" | STABLE CLASS 2 |
| "is a intramural hematoma stable compared to prior" | STABLE CLASS 2 |
| "suggestive of intramural hematoma stable compared to prior" | STABLE CLASS 2 |
| "hemorrhage into the aortic wall stable compared to prior" | STABLE CLASS 2 |
| "HYPERDENSE CRESCENT SIGN stable compared to prior" | STABLE CLASS 2 |
| "represent an intramural hematoma stable compared to prior" | STABLE CLASS 2 |
| "crescentic region of increased attenuation stable compared to prior" | STABLE CLASS 2 |

| | |
|---|---|
| "increased crescentic attenuation stable compared to prior" | STABLE CLASS 2 |
| "aneurysm/pseudo aneurysm stable compared to prior" | STABLE CLASS 2 |
| "a focal intramural hematoma stable compared to prior" | STABLE CLASS 2 |
| "focal mural hematoma stable compared to prior" | STABLE CLASS 2 |
| "eccentric bulge stable compared to prior" | STABLE CLASS 2 |
| "intramural hemorrhage stable compared to prior" | STABLE CLASS 2 |
| "which suggests intramural hematoma stable compared to prior" | STABLE CLASS 2 |
| "is focal ectasia stable compared to prior" | STABLE CLASS 2 |
| "An anterior intramural hematoma stable compared to prior" | STABLE CLASS 2 |
| "extends along the wall of the aorta stable compared to prior" | STABLE CLASS 2 |
| "consistent with a aortic wall ulceration/aortic dissection stable compared to prior" | STABLE CLASS 2 |
| "CONSISTENT WITH AORTIC ULCERATION/DISSECTION stable compared to prior" | STABLE CLASS 2 |
| "with intramural thrombus stable compared to prior" | STABLE CLASS 2 |
| "consistent with acute intramural hematoma stable compared to prior" | STABLE CLASS 2 |
| "likely associated intramural hematoma stable compared to prior" | STABLE CLASS 2 |
| "crescentic of intramural high density stable compared to prior" | STABLE CLASS 2 |
| "consistent with an acute intramural hemorrhage stable compared to prior" | STABLE CLASS 2 |
| "intramural leak of contrast stable compared to prior" | STABLE CLASS 2 |
| "medial displacement of the calcified intima stable compared to prior" | STABLE CLASS 2 |
| "into intramural hematoma stable compared to prior" | STABLE CLASS 2 |
| "with focal intramural dissection stable compared to prior" | STABLE CLASS 2 |
| "with associated intramural hemorrhage stable compared to prior" | STABLE CLASS 2 |
| "represents intramural hematoma is unchanged" | STABLE CLASS 2 |
| "is a intramural hematoma is unchanged" | STABLE CLASS 2 |
| "suggestive of intramural hematoma is unchanged" | STABLE CLASS 2 |
| "hemorrhage into the aortic wall is unchanged" | STABLE CLASS 2 |
| "HYPERDENSE CRESCENT SIGN is unchanged" | STABLE CLASS 2 |
| "represent an intramural hematoma is unchanged" | STABLE CLASS 2 |
| "crescentic region of increased attenuation is unchanged" | STABLE CLASS 2 |
| "increased crescentic attenuation is unchanged" | STABLE CLASS 2 |
| "aneurysm/pseudo aneurysm is unchanged" | STABLE CLASS 2 |
| "a focal intramural hematoma is unchanged" | STABLE CLASS 2 |
| "focal mural hematoma is unchanged" | STABLE CLASS 2 |
| "eccentric bulge is unchanged" | STABLE CLASS 2 |
| "intramural hemorrhage is unchanged" | STABLE CLASS 2 |
| "which suggests intramural hematoma is unchanged" | STABLE CLASS 2 |
| "is focal ectasia is unchanged" | STABLE CLASS 2 |
| "An anterior intramural hematoma is unchanged" | STABLE CLASS 2 |
| "extends along the wall of the aorta is unchanged" | STABLE CLASS 2 |
| "consistent with a aortic wall ulceration/aortic dissection is unchanged" | STABLE CLASS 2 |
| "CONSISTENT WITH AORTIC ULCERATION/DISSECTION is unchanged" | STABLE CLASS 2 |
| "with intramural thrombus is unchanged" | STABLE CLASS 2 |
| "consistent with acute intramural hematoma is unchanged" | STABLE CLASS 2 |
| "likely associated intramural hematoma is unchanged" | STABLE CLASS 2 |
| "crescentic of intramural high density is unchanged" | STABLE CLASS 2 |
| "consistent with an acute intramural hemorrhage is unchanged" | STABLE CLASS 2 |
| "intramural leak of contrast is unchanged" | STABLE CLASS 2 |
| "medial displacement of the calcified intima is unchanged" | STABLE CLASS 2 |
| "into intramural hematoma is unchanged" | STABLE CLASS 2 |
| "with focal intramural dissection is unchanged" | STABLE CLASS 2 |
| "with associated intramural hemorrhage is unchanged" | STABLE CLASS 2 |
| "represents intramural hematoma stable since last" | STABLE CLASS 2 |
| "is a intramural hematoma stable since last" | STABLE CLASS 2 |
| "suggestive of intramural hematoma stable since last" | STABLE CLASS 2 |
| "hemorrhage into the aortic wall stable since last" | STABLE CLASS 2 |
| "HYPERDENSE CRESCENT SIGN stable since last" | STABLE CLASS 2 |
| "represent an intramural hematoma stable since last" | STABLE CLASS 2 |
| "crescentic region of increased attenuation stable since last" | STABLE CLASS 2 |
| "increased crescentic attenuation stable since last" | STABLE CLASS 2 |

| | |
|---|---|
| *aneurysm/pseudo aneurysm stable since last* | STABLE CLASS 2 |
| *a focal intramural hematoma stable since last* | STABLE CLASS 2 |
| *focal mural hematoma stable since last* | STABLE CLASS 2 |
| *eccentric bulge stable since last* | STABLE CLASS 2 |
| *intramural hemorrhage stable since last* | STABLE CLASS 2 |
| *which suggests intramural hematoma stable since last* | STABLE CLASS 2 |
| *is focal ectasia stable since last* | STABLE CLASS 2 |
| *An anterior intramural hematoma stable since last* | STABLE CLASS 2 |
| *extends along the wall of the aorta stable since last* | STABLE CLASS 2 |
| *consistent with a aortic wall ulceration/aortic dissection stable since last* | STABLE CLASS 2 |
| *CONSISTENT WITH AORTIC ULCERATION/DISSECTION stable since last* | STABLE CLASS 2 |
| *with intramural thrombus stable since last* | STABLE CLASS 2 |
| *consistent with acute intramural hematoma stable since last* | STABLE CLASS 2 |
| *likely associated intramural hematoma stable since last* | STABLE CLASS 2 |
| *crescentic of intramural high density stable since last* | STABLE CLASS 2 |
| *consistent with an acute intramural hemorrhage stable since last* | STABLE CLASS 2 |
| *intramural leak of contrast stable since last* | STABLE CLASS 2 |
| *medial displacement of the calcified intima stable since last* | STABLE CLASS 2 |
| *into intramural hematoma stable since last* | STABLE CLASS 2 |
| *with focal intramural dissection stable since last* | STABLE CLASS 2 |
| *with associated intramural hemorrhage stable since last* | STABLE CLASS 2 |
| *represents intramural hematoma no change* | STABLE CLASS 2 |
| *is a intramural hematoma no change* | STABLE CLASS 2 |
| *suggestive of intramural hematoma no change* | STABLE CLASS 2 |
| *hemorrhage into the aortic wall no change* | STABLE CLASS 2 |
| *HYPERDENSE CRESCENT SIGN no change* | STABLE CLASS 2 |
| *represent an intramural hematoma no change* | STABLE CLASS 2 |
| *crescentic region of increased attenuation no change* | STABLE CLASS 2 |
| *increased crescentic attenuation no change* | STABLE CLASS 2 |
| *aneurysm/pseudo aneurysm no change* | STABLE CLASS 2 |
| *a focal intramural hematoma no change* | STABLE CLASS 2 |
| *focal mural hematoma no change* | STABLE CLASS 2 |
| *eccentric bulge no change* | STABLE CLASS 2 |
| *intramural hemorrhage no change* | STABLE CLASS 2 |
| *which suggests intramural hematoma no change* | STABLE CLASS 2 |
| *is focal ectasia no change* | STABLE CLASS 2 |
| *An anterior intramural hematoma no change* | STABLE CLASS 2 |
| *extends along the wall of the aorta no change* | STABLE CLASS 2 |
| *consistent with a aortic wall ulceration/aortic dissection no change* | STABLE CLASS 2 |
| *CONSISTENT WITH AORTIC ULCERATION/DISSECTION no change* | STABLE CLASS 2 |
| *with intramural thrombus no change* | STABLE CLASS 2 |
| *consistent with acute intramural hematoma no change* | STABLE CLASS 2 |
| *likely associated intramural hematoma no change* | STABLE CLASS 2 |
| *crescentic of intramural high density no change* | STABLE CLASS 2 |
| *consistent with an acute intramural hemorrhage no change* | STABLE CLASS 2 |
| *intramural leak of contrast no change* | STABLE CLASS 2 |
| *medial displacement of the calcified intima no change* | STABLE CLASS 2 |
| *into intramural hematoma no change* | STABLE CLASS 2 |
| *with focal intramural dissection no change* | STABLE CLASS 2 |
| *with associated intramural hemorrhage no change* | STABLE CLASS 2 |
| *represents intramural hematoma not increased in size* | STABLE CLASS 2 |
| *is a intramural hematoma not increased in size* | STABLE CLASS 2 |
| *suggestive of intramural hematoma not increased in size* | STABLE CLASS 2 |
| *hemorrhage into the aortic wall not increased in size* | STABLE CLASS 2 |
| *HYPERDENSE CRESCENT SIGN not increased in size* | STABLE CLASS 2 |
| *represent an intramural hematoma not increased in size* | STABLE CLASS 2 |
| *crescentic region of increased attenuation not increased in size* | STABLE CLASS 2 |
| *increased crescentic attenuation not increased in size* | STABLE CLASS 2 |
| *aneurysm/pseudo aneurysm not increased in size* | STABLE CLASS 2 |

| | |
|---|---|
| *a focal intramural hematoma not increased in size* | STABLE CLASS 2 |
| *focal mural hematoma not increased in size* | STABLE CLASS 2 |
| *eccentric bulge not increased in size* | STABLE CLASS 2 |
| *intramural hemorrhage not increased in size* | STABLE CLASS 2 |
| *which suggests intramural hematoma not increased in size* | STABLE CLASS 2 |
| *is focal ectasia not increased in size* | STABLE CLASS 2 |
| *An anterior intramural hematoma not increased in size* | STABLE CLASS 2 |
| *extends along the wall of the aorta not increased in size* | STABLE CLASS 2 |
| *consistent with a aortic wall ulceration/aortic dissection not increased in size* | STABLE CLASS 2 |
| *CONSISTENT WITH AORTIC ULCERATION/DISSECTION not increased in size* | STABLE CLASS 2 |
| *with intramural thrombus not increased in size* | STABLE CLASS 2 |
| *consistent with acute intramural hematoma not increased in size* | STABLE CLASS 2 |
| *likely associated intramural hematoma not increased in size* | STABLE CLASS 2 |
| *crescentic of intramural high density not increased in size* | STABLE CLASS 2 |
| *consistent with an acute intramural hemorrhage not increased in size* | STABLE CLASS 2 |
| *intramural leak of contrast not increased in size* | STABLE CLASS 2 |
| *medial displacement of the calcified intima not increased in size* | STABLE CLASS 2 |
| *into intramural hematoma not increased in size* | STABLE CLASS 2 |
| *with focal intramural dissection not increased in size* | STABLE CLASS 2 |
| *with associated intramural hemorrhage not increased in size* | STABLE CLASS 2 |
| *represents intramural hematoma unchanged in size* | STABLE CLASS 2 |
| *is a intramural hematoma unchanged in size* | STABLE CLASS 2 |
| *suggestive of intramural hematoma unchanged in size* | STABLE CLASS 2 |
| *hemorrhage into the aortic wall unchanged in size* | STABLE CLASS 2 |
| *HYPERDENSE CRESCENT SIGN unchanged in size* | STABLE CLASS 2 |
| *represent an intramural hematoma unchanged in size* | STABLE CLASS 2 |
| *crescentic region of increased attenuation unchanged in size* | STABLE CLASS 2 |
| *increased crescentic attenuation unchanged in size* | STABLE CLASS 2 |
| *aneurysm/pseudo aneurysm unchanged in size* | STABLE CLASS 2 |
| *a focal intramural hematoma unchanged in size* | STABLE CLASS 2 |
| *focal mural hematoma unchanged in size* | STABLE CLASS 2 |
| *eccentric bulge unchanged in size* | STABLE CLASS 2 |
| *intramural hemorrhage unchanged in size* | STABLE CLASS 2 |
| *which suggests intramural hematoma unchanged in size* | STABLE CLASS 2 |
| *is focal ectasia unchanged in size* | STABLE CLASS 2 |
| *An anterior intramural hematoma unchanged in size* | STABLE CLASS 2 |
| *extends along the wall of the aorta unchanged in size* | STABLE CLASS 2 |
| *consistent with a aortic wall ulceration/aortic dissection unchanged in size* | STABLE CLASS 2 |
| *CONSISTENT WITH AORTIC ULCERATION/DISSECTION unchanged in size* | STABLE CLASS 2 |
| *with intramural thrombus unchanged in size* | STABLE CLASS 2 |
| *consistent with acute intramural hematoma unchanged in size* | STABLE CLASS 2 |
| *likely associated intramural hematoma unchanged in size* | STABLE CLASS 2 |
| *crescentic of intramural high density unchanged in size* | STABLE CLASS 2 |
| *consistent with an acute intramural hemorrhage unchanged in size* | STABLE CLASS 2 |
| *intramural leak of contrast unchanged in size* | STABLE CLASS 2 |
| *medial displacement of the calcified intima unchanged in size* | STABLE CLASS 2 |
| *into intramural hematoma unchanged in size* | STABLE CLASS 2 |
| *with focal intramural dissection unchanged in size* | STABLE CLASS 2 |
| *with associated intramural hemorrhage unchanged in size* | STABLE CLASS 2 |
| *represents intramural hematoma essentially unchanged* | STABLE CLASS 2 |
| *is a intramural hematoma essentially unchanged* | STABLE CLASS 2 |
| *suggestive of intramural hematoma essentially unchanged* | STABLE CLASS 2 |
| *hemorrhage into the aortic wall essentially unchanged* | STABLE CLASS 2 |
| *HYPERDENSE CRESCENT SIGN essentially unchanged* | STABLE CLASS 2 |
| *represent an intramural hematoma essentially unchanged* | STABLE CLASS 2 |
| *crescentic region of increased attenuation essentially unchanged* | STABLE CLASS 2 |
| *increased crescentic attenuation essentially unchanged* | STABLE CLASS 2 |
| *aneurysm/pseudo aneurysm essentially unchanged* | STABLE CLASS 2 |
| *a focal intramural hematoma essentially unchanged* | STABLE CLASS 2 |

| | |
|---|---|
| "focal mural hematoma essentially unchanged" | STABLE CLASS 2 |
| "eccentric bulge essentially unchanged" | STABLE CLASS 2 |
| "intramural hemorrhage essentially unchanged" | STABLE CLASS 2 |
| "which suggests intramural hematoma essentially unchanged" | STABLE CLASS 2 |
| "is focal ectasia essentially unchanged" | STABLE CLASS 2 |
| "An anterior intramural hematoma essentially unchanged" | STABLE CLASS 2 |
| "extends along the wall of the aorta essentially unchanged" | STABLE CLASS 2 |
| "consistent with a aortic wall ulceration/aortic dissection essentially unchanged" | STABLE CLASS 2 |
| "CONSISTENT WITH AORTIC ULCERATION/DISSECTION essentially unchanged" | STABLE CLASS 2 |
| "with intramural thrombus essentially unchanged" | STABLE CLASS 2 |
| "consistent with acute intramural hematoma essentially unchanged" | STABLE CLASS 2 |
| "likely associated intramural hematoma essentially unchanged" | STABLE CLASS 2 |
| "crescentic of intramural high density essentially unchanged" | STABLE CLASS 2 |
| "consistent with an acute intramural hemorrhage essentially unchanged" | STABLE CLASS 2 |
| "intramural leak of contrast essentially unchanged" | STABLE CLASS 2 |
| "medial displacement of the calcified intima essentially unchanged" | STABLE CLASS 2 |
| "into intramural hematoma essentially unchanged" | STABLE CLASS 2 |
| "with focal intramural dissection essentially unchanged" | STABLE CLASS 2 |
| "with associated intramural hemorrhage essentially unchanged" | STABLE CLASS 2 |
| "No change in appearance of represents intramural hematoma" | STABLE CLASS 2 |
| "No change in appearance of is a intramural hematoma" | STABLE CLASS 2 |
| "No change in appearance of suggestive of intramural hematoma" | STABLE CLASS 2 |
| "No change in appearance of hemorrhage into the aortic wall" | STABLE CLASS 2 |
| "No change in appearance of HYPERDENSE CRESCENT SIGN" | STABLE CLASS 2 |
| "No change in appearance of represent an intramural hematoma" | STABLE CLASS 2 |
| "No change in appearance of crescentic region of increased attenuation" | STABLE CLASS 2 |
| "No change in appearance of increased crescentic attenuation" | STABLE CLASS 2 |
| "No change in appearance of aneurysm/pseudo aneurysm" | STABLE CLASS 2 |
| "No change in appearance of a focal intramural hematoma" | STABLE CLASS 2 |
| "No change in appearance of focal mural hematoma" | STABLE CLASS 2 |
| "No change in appearance of eccentric bulge" | STABLE CLASS 2 |
| "No change in appearance of intramural hemorrhage" | STABLE CLASS 2 |
| "No change in appearance of which suggests intramural hematoma" | STABLE CLASS 2 |
| "No change in appearance of is focal ectasia" | STABLE CLASS 2 |
| "No change in appearance of An anterior intramural hematoma" | STABLE CLASS 2 |
| "No change in appearance of extends along the wall of the aorta" | STABLE CLASS 2 |
| "No change in appearance of consistent with a aortic wall ulceration/aortic dissection" | STABLE CLASS 2 |
| "No change in appearance of CONSISTENT WITH AORTIC ULCERATION/DISSECTION" | STABLE CLASS 2 |
| "No change in appearance of with intramural thrombus" | STABLE CLASS 2 |
| "No change in appearance of consistent with acute intramural hematoma" | STABLE CLASS 2 |
| "No change in appearance of likely associated intramural hematoma" | STABLE CLASS 2 |
| "No change in appearance of crescentic of intramural high density" | STABLE CLASS 2 |
| "No change in appearance of consistent with an acute intramural hemorrhage" | STABLE CLASS 2 |
| "No change in appearance of intramural leak of contrast" | STABLE CLASS 2 |
| "No change in appearance of medial displacement of the calcified intima" | STABLE CLASS 2 |
| "No change in appearance of into intramural hematoma" | STABLE CLASS 2 |
| "No change in appearance of with focal intramural dissection" | STABLE CLASS 2 |
| "No change in appearance of with associated intramural hemorrhage" | STABLE CLASS 2 |
| "No evidence of a new represents intramural hematoma" | STABLE CLASS 2 |
| "No evidence of a new is a intramural hematoma" | STABLE CLASS 2 |
| "No evidence of a new suggestive of intramural hematoma" | STABLE CLASS 2 |
| "No evidence of a new hemorrhage into the aortic wall" | STABLE CLASS 2 |
| "No evidence of a new HYPERDENSE CRESCENT SIGN" | STABLE CLASS 2 |
| "No evidence of a new represent an intramural hematoma" | STABLE CLASS 2 |
| "No evidence of a new crescentic region of increased attenuation" | STABLE CLASS 2 |
| "No evidence of a new increased crescentic attenuation" | STABLE CLASS 2 |
| "No evidence of a new aneurysm/pseudo aneurysm" | STABLE CLASS 2 |
| "No evidence of a new a focal intramural hematoma" | STABLE CLASS 2 |
| "No evidence of a new focal mural hematoma" | STABLE CLASS 2 |

| | |
|---|---|
| "No evidence of a new eccentric bulge" | STABLE CLASS 2 |
| "No evidence of a new intramural hemorrhage" | STABLE CLASS 2 |
| "No evidence of a new which suggests intramural hematoma" | STABLE CLASS 2 |
| "No evidence of a new is focal ectasia" | STABLE CLASS 2 |
| "No evidence of a new An anterior intramural hematoma" | STABLE CLASS 2 |
| "No evidence of a new extends along the wall of the aorta" | STABLE CLASS 2 |
| "No evidence of a new consistent with a aortic wall ulceration/aortic dissection" | STABLE CLASS 2 |
| "No evidence of a new CONSISTENT WITH AORTIC ULCERATION/DISSECTION" | STABLE CLASS 2 |
| "No evidence of a new with intramural thrombus" | STABLE CLASS 2 |
| "No evidence of a new consistent with acute intramural hematoma" | STABLE CLASS 2 |
| "No evidence of a new likely associated intramural hematoma" | STABLE CLASS 2 |
| "No evidence of a new crescentic of intramural high density" | STABLE CLASS 2 |
| "No evidence of a new consistent with an acute intramural hemorrhage" | STABLE CLASS 2 |
| "No evidence of a new intramural leak of contrast" | STABLE CLASS 2 |
| "No evidence of a new medial displacement of the calcified intima" | STABLE CLASS 2 |
| "No evidence of a new into intramural hematoma" | STABLE CLASS 2 |
| "No evidence of a new with focal intramural dissection" | STABLE CLASS 2 |
| "No evidence of a new with associated intramural hemorrhage" | STABLE CLASS 2 |
| "represents intramural hematoma which is unchanged" | STABLE CLASS 2 |
| "is a intramural hematoma which is unchanged" | STABLE CLASS 2 |
| "suggestive of intramural hematoma which is unchanged" | STABLE CLASS 2 |
| "hemorrhage into the aortic wall which is unchanged" | STABLE CLASS 2 |
| "HYPERDENSE CRESCENT SIGN which is unchanged" | STABLE CLASS 2 |
| "represent an intramural hematoma which is unchanged" | STABLE CLASS 2 |
| "crescentic region of increased attenuation which is unchanged" | STABLE CLASS 2 |
| "increased crescentic attenuation which is unchanged" | STABLE CLASS 2 |
| "aneurysm/pseudo aneurysm which is unchanged" | STABLE CLASS 2 |
| "a focal intramural hematoma which is unchanged" | STABLE CLASS 2 |
| "focal mural hematoma which is unchanged" | STABLE CLASS 2 |
| "eccentric bulge which is unchanged" | STABLE CLASS 2 |
| "intramural hemorrhage which is unchanged" | STABLE CLASS 2 |
| "which suggests intramural hematoma which is unchanged" | STABLE CLASS 2 |
| "is focal ectasia which is unchanged" | STABLE CLASS 2 |
| "An anterior intramural hematoma which is unchanged" | STABLE CLASS 2 |
| "extends along the wall of the aorta which is unchanged" | STABLE CLASS 2 |
| "consistent with a aortic wall ulceration/aortic dissection which is unchanged" | STABLE CLASS 2 |
| "CONSISTENT WITH AORTIC ULCERATION/DISSECTION which is unchanged" | STABLE CLASS 2 |
| "with intramural thrombus which is unchanged" | STABLE CLASS 2 |
| "consistent with acute intramural hematoma which is unchanged" | STABLE CLASS 2 |
| "likely associated intramural hematoma which is unchanged" | STABLE CLASS 2 |
| "crescentic of intramural high density which is unchanged" | STABLE CLASS 2 |
| "consistent with an acute intramural hemorrhage which is unchanged" | STABLE CLASS 2 |
| "intramural leak of contrast which is unchanged" | STABLE CLASS 2 |
| "medial displacement of the calcified intima which is unchanged" | STABLE CLASS 2 |
| "into intramural hematoma which is unchanged" | STABLE CLASS 2 |
| "with focal intramural dissection which is unchanged" | STABLE CLASS 2 |
| "with associated intramural hemorrhage which is unchanged" | STABLE CLASS 2 |
| "represents intramural hematoma has not increased in size" | STABLE CLASS 2 |
| "is a intramural hematoma has not increased in size" | STABLE CLASS 2 |
| "suggestive of intramural hematoma has not increased in size" | STABLE CLASS 2 |
| "hemorrhage into the aortic wall has not increased in size" | STABLE CLASS 2 |
| "HYPERDENSE CRESCENT SIGN has not increased in size" | STABLE CLASS 2 |
| "represent an intramural hematoma has not increased in size" | STABLE CLASS 2 |
| "crescentic region of increased attenuation has not increased in size" | STABLE CLASS 2 |
| "increased crescentic attenuation has not increased in size" | STABLE CLASS 2 |
| "aneurysm/pseudo aneurysm has not increased in size" | STABLE CLASS 2 |
| "a focal intramural hematoma has not increased in size" | STABLE CLASS 2 |
| "focal mural hematoma has not increased in size" | STABLE CLASS 2 |
| "eccentric bulge has not increased in size" | STABLE CLASS 2 |

| | |
|---|---|
| "intramural hemorrhage has not increased in size" | STABLE CLASS 2 |
| "which suggests intramural hematoma has not increased in size" | STABLE CLASS 2 |
| "is focal ectasia has not increased in size" | STABLE CLASS 2 |
| "An anterior intramural hematoma has not increased in size" | STABLE CLASS 2 |
| "extends along the wall of the aorta has not increased in size" | STABLE CLASS 2 |
| "consistent with a aortic wall ulceration/aortic dissection has not increased in size" | STABLE CLASS 2 |
| "CONSISTENT WITH AORTIC ULCERATION/DISSECTION has not increased in size" | STABLE CLASS 2 |
| "with intramural thrombus has not increased in size" | STABLE CLASS 2 |
| "consistent with acute intramural hematoma has not increased in size" | STABLE CLASS 2 |
| "likely associated intramural hematoma has not increased in size" | STABLE CLASS 2 |
| "crescentic of intramural high density has not increased in size" | STABLE CLASS 2 |
| "consistent with an acute intramural hemorrhage has not increased in size" | STABLE CLASS 2 |
| "intramural leak of contrast has not increased in size" | STABLE CLASS 2 |
| "medial displacement of the calcified intima has not increased in size" | STABLE CLASS 2 |
| "into intramural hematoma has not increased in size" | STABLE CLASS 2 |
| "with focal intramural dissection has not increased in size" | STABLE CLASS 2 |
| "with associated intramural hemorrhage has not increased in size" | STABLE CLASS 2 |

| | |
|---|---|
| "No evidence of an represents intramural hematoma" | NEG CLASS 2 |
| "No evidence of an is a intramural hematoma" | NEG CLASS 2 |
| "No evidence of an suggestive of intramural hematoma" | NEG CLASS 2 |
| "No evidence of an hemorrhage into the aortic wall" | NEG CLASS 2 |
| "No evidence of an HYPERDENSE CRESCENT SIGN" | NEG CLASS 2 |
| "No evidence of an represent an intramural hematoma" | NEG CLASS 2 |
| "No evidence of an crescentic region of increased attenuation" | NEG CLASS 2 |
| "No evidence of an increased crescentic attenuation" | NEG CLASS 2 |
| "No evidence of an aneurysm/pseudo aneurysm" | NEG CLASS 2 |
| "No evidence of an a focal intramural hematoma" | NEG CLASS 2 |
| "No evidence of an focal mural hematoma" | NEG CLASS 2 |
| "No evidence of an eccentric bulge" | NEG CLASS 2 |
| "No evidence of an intramural hemorrhage" | NEG CLASS 2 |
| "No evidence of an which suggests intramural hematoma" | NEG CLASS 2 |
| "No evidence of an is focal ectasia" | NEG CLASS 2 |
| "No evidence of an An anterior intramural hematoma" | NEG CLASS 2 |
| "No evidence of an extends along the wall of the aorta" | NEG CLASS 2 |
| "No evidence of an consistent with a aortic wall ulceration/aortic dissection" | NEG CLASS 2 |
| "No evidence of an CONSISTENT WITH AORTIC ULCERATION/DISSECTION" | NEG CLASS 2 |
| "No evidence of an with intramural thrombus" | NEG CLASS 2 |
| "No evidence of an consistent with acute intramural hematoma" | NEG CLASS 2 |
| "No evidence of an likely associated intramural hematoma" | NEG CLASS 2 |
| "No evidence of an crescentic of intramural high density" | NEG CLASS 2 |
| "No evidence of an consistent with an acute intramural hemorrhage" | NEG CLASS 2 |
| "No evidence of an intramural leak of contrast" | NEG CLASS 2 |
| "No evidence of an medial displacement of the calcified intima" | NEG CLASS 2 |
| "No evidence of an into intramural hematoma" | NEG CLASS 2 |
| "No evidence of an with focal intramural dissection" | NEG CLASS 2 |
| "No evidence of an with associated intramural hemorrhage" | NEG CLASS 2 |
| "No evidence of a represents intramural hematoma" | NEG CLASS 2 |
| "No evidence of a is a intramural hematoma" | NEG CLASS 2 |
| "No evidence of a suggestive of intramural hematoma" | NEG CLASS 2 |
| "No evidence of a hemorrhage into the aortic wall" | NEG CLASS 2 |
| "No evidence of a HYPERDENSE CRESCENT SIGN" | NEG CLASS 2 |
| "No evidence of a represent an intramural hematoma" | NEG CLASS 2 |
| "No evidence of a crescentic region of increased attenuation" | NEG CLASS 2 |
| "No evidence of a increased crescentic attenuation" | NEG CLASS 2 |
| "No evidence of a aneurysm/pseudo aneurysm" | NEG CLASS 2 |
| "No evidence of a a focal intramural hematoma" | NEG CLASS 2 |
| "No evidence of a focal mural hematoma" | NEG CLASS 2 |
| "No evidence of a eccentric bulge" | NEG CLASS 2 |
| "No evidence of a intramural hemorrhage" | NEG CLASS 2 |
| "No evidence of a which suggests intramural hematoma" | NEG CLASS 2 |
| "No evidence of a is focal ectasia" | NEG CLASS 2 |
| "No evidence of a An anterior intramural hematoma" | NEG CLASS 2 |
| "No evidence of a extends along the wall of the aorta" | NEG CLASS 2 |
| "No evidence of a consistent with a aortic wall ulceration/aortic dissection" | NEG CLASS 2 |
| "No evidence of a CONSISTENT WITH AORTIC ULCERATION/DISSECTION" | NEG CLASS 2 |
| "No evidence of a with intramural thrombus" | NEG CLASS 2 |
| "No evidence of a consistent with acute intramural hematoma" | NEG CLASS 2 |
| "No evidence of a likely associated intramural hematoma" | NEG CLASS 2 |
| "No evidence of a crescentic of intramural high density" | NEG CLASS 2 |
| "No evidence of a consistent with an acute intramural hemorrhage" | NEG CLASS 2 |
| "No evidence of a intramural leak of contrast" | NEG CLASS 2 |
| "No evidence of a medial displacement of the calcified intima" | NEG CLASS 2 |
| "No evidence of a into intramural hematoma" | NEG CLASS 2 |

| | |
|---|---|
| "No evidence of a with focal intramural dissection" | NEG CLASS 2 |
| "No evidence of a with associated intramural hemorrhage" | NEG CLASS 2 |
| "No evidence of represents intramural hematoma" | NEG CLASS 2 |
| "No evidence of is a intramural hematoma" | NEG CLASS 2 |
| "No evidence of suggestive of intramural hematoma" | NEG CLASS 2 |
| "No evidence of hemorrhage into the aortic wall" | NEG CLASS 2 |
| "No evidence of HYPERDENSE CRESCENT SIGN" | NEG CLASS 2 |
| "No evidence of represent an intramural hematoma" | NEG CLASS 2 |
| "No evidence of crescentic region of increased attenuation" | NEG CLASS 2 |
| "No evidence of increased crescentic attenuation" | NEG CLASS 2 |
| "No evidence of aneurysm/pseudo aneurysm" | NEG CLASS 2 |
| "No evidence of a focal intramural hematoma" | NEG CLASS 2 |
| "No evidence of focal mural hematoma" | NEG CLASS 2 |
| "No evidence of eccentric bulge" | NEG CLASS 2 |
| "No evidence of intramural hemorrhage" | NEG CLASS 2 |
| "No evidence of which suggests intramural hematoma" | NEG CLASS 2 |
| "No evidence of is focal ectasia" | NEG CLASS 2 |
| "No evidence of An anterior intramural hematoma" | NEG CLASS 2 |
| "No evidence of extends along the wall of the aorta" | NEG CLASS 2 |
| "No evidence of consistent with a aortic wall ulceration/aortic dissection" | NEG CLASS 2 |
| "No evidence of CONSISTENT WITH AORTIC ULCERATION/DISSECTION" | NEG CLASS 2 |
| "No evidence of with intramural thrombus" | NEG CLASS 2 |
| "No evidence of consistent with acute intramural hematoma" | NEG CLASS 2 |
| "No evidence of likely associated intramural hematoma" | NEG CLASS 2 |
| "No evidence of crescentic of intramural high density" | NEG CLASS 2 |
| "No evidence of consistent with an acute intramural hemorrhage" | NEG CLASS 2 |
| "No evidence of intramural leak of contrast" | NEG CLASS 2 |
| "No evidence of medial displacement of the calcified intima" | NEG CLASS 2 |
| "No evidence of into intramural hematoma" | NEG CLASS 2 |
| "No evidence of with focal intramural dissection" | NEG CLASS 2 |
| "No evidence of with associated intramural hemorrhage" | NEG CLASS 2 |
| "No intramural hematoma" | NEG CLASS 2 |
| "no intramural hemorrhage" | NEG CLASS 2 |

```
"saccular aneurysm"                                                              ANEURYSM
"ascending thoracic aortic aneurysm"                                             ANEURYSM
"ascending thoracic aorta aneurysm"                                              ANEURYSM
"descending thoracic aortic aneurysm"                                            ANEURYSM
"descending thoracic aorta aneurysm"                                             ANEURYSM
"abdominal aortic aneurysm"                                                      ANEURYSM
"abdominal aorta aneurysm"                                                       ANEURYSM
"ascending aortic aneurysm"                                                      ANEURYSM
"descending aortic anuerysm"                                                     ANEURYSM
"thoracoabdominal aortic aneurysm"                                               ANEURYSM
"aneurysmal dilation of ascending aorta"                                         ANEURYSM
"aneurysmal dilatation of the infrarenal abdominal aorta"                        ANEURYSM
"aneurysmal dilatation of the infrarenal aorta"                                  ANEURYSM
"infrarenal abdominal aortic aneurysm"                                           ANEURYSM
"infrarenal aortic aneurysm"                                                     ANEURYSM
"abdominal aortic aneurysm"                                                      ANEURYSM
"aorta measures 5 cm at the root"                                                ANEURYSM
"is a abdominal aortic aneurysm"                                                 ANEURYSM
"aneurysm of the abdominal aorta"                                                ANEURYSM
"ascending aortic aneurysm"                                                      ANEURYSM
"abdominal aortic aneurysm"                                                      ANEURYSM
"thoracic and abdominal aortic aneurysm"                                         ANEURYSM
"suprarenal aortic aneurysm"                                                     ANEURYSM
"aneurysm of the arch"                                                           ANEURYSM
"aneurysmal at the level of the main pulmonary artery"                           ANEURYSM
"Thoracoabdominal aortic aneurysm"                                               ANEURYSM
"aneurysm of the ascending aorta, arch and mid descending aorta"                 ANEURYSM
"infrarenal abdominal aortic aneurysm"                                           ANEURYSM
"thoracoabdominal aneurysm"                                                      ANEURYSM
"ectasia of the descending aorta"                                                ANEURYSM
"aneurysm of the suprarenal aorta"                                               ANEURYSM
"ANEURYSMAL DILATATION OF THE SUPRARENAL AORTA"                                  ANEURYSM
"prominence of aortic root"                                                      ANEURYSM
"infrarenal abdominal aortic aneurysm"                                           ANEURYSM
"proximal descending aorta are measures approximately 4"                         ANEURYSM
"is an infrarenal fusiform abdominal aortic aneurysm"                            ANEURYSM
"aneurysmal dilatation of the thoracic aorta"                                    ANEURYSM
"abdominal aortic aneurysm"                                                      ANEURYSM
"infrarenal atherosclerotic aortic aneurysm"                                     ANEURYSM
"The AAA"                                                                        ANEURYSM
"infrarenal aneurysm"                                                            ANEURYSM
"saccular aneurysm that originates just distal to the origin of the left subclavian artery"  ANEURYSM
"descending aorta measures 3"                                                    ANEURYSM
"aortic hiatus, the aorta measures 4"                                            ANEURYSM
"level of the superior mesenteric artery, the aorta measures 3"                  ANEURYSM
"At the level of the renal arteries, the aorta measures approximately 6"         ANEURYSM
"THORACIC ABDOMINAL AORTIC ANEURYSM"                                             ANEURYSM
"aortic hiatus, the aorta measures 4"                                            ANEURYSM
"THORACIC ABDOMINAL AORTIC ANEURYSM"                                             ANEURYSM
"aneurysm of the ascending thoracic aorta"                                       ANEURYSM
"DESCENDING THORACIC AORTIC ANEURYSM"                                            ANEURYSM
"infrarenal abdominal aortic aneurysm"                                           ANEURYSM
"ascending aorta is ectatic"                                                     ANEURYSM
"infrarenal AAA"                                                                 ANEURYSM
"ascending thoracic aorta is aneurysmal"                                         ANEURYSM
"Aneurysmal ascending thoracic aorta"                                            ANEURYSM
"infrarenal fusiform aortic aneurysm"                                            ANEURYSM
"ascending aorta measures 4"                                                     ANEURYSM
```

*abdominal aorta is aneurysmal*
*SACCULAR ANEURYSM OFF THE LEFT POSTEROLATERAL ASPECT OF THE AORTIC ROOT*
*below the renal arteries there is aneurysmal dilatation*
*aneurysmal dilatation of the infrarenal aorta*
*infrarenal aortic aneurysm*
*infrarenal abdominal aortic aneurysm*
*is a descending thoracic aortic aneurysm*
*Small abdominal aortic aneurysm*
*pararenal aortic aneurysm*
*aorta from the level of the IMA take off to the aortic graft is dilated*
*aorta from the level of the celiac axis take off to the aortic graft is dilated*
*aorta from the level of the SMA take off to the aortic graft is dilated*
*aneurysm of the descending thoracic aorta*
*juxtarenal abdominal aortic aneurysm*
*transverse aortic arch is a saccular aneurysm*
*saccular aneurysm arising from the aortic arch*
*infrarenal abdominal aortic aneurysm*
*ectasia of the thoracic aorta distal to take off of the left subclavian*
*infrarenal abdominal aortic aneurysm*
*descending thoracic aorta aneurysm*
*infrarenal abdominal aneurysm*
*descending thoracic aortic aneurysm*
*infrarenal abdominal aortic aneurysm*
*descending thoracic aorta becomes aneurysmal*
*hiatus the aorta measures 4*
*ectasia of the proximal infrarenal aorta*

ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM
ANEURYSM

FIGURE 21B

| | |
|---|---|
| *thoracoabdominal aortic aneurysm* | NEW DES TAA |
| *thoracoabdominal aortic aneurysm* | NEW AAA |
| *aneurysmal dilation of ascending aorta* | NEW ASC TAA |
| *aneurysmal dilatation of the infrarenal abdominal aorta* | NEW AAA |
| *aneurysmal dilatation of the infrarenal aorta* | NEW AAA |
| *infrarenal abdominal aortic aneurysm* | NEW AAA |
| *infrarenal aortic aneurysm* | NEW AAA |
| *abdominal aortic aneurysm* | NEW AAA |
| *aorta measures ???? at the root* | NEW ASC TAA |
| *aorta measures ??? at the root* | NEW ASC TAA |
| *aorta measures ?????? at the root* | NEW ASC TAA |
| *aorta measures ????? at the root* | NEW ASC TAA |
| *is a abdominal aortic aneurysm* | NEW AAA |
| *aneurysm of the abdominal aorta* | NEW AAA |
| *ascending aortic aneurysm* | NEW ASC TAA |
| *abdominal aortic aneurysm* | NEW AAA |
| *thoracic and abdominal aortic aneurysms* | NEW DES TAA |
| *thoracic and abdominal aortic aneurysms* | NEW AAA |
| *suprarenal aortic aneurysm* | NEW AAA |
| *aneurysm of the arch* | NEW ASC TAA |
| *aneurysmal at the level of the main pulmonary artery* | NEW DES TAA |
| *Thoracoabdominal aortic aneurysm* | NEW AAA |
| *aneurysm of the ascending aorta, arch and mid descending aorta* | NEW ASC TAA |
| *aneurysm of the ascending aorta, arch and mid descending aorta* | NEW DES TAA |
| *aneurysm of the ascending aorta, arch and mid descending aorta* | NEW AAA |
| *infrarenal abdominal aortic aneurysm* | NEW AAA |
| *thoracoabdominal aneurysm* | NEW AAA |
| *thoracoabdominal aneurysm* | NEW DES TAA |
| *ectasia of the descending aorta* | NEW DES TAA |
| *ectasia of the descending aorta* | NEW AAA |
| *aneurysm of the suprarenal aorta* | NEW AAA |
| *ANEURYSMAL DILATATION OF THE SUPRARENAL AORTA* | NEW AAA |
| *prominence of aortic root* | NEW ASC TAA |
| *infrarenal abdominal aortic aneurysm* | NEW AAA |
| *proximal descending aorta are measures approximately* | NEW DES DIL |
| *is an infrarenal fusiform abdominal aortic aneurysm* | NEW AAA |
| *aneurysmal dilatation of the thoracic aorta* | NEW DES TAA |
| *aneurysmal dilatation of the thoracic aorta* | NEW ASC TAA |
| *abdominal aortic aneurysm* | NEW AAA |
| *infrarenal atherosclerotic aortic aneurysm* | NEW AAA |
| *The AAA* | NEW AAA |
| *infrarenal aneurysm* | NEW AAA |
| *saccular aneurysm that originates just distal to the origin of the left subclavian artery* | NEW DES TAA |
| *descending aorta measures* | NEW AAA |
| *aortic hiatus, the aorta measures ?* | NEW DES TAA |
| *level of the superior mesenteric artery, the aorta measures* | NEW AAA |
| *At the level of the renal arteries, the aorta measures approximately ?* | NEW AAA |
| *THORACIC ABDOMINAL AORTIC ANEURYSM* | NEW AAA |
| *aortic hiatus, the aorta measures ?* | NEW AAA |
| *THORACIC ABDOMINAL AORTIC ANEURYSM* | NEW DES TAA |
| *aneurysm of the ascending thoracic aorta* | NEW ASC TAA |
| *DESCENDING THORACIC AORTIC ANEURYSM* | NEW DES TAA |
| *infrarenal abdominal aortic aneurysm* | NEW AAA |
| *ascending aorta is ectatic* | NEW ASC DIL |
| *infrarenal AAA* | NEW AAA |
| *ascending thoracic aorta is aneurysmal* | NEW ASC TAA |

| | | |
|---|---|---|
| *Aneurysmal ascending thoracic aorta* | NEW ASC TAA | ~369 |
| *infrarenal fusiform aortic aneurysm* | NEW AAA | |
| *ascending aorta measures ?* | NEW ASC DIL | |
| *infrarenal aortic aneurysm* | NEW AAA | |
| *infrarenal abdominal aortic aneurysm* | NEW AAA | |
| *abdominal aorta is aneurysmal* | NEW AAA | |
| *SACCULAR ANEURYSM OFF THE LEFT POSTEROLATERAL ASPECT OF THE AORTIC ROOT* | NEW ASC TAA | |
| *infrarenal abdominal aortic aneurysm* | NEW AAA | |
| *infrarenal AAA* | NEW AAA | |
| *below the renal arteries there is aneurysmal dilatation* | NEW AAA | |
| *aneurysmal dilatation of the infrarenal aorta* | NEW AAA | |
| *infrarenal aortic aneurysm* | NEW AAA | |
| *infrarenal abdominal aortic aneurysm* | NEW AAA | |
| *is a descending thoracic aortic aneurysm* | NEW DES TAA | |
| *Small abdominal aortic aneurysm* | NEW AAA | |
| *pararenal aortic aneurysm* | NEW AAA | |
| *aorta from the level of the SMA take off to the aortic graft is dilated* | NEW AAA | |
| *aneurysm of the descending thoracic aorta* | NEW DES TAA | |
| *juxtarenal abdominal aortic aneurysm* | NEW AAA | |
| *transverse aortic arch is a saccular aneurysm* | NEW DES TAA | |
| *saccular aneurysm arising from the aortic arch* | NEW DES TAA | |
| *infrarenal abdominal aortic aneurysm* | NEW AAA | |
| *ectasia of the thoracic aorta distal to take off of the left subclavian* | NEW DES TAA | |
| *infrarenal abdominal aortic aneurysm* | NEW AAA | |
| *descending thoracic aorta aneurysm* | NEW DES TAA | |
| *infrarenal abdominal aneurysm* | NEW AAA | |
| *descending thoracic aortic aneurysm* | NEW DES TAA | |
| *infrarenal abdominal aortic aneurysm* | NEW AAA | |
| *descending thoracic aorta becomes aneurysmal* | NEW DES TAA | |
| *hiatus the aorta measures  ?* | NEW AAA | |
| *hiatus the aorta measures  ???* | NEW AAA | |
| *ectasia of the proximal infrarenal aorta* | NEW AAA | |
| *ascending thoracic aortic aneurysm* | NEW ASC TAA | |
| *ascending thoracic aorta aneurysm* | NEW ASC TAA | |
| *descending thoracic aortic aneurysm* | NEW DES TAA | |
| *descending thoracic aorta aneurysm* | NEW DES TAA | |
| *abdominal aortic aneurysm* | NEW AAA | |
| *abdominal aorta aneurysm* | NEW AAA | |
| *ascending aortic anuerysm* | NEW ASC TAA | |
| *descending aortic anuerysm* | NEW DES TAA | |
| *thoracoabdominal aortic aneurysm* | NEW DES TAA | |
| *descending aortic anuerysm* | NEW AAA | |
| *thoracoabdominal aortic aneurysm* | NEW AAA | |

FIGURE 23B

Given MDCT Validation Data ~450

| Category | + Case | - Case | Totals |
|---|---|---|---|
| + MDCT | 67 | 0 | 67 |
| Indeterm MDCT | 0 | 0 | 0 |
| - MDCT | 1 | 304 | 305 |
| Totals | 68 | 304 | 372 |

~460

| Category | + Case | - Case | Totals | Pre-test Probab. | Pre-test Odds | LR | Post-test Odds | Post-test Probab. |
|---|---|---|---|---|---|---|---|---|
| + MDCT | 67 | 1 | 68 | 25% | 0.333 | 300.51 | 100.06 | 0.99 |
| Interm MDCT | 0 | 1 | 1 | --- | --- | 0 | 0 | 0 |
| - MDCT | 1 | 304 | 305 | --- | --- | 0.018 | 0.005 | 0.004 |
| Totals | 68 | 305 | 374 | --- | --- | 1 | 0.333 | 0.249 |

FIGURE 30

FIGURE 31

OPTIMAL TEST CHOICE

- Consider a lab test that costs $10
- Sensitivity = 85%
- Specificity = 90%

~500

| | Cause B | Cause A | Probability | Probab of B | Probab of A |
|---|---|---|---|---|---|
| + Test | x 0.05 = 0.0425 | x 0.95 = 0.095 | = 0.1375 | TP/TP + FP = 0.31 | 0.69 |
| − Test | x 0.05 = | x 0.95 | = 0.8625 | FN/FN+TN = 0.0087 | 0.9913 |
| | Cause B | Cause A | Cost | Decision | |
| Tx | $50 + $10 x 0.31 | $55 + $10 x 0.69 | $63.45 | Cheaper | |
| No Tx | $624 + $10 x 0.31 | $5 + $10 x 0.69 | $206.33 | | |
| | Cause B | Cause A | Cost | Decision | |
| Tx | $50 + $10 x 0.0087 | $55 + $10 x 0.9913 | $64.96 | | |
| No Tx | $624 + $10 0.0087 | $5 + $10 x 0.9913 | $20.38 | Cheaper | |

Expected Value of Test = Cheapest Decision for each Test Result x Probability
Expected Value of First Test = ($63.45 x 0.1375) + ($20.38 x 0.8625) = $26.31
Expected Value of no test utilization = $35.95

FIGURE 32A

OPTIMAL TEST CHOICE

- Cost = $30
- Sensitivity = 100%
- Specificity = 100%

| | Cause B | Cause A | Probability | Probab of B | Probab of A |
|---|---|---|---|---|---|
| +Test | x 0.05 = 0.05 | x 0.95 = 0 | = 0.05 | TP/TP+FP = 1 | 0 |
| −Test | x 0.05 = 0 | x 0.95 = 0.95 | = 0.95 | FN/FN+TN = 0 | 1 |

| | Cause B | Cause A | Cost | Decision |
|---|---|---|---|---|
| Tx | $50 + $30 x 1 | $55 + $30 x 0 | $80 | Cheaper |
| No Tx | $624 + $30 x 1 | $5 + $30 x 0 | $654 | |

| | Cause B | Cause A | Cost | Decision |
|---|---|---|---|---|
| Tx | $50 + $30 x 0 | $55 + $30 x 1 | $85 | |
| No Tx | $624 + $30 x 0 | $5 + $30 x 1 | $35 | Cheaper |

~510

Expected Value of second test = (0.05 x $80) + (0.95 x $35) = $37.25
Expected Value of first test = $26.31
Expected Value of no test utilization = $35.95
Note first test remains optimal according to expected value If the second test was free of cost, then the expected value of the second test = $7.25
Likely turn free second test into an Opportunity Loss where no test utilization = $28.70
~ most you should pay for a perfect test as it was an Opportunity Loss

FIGURE 32B

OPTIMAL TEST CHOICE

- Cost = $1
- Sensitivity = 60%
- Specificity = 60%

| | Cause B | Cause A | Probability | Probab of B | Probab of A |
|---|---|---|---|---|---|
| | | | | TP/TP+FP = 0.073 | 0.927 |
| +Test | x 0.05 = 0.03 | x 0.95 = 0.38 | = 0.41 | | |
| −Test | x 0.05 = 0.02 | x 0.95 = 0.57 | = 0.59 | FN/FN+TN = 0.033 | 0.966 |
| | Cause B | Cause A | Cost | | |
| Tx | $50 + $1 x 0.073 | $55 + $1 x 0.927 | $60.65 | Decision | |
| No Tx | $624 + $1 x 0.073 | $5 + $1 x 0.927 | $51.18 | Cheaper | |
| | Cause B | Cause A | Cost | | |
| Tx | $50 + $1 x 0.033 | $55 + $1 x 0.966 | $55.77 | Decision | |
| No Tx | $624 + $1 x 0.033 | $5 + $1 x 0.966 | $26.42 | Cheaper | |

Expected Value of third test = (0.41 x $51.18) + (0.59 x $26.42) = $36.57
Expected Value of second test = $37.25
Expected Value of first test = $26.31
Expected Value of no test utilization = $35.95

Optimal test choice based on Expected Value is first test

FIGURE 32C

METHOD FOR SEARCHING A TEXT (OR ALPHANUMERIC STRING) DATABASE, RESTRUCTURING AND PARSING TEXT DATA (OR ALPHANUMERIC STRING), CREATION/APPLICATION OF A NATURAL LANGUAGE PROCESSING ENGINE, AND THE CREATION/APPLICATION OF AN AUTOMATED ANALYZER FOR THE CREATION OF MEDICAL REPORTS

PRIOR PROVISIONAL APPLICATION

The present application claims the benefit of U.S. provisional application Ser. No. 61/790,817 filed Mar. 15, 2013, the disclosure of which is hereby incorporated by reference.

FIELD OF THE INVENTION

The present invention relates to a method that allows for the comprehensive reading and understanding of radiology, clinical, pathology, and laboratory reports, and, more particularly, to a sequential series of methods for optimization of keyword searches within a keyword searchable text (or alphanumeric string) database, restructuring and parsing of the data, the creation and application of a natural language processing engine, and the creation and application of an automated analyzer all for production of easily read and comprehended medical reports.

BACKGROUND OF THE INVENTION

The potential of role of informatics in the future of medicine is immense. Medical leaders have voiced concern and the emerging idea of performance indicators for radiology departments will soon become the standard of practice. These indicators will serve to gauge the performance of licensed radiology departments, but they will provide no quantification of the work upstream in the medical pipeline: proper utilization of radiological imaging. Few individuals have realized this deficit in gauging radiology; thus, the research in this area has been limited.

The only factors that can be used to gauge utilization of radiology are economic and statistical. Intuitively it would seem an economic based quantification system would be more pragmatic. However, a gauge based on imaging costs and cost-effectiveness is impractical as it cannot be extrapolated across institutions readily. One whole body computed tomography (CT) examination at a particular institution may be billed as a single unit, yet the same exam may be broken into separate billing codes for chest, abdomen, and pelvis at another institution. Further, the assignment of relative value units (RVU) to individual products or services and allocation of overhead costs may vary between institutions. Thus, using an economic based quantification system to gauge radiology utilization across institutions and departments is impractical, inefficient, and inaccurate.

In contrast, gauging the utilization of radiology by a statistical quantification system lacks the negative factors found in an economic based system. Specifically, gauging the utilization of radiology by positive scan rates bypasses the differences created by variations in billing codes seen in different institutions. For example, a positive aortic dissection multi-detector CT (MDCT) in one Radiology Department would be considered a positive aortic dissection MDCT in a second Radiology Department given the proper imaging findings. Therefore, quantifying radiology utilization through imaging protocol positive scan rates is the only viable method to compare use across institutions and departments objectively. However, economic based imaging gauges can serve a role for internal or departmental analysis.

Once normalized radiology utilization gauges are created, further steps into normalizing and then comparing other downstream metrics becomes possible.

SUMMARY OF THE INVENTION

Each imaging protocol is optimized for a given diagnosis; therefore, each examination performed under a given protocol can be defined as positive or negative, and sometimes indeterminate, for a particular diagnosis. The resulting positive scan rate serves as a surrogate marker for the utilization, or use, of that particular diagnostic imaging protocol. Complications arise when alternative diagnoses are identified by an imaging protocol not designed for that particular diagnosis. Fortunately, this complication can be dealt with by creating a separate overall positive scan rate for all significant diagnoses identified.

A separate limitation in gauging radiology utilization by positive scan rates exists from the standpoint of appropriateness criteria. Since the initial investigation was retrospective only, no conclusions can be inferred regarding the satisfaction of clinical appropriateness criteria set forth by the American College of Radiology (ACR). However, the literature suggests the criteria are only sporadically used in the clinical setting, partly negating the argument that this be considered a limitation of the prior investigation. Further, positive scan rates may also serve as potential surrogate retrospective markers in place of prospective surveys of the use of appropriateness criteria.

The current operational limitation to gauging the utilization of radiology through positive scan rates is that the research necessary to properly identify the positive scan rate for a given imaging protocol needs to be identified with relative ease and accuracy. Currently, these two requirements have not been met. To date, accurate imaging positivity rates need to be identified through laborious and time-intensive research. The optimal method for identification of imaging positive scan rates has yet to be conceived.

The first objective to create an optimal method was to build a high quality database of non-traumatic emergency (ER) patients with suspected aortic dissection examined by multi-detector computed tomography (MDCT) during the years 2002 (403 cases), 2003 (579 cases), and 2004 (660 cases). Initially, the investigation served to define the trend in the aortic dissection protocol MDCT positive scan rate during the study period. Later, after the database was complete, it served as the reference standard for comparison for further work in gauging radiology utilization through automation.

The future of gauging radiology utilization will require management of large databases derived from multiple radiology departments. The original goal was to turn the investigation (from 2005 and 2006) into an automated software-based data analysis and computational tool for identifying imaging protocol positive scan rates. Given the sheer volume of data necessary to generate adequate reliability, the potential for a properly constructed procedure for interpretation analysis is immense. Once constructed, what originally took months to analyze would take less than a few minutes. After the database was completed and the natural language processing (NLP) decoding engine method accuracy was assured, subsequent investigation focused on creating increased levels of automation at the last/analytical stage.

The following methods for a new 2002, 2003, and 2004 aortic dissection protocol MDCT database were invented and validated (in November 2005 and December 2005) against the previous aortic dissection protocol MDCT database of 2002 and 2003 cases as published in the radiology literature (1). All subsequent work during the intervening years from 2006 to 2013 focused on invention of new and efficient formulas to automatically analyze the created database and other similar databases: the Automated Analyzer (unpublished databases). The methods described are equally applicable to pathology, clinical, and laboratory reports.

From a broad perspective, looking at the additive effect of Stages 1-4, the results transform text data (or alphanumeric string) from radiology, pathology, clinical, and laboratory reports into natural language understanding and automated analytics.

BRIEF DESCRIPTION OF THE DRAWINGS

FIG. 8 is an enlarged simple example screen shot of parsed database header terms for basic understanding.

FIG. 12 is an example of a screen shot of a NLP engine table (dissection protocol), according to an embodiment of the present invention.

FIG. 13A is an example of a screen shot of a NLP engine table (POSAAD), according to an embodiment of the present invention.

FIG. 13B is an example of a screen shot of a NLP engine table (POSAAD, cont'd.), according to an embodiment of the present invention.

FIG. 13C is an example of a screen shot of a NLP engine table (POSAAD, cont'd.), according to an embodiment of the present invention.

FIG. 13D is an example of a screen shot of a NLP engine table (POSAAD, cont'd.), according to an embodiment of the present invention.

FIG. 14A is an example of a screen shot of a NLP engine table (Type A and B), according to an embodiment of the present invention.

FIG. 15A is an example of a screen shot of a NLP engine table (Type 1, 2, and 3), according to an embodiment of the present invention.

FIG. 15B is an example of a screen shot of a NLP engine table (Type 1, 2, and 3, cont'd.), according to an embodiment of the present invention.

FIG. 16 is an example of a screen shot of a NLP engine table (CLASS 1), according to an embodiment of the present invention.

FIG. 17A is an example of a screen shot of a NLP engine table (NEG CLASS 1) where NEG refer to Negative, according to an embodiment of the present invention.

FIG. 17B is an example of a screen shot of a NLP engine table (NEG CLASS 1, cont'd.), according to an embodiment of the present invention.

FIG. 17C is an example of a screen shot of a NLP engine table (NEG CLASS 1, cont'd.), according to an embodiment of the present invention.

FIG. 18 is an example of a screen shot of a NLP engine table (CLASS 2), according to an embodiment of the present invention.

FIG. 19A is an example of a screen shot of a NLP engine table (STABLE CLASS 2), according to an embodiment of the present invention.

FIG. 19B is an example of a screen shot of a NLP engine table (STABLE CLASS 2, cont'd.), according to an embodiment of the present invention.

FIG. 19C is an example of a screen shot of a NLP engine table (STABLE CLASS 2, cont'd.), according to an embodiment of the present invention.

FIG. 19D is an example of a screen shot of a NLP engine table (STABLE CLASS 2, cont'd.), according to an embodiment of the present invention.

FIG. 19E is an example of a screen shot of a NLP engine table (STABLE CLASS 2, cont'd.), according to an embodiment of the present invention.

FIG. 19F is an example of a screen shot of a NLP engine table (STABLE CLASS 2, cont'd.), according to an embodiment of the present invention.

FIG. 19G is an example of a screen shot of a NLP engine table (STABLE CLASS 2, cont'd.), according to an embodiment of the present invention.

FIG. 20A is an example of a screen shot of a NLP engine table (NEG CLASS 2), according to an embodiment of the present invention.

FIG. 20B is an example of a screen shot of a NLP engine table (NEG CLASS 2, cont'd.), according to an embodiment of the present invention.

FIG. 21A is an example of a screen shot of a NLP engine table (ANEURYSM), according to an embodiment of the present invention.

FIG. 21B is an example of a screen shot of a NLP engine table (ANEURYSM, cont'd.), according to an embodiment of the present invention.

FIG. 23A is an example of a screen shot of a NLP engine table (ANEURYSM LOCATIONS), according to an embodiment of the present invention.

FIG. 23B is an example of a screen shot of a NLP engine table (ANEURYSM LOCATIONS, cont'd.), according to an embodiment of the present invention.

FIG. 30 are examples of tables showing how imaging protocol verification can be applied, according to an embodiment of the present invention.

FIG. 31 are examples of tables showing how a loss matrix and opportunity loss matrix can be applied to decision making, according to an embodiment of the present invention.

FIG. 32A is an example table showing how a loss matrix can be applied to optimal choice decision making for test utilization (first test), according to an embodiment of the present invention.

FIG. 32B is an example table showing how a loss matrix can be applied in optimal choice decision making for test utilization (second test), according to an embodiment of the present invention.

FIG. 32C is an example table showing how an opportunity loss matrix can be applied to optimal choice decision making for test utilization (third test), according to an embodiment of the present invention.

DETAILED DESCRIPTION

FIGS. 1 through 29 illustrate a sequential series of methods (Stages 1 through 4) (140, 150, 160, 170, 175) and apparatus (Automated Analyzer client 110 and associated server 120) for searching a text (or alphanumeric string) database, restructuring and parsing text data (or alphanumeric string), creation/application of a natural language processing engine, and the creation/application of an automated analyzer to collectively achieve natural language understanding and automated analytics.

Figure 2:
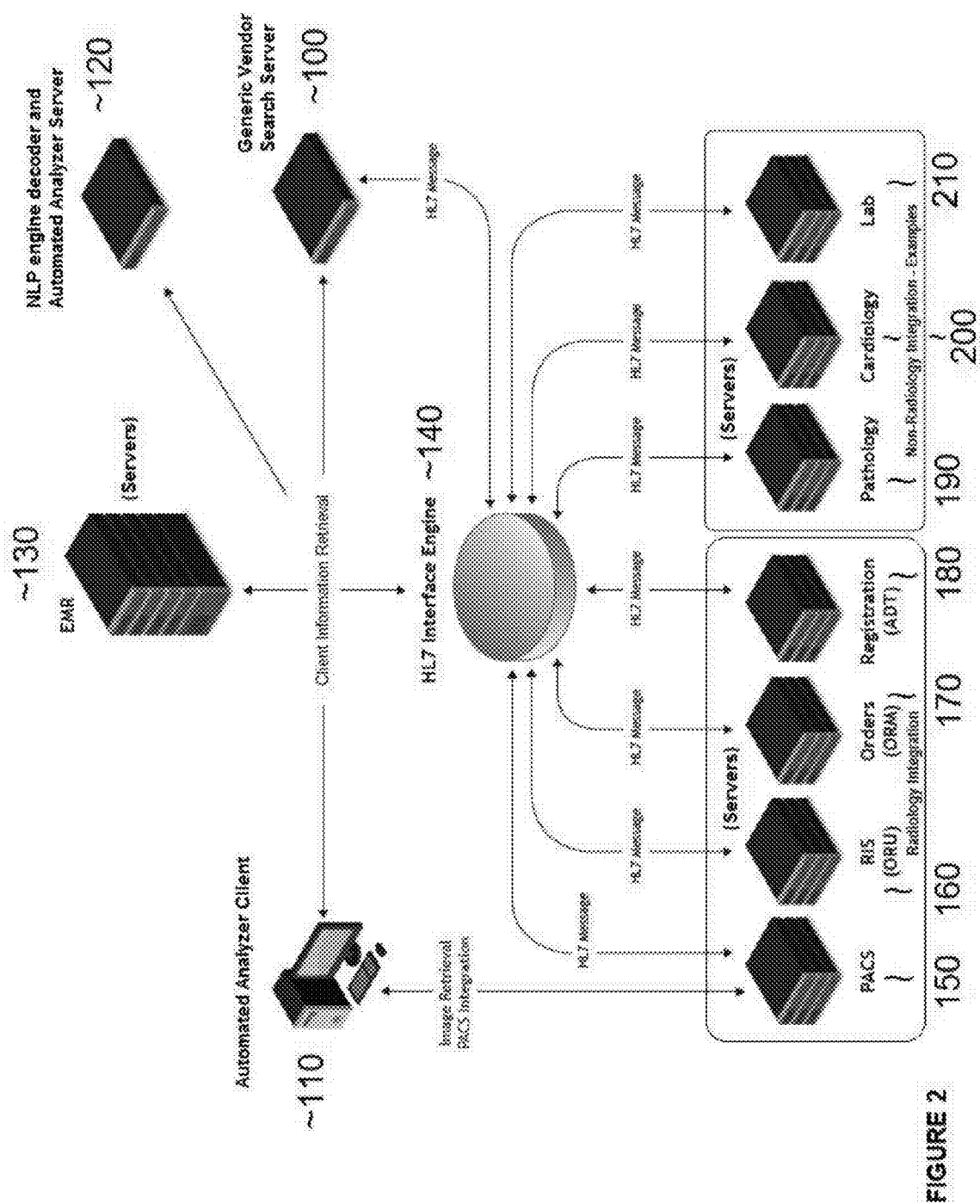
FIG. 2 is an illustration of a diagram showing the relative positions of physical hardware related to the software/method stages and the data flow environment within standard hospital Health Level 7 (HL7) interface architecture, according to an embodiment of the present invention.

Referring now to FIG. 2, the global or broad perspective of standard hospital Health Level 7 (HL7) interface architecture is shown. As can be seen, the Automated Analyzer Client 110 and the natural language processing (NLP) engine decoder and Automated Analyzer Server 120 process text data (or alphanumeric string) results from an indexed generic vendor search server 100. All hospital data flows via HL7 messages from individual servers, as an example PACS 150, to a central HL7 interface engine 140, and then is retrieved and viewed from local clients, as an example an electronic medical record (EMR, or electronic health record EHR) 130. Source servers employed during the present invention include PACS 150, RIS 160, ORM 170, ADT 180, Pathology 190, Cardiology 200, and Lab 210.

Figure 1:
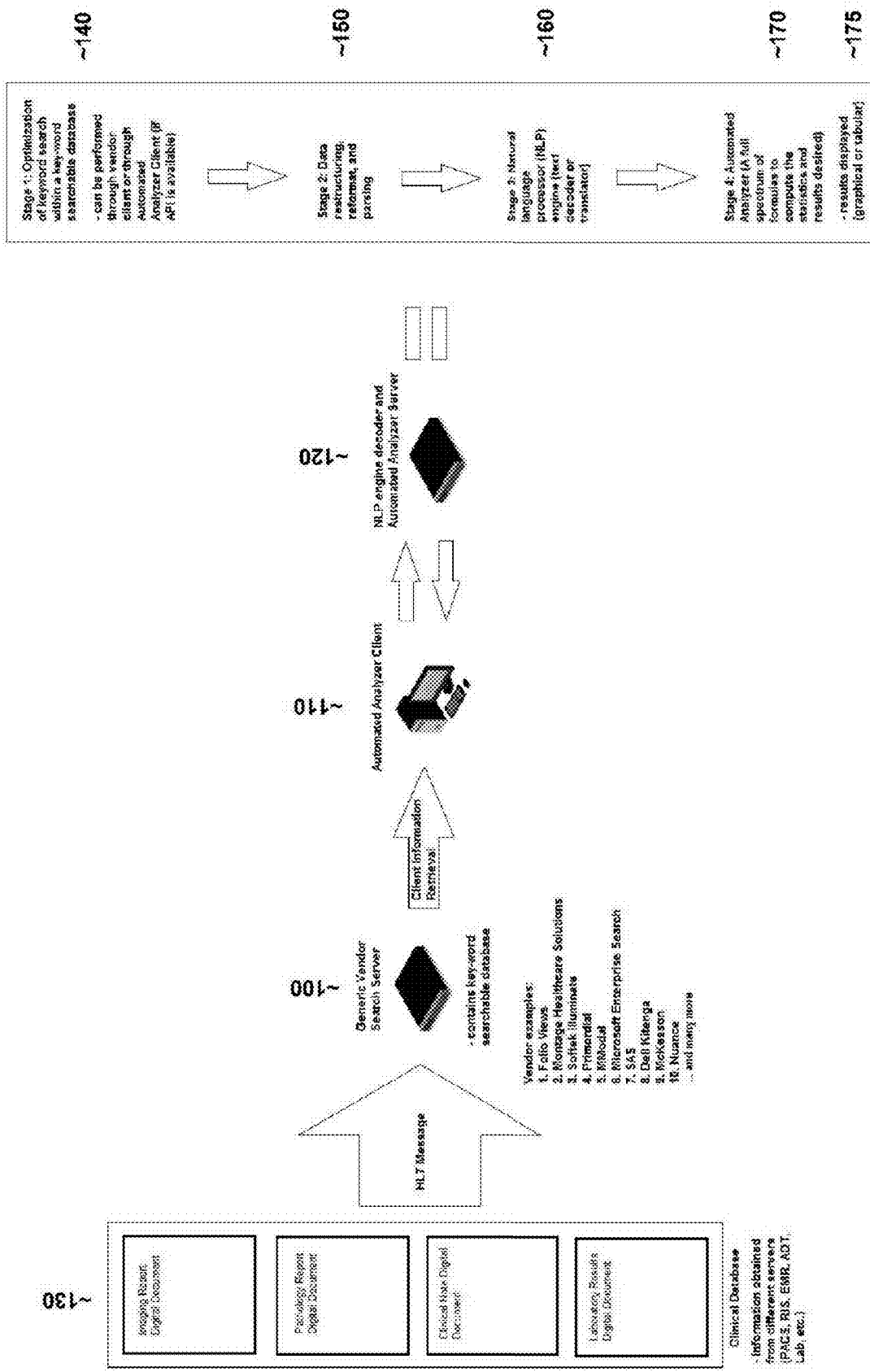
FIG. 1 is an illustration of a diagram showing the software architecture/method stages process flow relative to a standard clinical database, according to an embodiment of the present invention.

Referring now to FIG. 1, the process flow of the invented software architecture/methods stages can be seen. As examples, four source reports are contained within four individual servers (refer to FIG. 2, PACS 150, Pathology 190, EMR 130, and Lab 210), here collectively represented as a clinical database 130. The reports are transmitted by HL7 messages to a generic vendor search server 100 and then retrieved by the Automated Analyzer Client 110. Using the Automated Analyzer Client 110, the NLP engine decoder and Automated Analyzer Server 120 is instructed to execute Stages 1 through 4 (140, 150, 160, 170, and 175) on a given database. The results of the automated analysis are then viewed from the Automated Analyzer Client 110.

Figure 3:
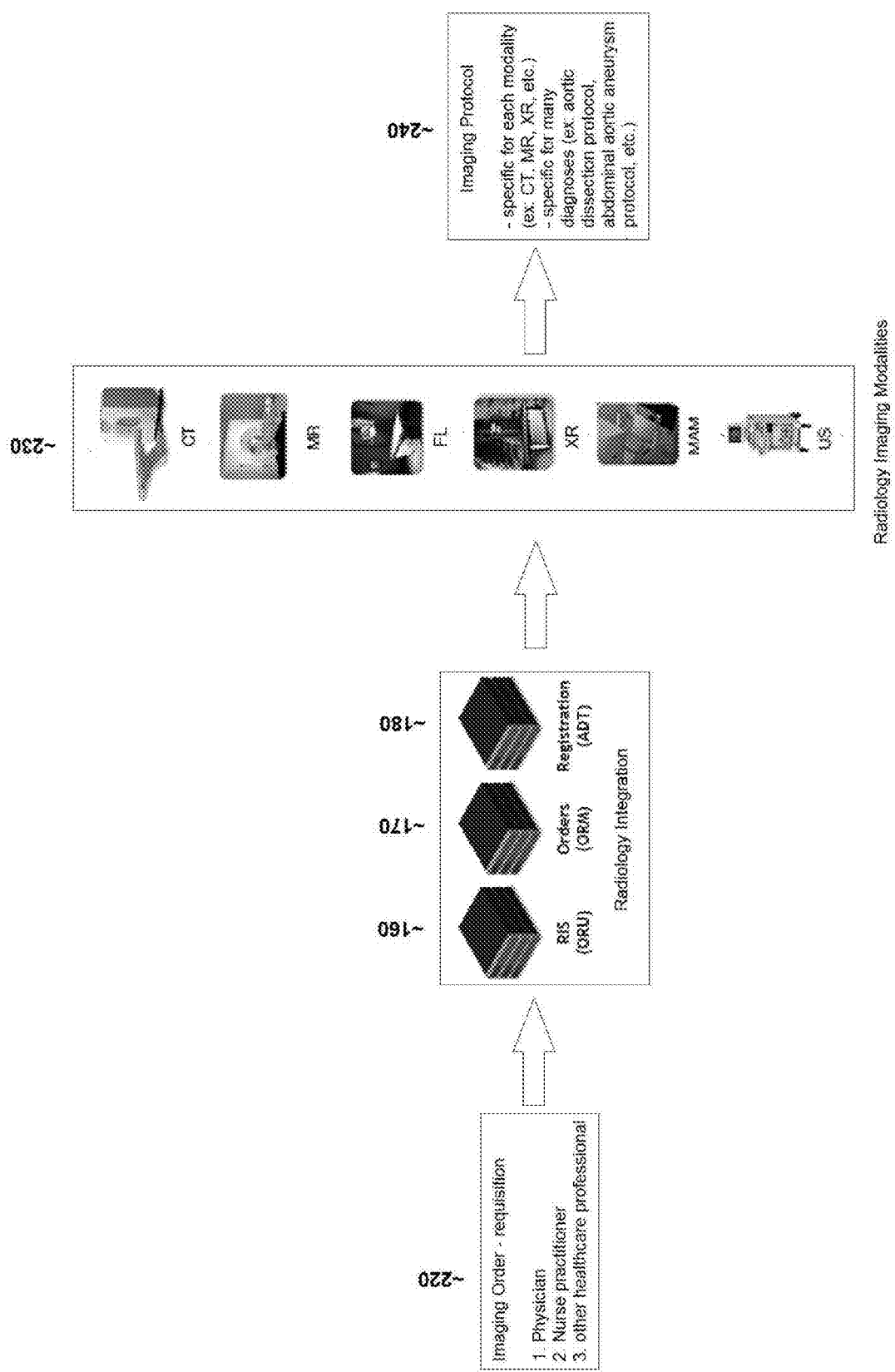
FIG. 3 is an illustration of a diagram showing standard imaging workflow, from imaging order to imaging protocol, according to an embodiment of the present invention.

Referring now to FIG. 3, a standard imaging workflow from imaging order 220 to imaging protocol 240 is shown. The imaging order 220 originates from a diagnostic consideration based on clinical decision making by a physician, nurse practitioner, or other healthcare professional. The imaging order 220 is then received and processed by several integrated radiology servers (PACS 160, ORM 170, and ADT 180). Next, the requested radiology imaging modality 230 appointment is requested, further processing occurs, and based on the imaging order 220 and imaging modality 230 an initial imaging protocol 240 is planned. Each imaging protocol 240 is designed to be specific to a modality and specific to a given diagnostic consideration, or a very narrow range of diagnostic possibilities.

Figure 4:
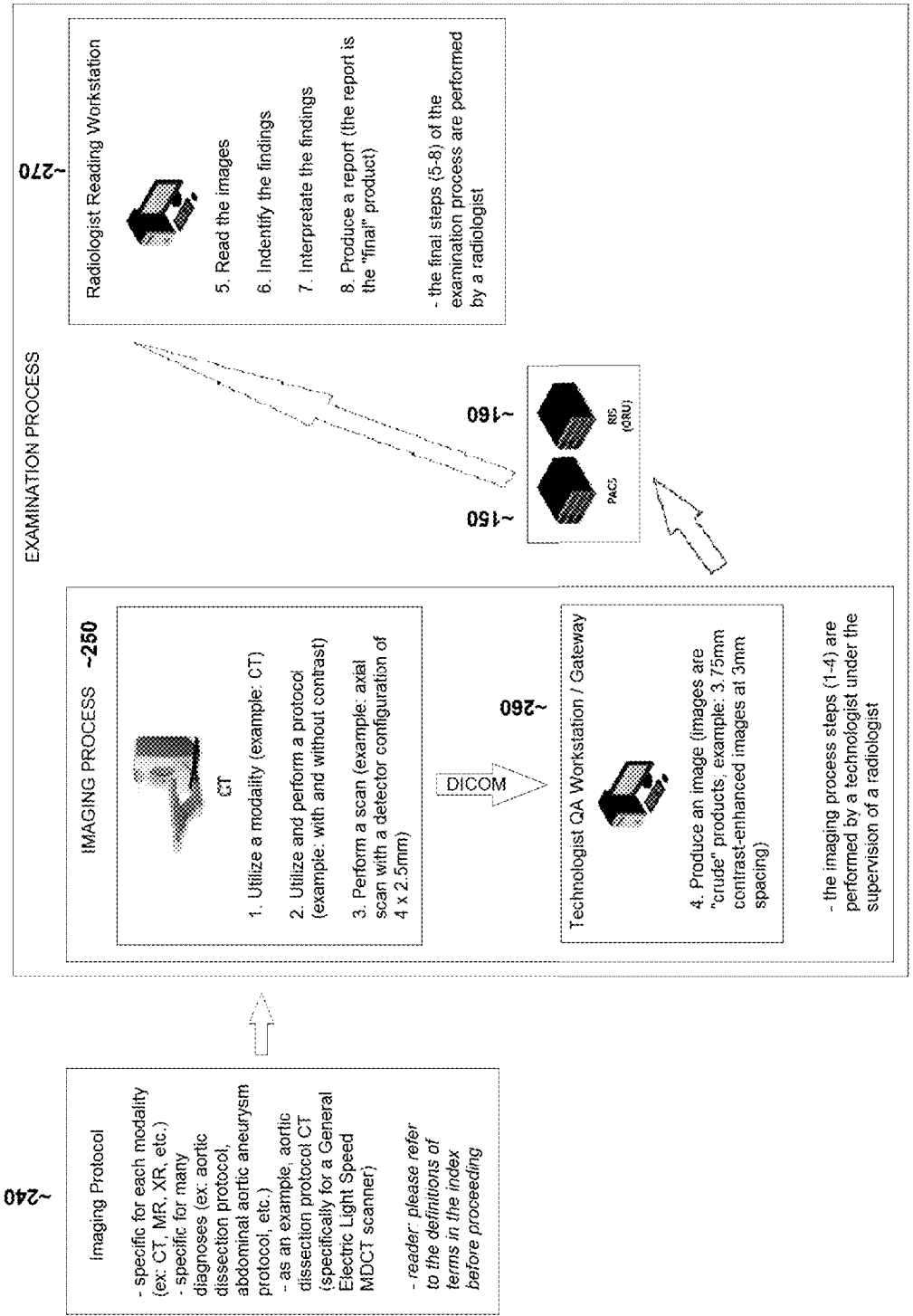
FIG. 4 is an illustration of a diagram showing standard imaging workflow, from imaging protocol to imaging report production, according to an embodiment of the present invention.

Referring now to FIG. 4, the initial imaging protocol 240 planned prompts further downstream workflow. First, the requested imaging modality 230 (FIG. 3) appointment is scheduled, the appropriate technician(s) is alerted, and further processing occurs, such as confirmation that the appropriate imaging modality 230 (FIG. 3) and imaging protocol 240 is planned given the initial diagnostic consideration. Once confirmed, the examination process proceeds. First, the imaging process 250 proceeds with the use of the given modality, then the imaging protocol is performed, and then a scan is performed. Next, the Digital Imaging and Communications in Medicine (DICOM) data is sent to a technologist QA workstation/gateway 260 where an image(s) is produced. After technologist processing, the images are sent to PACS 150 and RIS 160. Finally, the radiologist reading workstation 270 displays the resulting images for reading, finding identification, finding interpretation, and report production. All steps in the entire examination process are either directly performed or supervised by a radiologist (physician).

Stage 1

Figure 5:
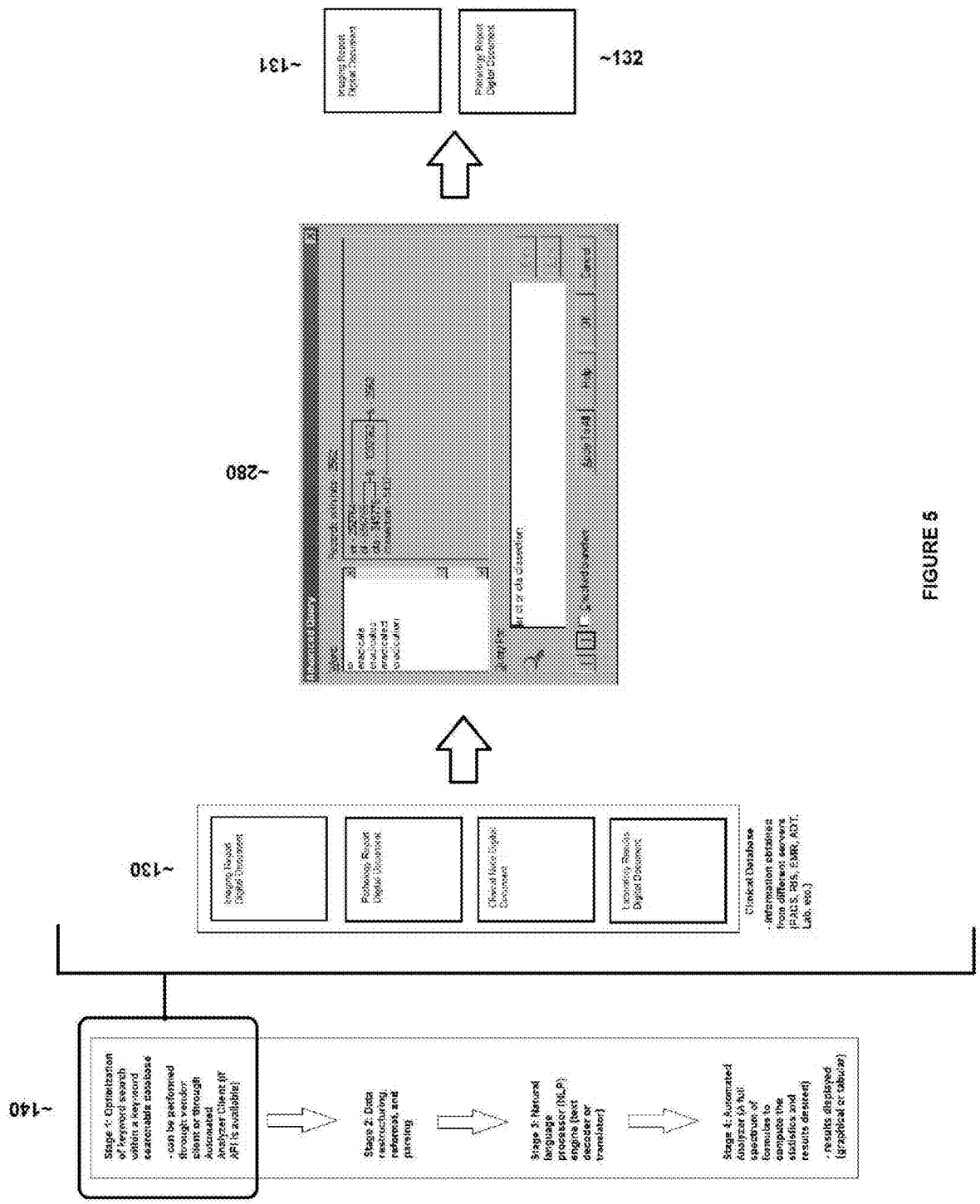
FIG. 5 is an illustration of a diagram showing an example of Stage 1 methods from clinical database search to report results, according to an embodiment of the present invention.

Referring now to FIG. 5, an example of Stage 1 methods 140 is shown as applied to a clinical database 130. First, the clinical database 130 is indexed for keyword (free text) search within a generic vendor search server 100 (FIG. 2) and an optimized keyword text search (as an example, "er ct or cta dissection") (note CTA refers to CT angiogram) is entered into an advanced query client 280 (refer to FIG. 6 for an enlarged version of 280). An example screen shot of an advanced query client user interface screen is shown. In the advanced query client, a simple example optimization of keyword search terms within a key-word searchable database is shown for basic understanding. The advanced query client 280 directs the optimized text search and retrieves specific and relevant results. As examples, the results of the advanced query are one imaging report 131 and one pathology report 132.

Figure 6:
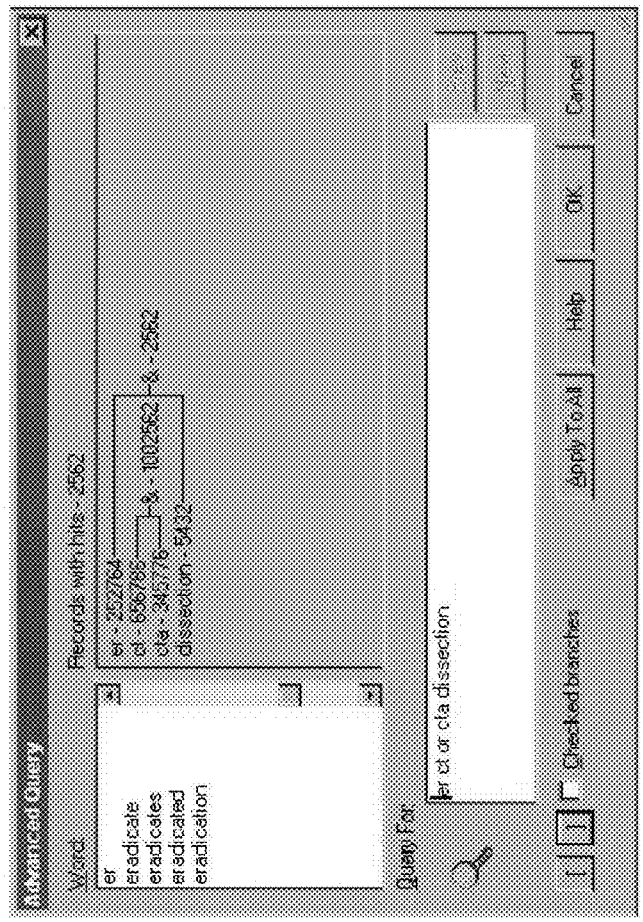
FIG. 6 is an example of a screen shot of an advanced query user interface screen, according to an embodiment of the present invention.

Referring now to FIG. 6, the results of the advanced query client 280 optimized text search described in FIG. 5 are shown. A total of 2562 records (reports) with hits were retrieved from a clinical database containing many more reports (millions).

As an example, the detailed methods for Stage 1: optimization of keyword search within a keyword searchable database, using Folio Views 4.2, are as follows:

1. Use bootstrapping and jackknifing techniques (hereby reference to the Journal of Biomedical Informatics. October 2005; 38(5):395-403 is now incorporated) on a radiologist (physician) verified and confirmed reference standard (calendar years 2002-2003 spreadsheet file, for aortic dissection protocol MDCT, obtained from a standard proprietary file system (IDX) 2002 and IDX 2003, created by a laborious manual search through paper records) to identify keyword search criteria to be used as a starting point. The goal is to retrieve all true hits while making an initial attempt to minimize false hits. As an example, Folio Views 4.2 on IDX 2002 for aortic dissection protocol MDCT using "er ct or cta dissection" as keywords. In the example of aortic dissection protocol MDCT, this exact search query will retrieve all records with true hits at the expense of retrieving of records with false hits (based on confounders such as "nodal dissection").

2. Because the original file contained only a portion of calendar year 2003 data, the analysis is focused on calendar year 2002 only. In an attempt to recreate a new 2002 database that matches the reference standard 2002 file in a more efficient manner, the reference standard 2002 file is analyzed in a successive manner for keyword search optimization. The goal here is to maintain retrieval all of true hits while minimizing, or eliminating, all false hits. To achieve keyword search accuracy optimization, the following modified Boolean and power search techniques for queries based on the imaging protocol in question are used.
   a. Use reference standard 2002 file in a successive manner to repetitively test the accuracy of new keywords, as they become identified, for a keyword based search engine (as an example, Folio Views)
   b. Reduce time needed to remove undesirable reports (as an example, non-aortic dissection protocol MDCT reports)
   c. Run keyword searchable program on database in question (as an example, Folio Views 4.2 on IDX 2002), specifically, when working in a windows OS→
      Click Windows icon→open IDX 2002
      Click Search→advanced query→type "er ct or cta dissection" versus "er or rc ct or cta dissection or intimal" (rapid care [RC]) (cross check results to insure all true hits are still retrieved)→type "er or rc ct or cta dissection or intimal or extravasation (cross check results to insure all true hits are still retrieved). (Folio is limited in ability, must be a term by itself. Example: "intim" with no letters or space behind it, although "intim/" (intim with a forward slash) will be considered a hit because it is a component separator or delimiter)
      Now total search="er or rc ct or cta dissection or intimal or extravasation no MVA no s/pMVA no "s/p MVA" no trauma no s/ptrauma no "s/p trauma" no "MR head" no "MR neck" no "CT face" (Note that MVA refers to motor vehicle accident and MR refers to magnetic resonance imaging) (This exact search query will provide optimal results with improved accuracy to retrieve all records with true hits while minimizing, or eliminating. retrieval of false hits based on confounders: this technique eliminates "nodal dissection" hits)

3. After the optimal keywords are identified, the keywords are validated against the reference standard 2002 file to insure accuracy 4. After the optimal keywords are validated for the given imaging protocol, the search is executed on a new clinical database 130
   a. Run keyword searchable program on database (as an example, Folio Views 4.2 on IDX 2004), specifically, when working in a windows OS→
      Click Windows icon→open IDX 2004
      Click Search→advanced query→type "er or rc ct or cta dissection or intimal or extravasation no MVA no s/pMVA no "s/p MVA" no trauma no s/ptrauma no "s/p trauma" no "MR head" no "MR neck" no "CT face" (This exact search query will provide optimal results with improved accuracy to retrieve all records with true hits while minimizing retrieval of false hits based on confounders: this technique eliminates "nodal dissection" hits)
      View→records with hits
      Click OK
      Click File→export data→type in file name=IDX 2004. er ct or cta dissection→save as Rich Text File→Location saved file on hard drive, server, etc.
      Click OK It is to be understood, of course, that while the exemplary methods detailed above are performed manually, the methods themselves can be performed in a more automated fashion by writing a simple script or other piece of code.

Stage 2

Figure 7:
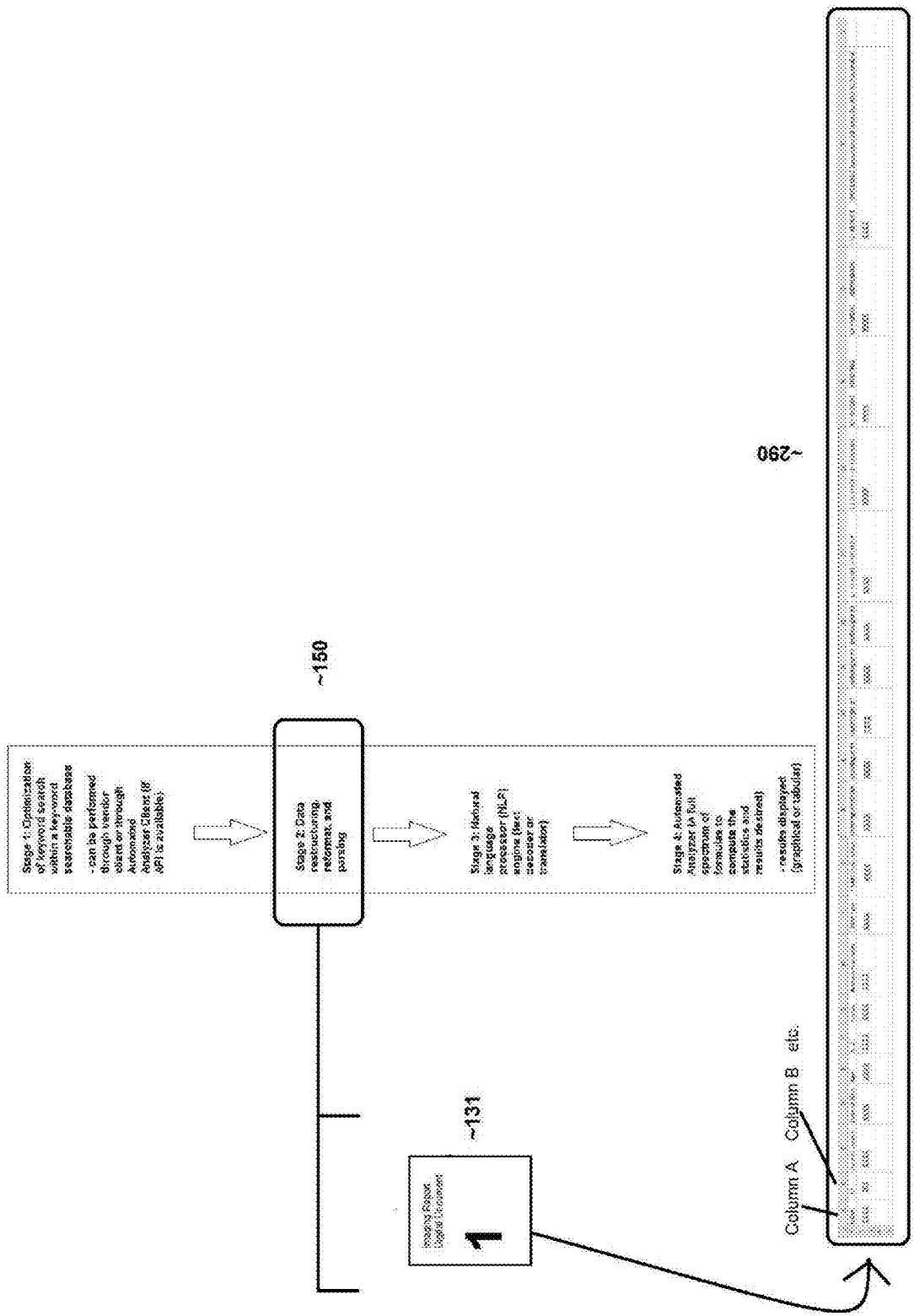
FIG. 7 is an illustration of a diagram showing an example of Stage 2 methods from report result to restructuring and parsing into a single row within a standard spreadsheet database, according to an embodiment of the present invention.

Referring now to FIG. 7, the execution of Stage 2 methods 150 is shown as applied to a single report 131 from Stage 1 (140, refer to FIG. 5) produced results (optimized and validated keyword search retrieved imaging reports). The imaging report 131 is shown restructured and parsed into several columns of a single row within a standard spreadsheet 290 (refer to FIG. 8 for an enlarged version). A simple example screen shot of parsed database header terms is shown for basic understanding. The entire process of report restructuring and parsing is fully automated.

Referring now to FIG. 8, example column headings are shown within a standard spreadsheet 290. The imaging report 131 (refer to FIG. 7) is restructured and parsed into text data (or alphanumeric string) cells across columns A to T within row 1 to match the data content described by the column headings. As an example, in the context of aortic dissection protocol MDCT, note that column T actually represents the summation of 23 duplicate columns, only one column T is shown for simplicity.

Figure 9:
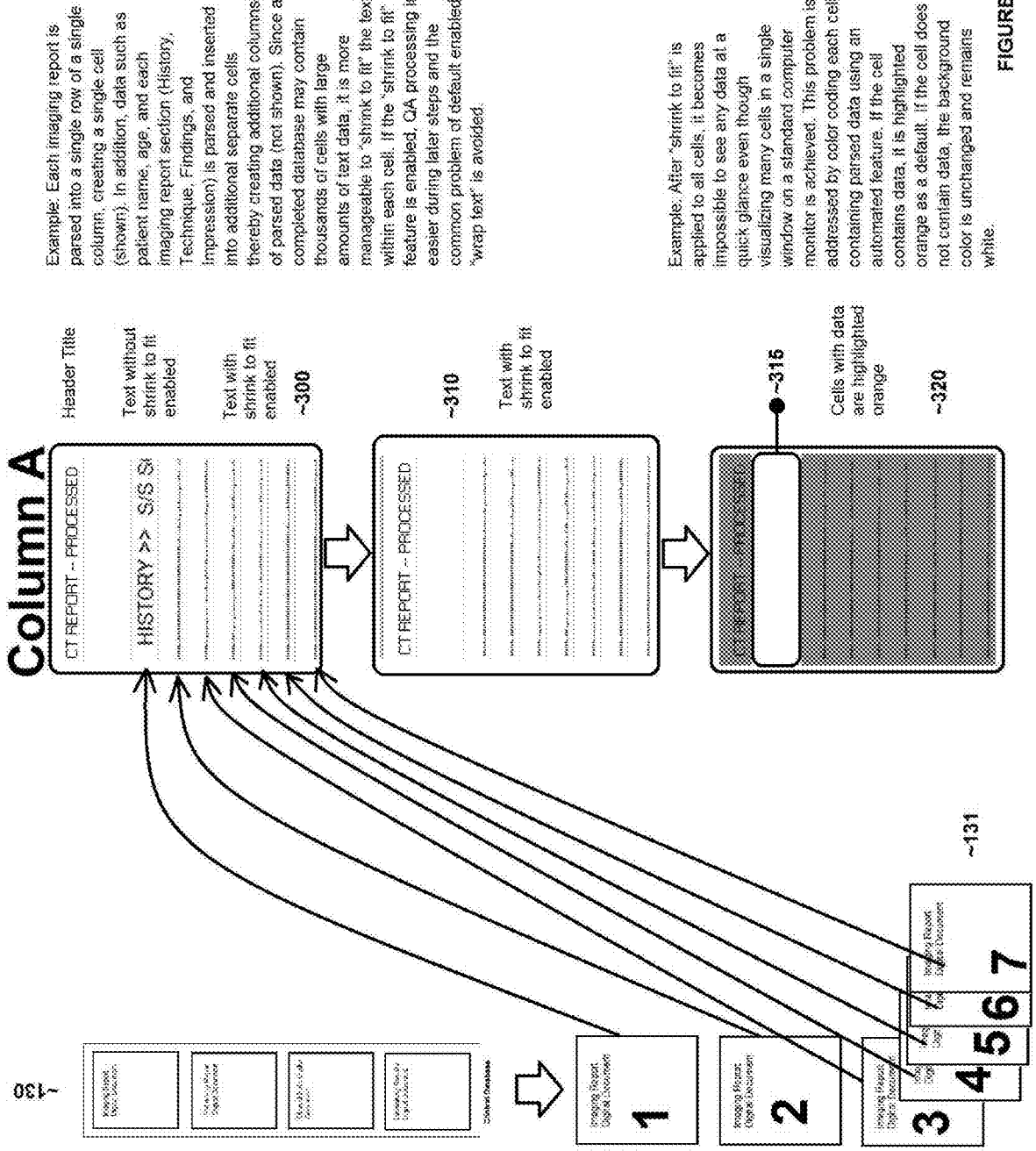
FIG. 9 is an illustration of a diagram showing an example of successive Stage 2 methods from clinical database search to multiple report results (Stage 1 methods are omitted for simplicity), according to an embodiment of the present invention.

Referring now to FIG. 9, a broad perspective example of successive Stage 2 methods (150, refer to FIG. 7) is shown. Example screen shots of multiple reports are shown after restructuring and parsing into multiple rows of a single column within a standard spreadsheet database. Transition from native text, to "shrink to fit" text, to color coded cells is also shown. Starting with a clinical database 130, Stage 1 (140, refer to FIG. 5) produced results are represented by seven different imaging reports 131. Stage 2 methods (150, refer to FIG. 7) are then applied to the seven reports 131 and one column A containing seven rows of restructured and parsed text data (or alphanumeric string) is produced 300. As an example, column A with the header title "CT REPORT— PROCESSED" contains seven rows or cells of text data (or alphanumeric string) 300. As described by the header title, each cell corresponds to the imaging report 131 that created it. Specifically, row 1 of column A contains the processed CT report text data (or alphanumeric string) produced by Stage 2 (150, refer to FIG. 7) as applied to imaging report 1 (131). As an example, when Stage 2 (150, refer to FIG. 7) is applied to all Stage 1 (140, refer to FIG. 5) results, each imaging report is parsed into a single row of a single column, creating a single cell (shown). Collectively, if Stage 1 produced results equal 100 imaging reports, Stage 2 will produce 100 cells of corresponding text data (or alphanumeric string) within Column A (as an example, header title "CT REPORT—PROCESSED"). In addition, data such as patient name, age, and each imaging report section (History, Technique, Findings, and Impression) is parsed and inserted into additional separate cells thereby creating additional columns of parsed data (290, refer to FIG. 8). Since a completed database may contain thousands of cells with large amounts of text data (or alphanumeric string), it is more manageable to "shrink to fit" the text (300 and 310) within each cell. If the "shrink to fit" feature is enabled (300 and 310), QA processing is easier during later steps and the common problem of default enabled "wrap text" is avoided. As an example, after "shrink to fit" is applied to all cells 310, it becomes impossible to see any data at a quick glance even though visualizing many cells in a single window on a standard computer monitor is achieved. This problem is addressed by color coding each cell containing parsed data using an automated feature. If the cell contains data, it is highlighted orange as a default 320. If the cell does not contain data, the background color is unchanged and remains white 315. The color coded cells enable downstream processing or visual programming.

Figure 10:
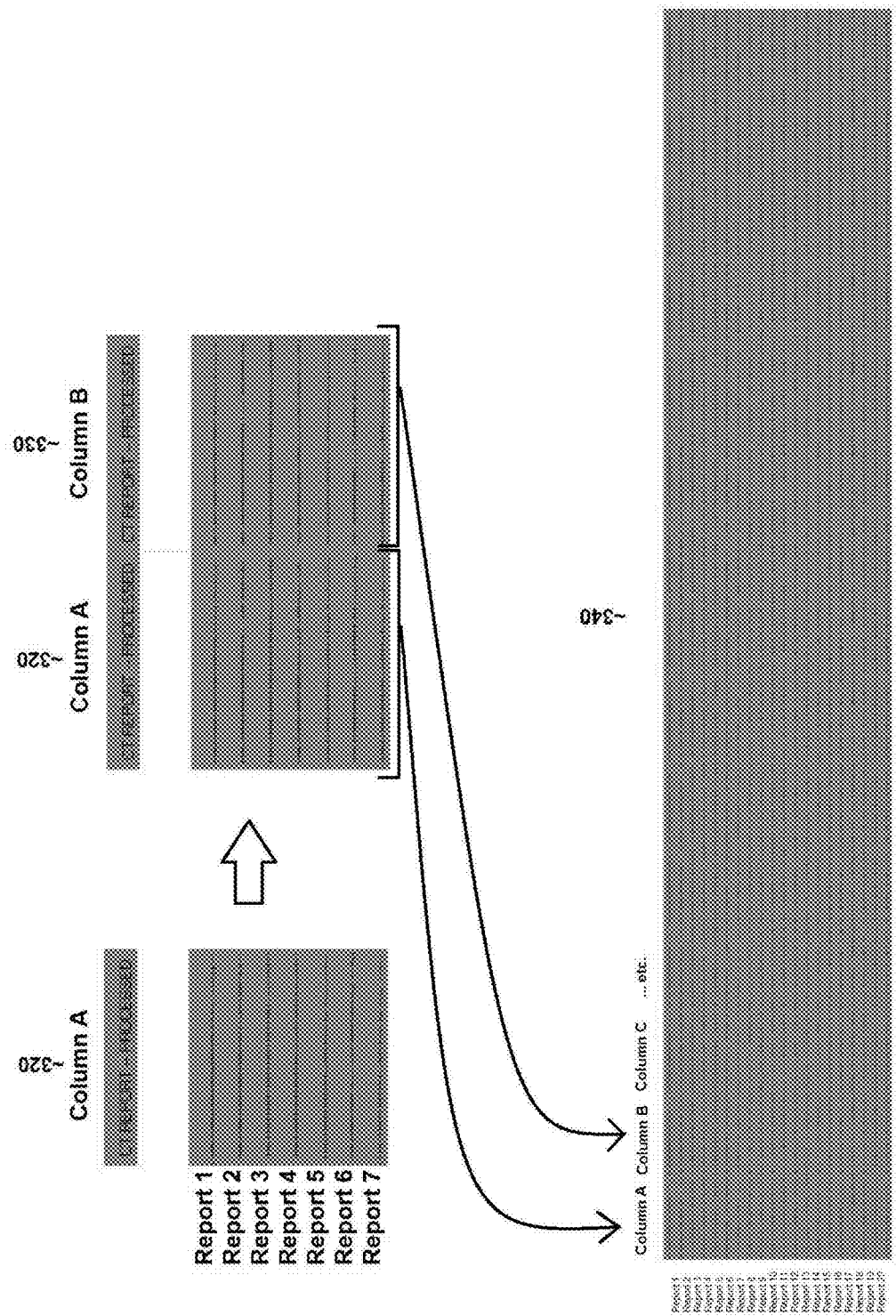
FIG. 10 is an illustration of a diagram showing an example of successive Stage 2 methods from multiple report results in multiple color coded rows of a single column to multiple color coded columns through parsing and/or replication; successive steps transform a column of restructured and parsed reports into a large color coded database, according to an embodiment of the present invention.

Referring now to FIG. 10, successive Stage 2 methods (150, refer to FIG. 7) are shown as applied to multiple reports in multiple corresponding color coded rows of a single column A (320) resulting in multiple corresponding color coded columns A, B, and C (320, 330, and 340) through additional parsing and/or replication. Successive steps transform a single column 320 of restructured and parsed report text data (or alphanumeric string) into a large color coded database 340. As an example, 20 imaging reports create 20 rows of cells parsed into many more columns than labeled 340. Column parsing and/or replication can be repeated as many times as necessary to meet downstream processing or analytic needs. A completed database can contain all aspects of data (patient demographics, report sections, full reports, etc.). As the "shrink to fit" feature remains enabled, data within each cell is not visible to the human eye thereby improving downstream processing.

Referring now to Stage 2 in its entirety, the process creates both a translational and non-translational database.

As an example, the detailed methods for Stage 2: Data restructuring, reformat, and parsing, using Microsoft Excel, are as follows:

The methods below describe how to manually parse Clinical Document Architecture (CDA), Continuity of Care Record (CCR), and Continuity of Care Document (CCD), or other standard data formats of modern EMR systems. It is a method of Electronic Data Interchange (EDI) parsing that allows the subsequent Stages (3 and 4) to be implemented.

1. Open Rich Text File in a word processing program (as an example, Microsoft Word)→Save file using the following format parameters (plain text, ASC II)
2. Click Format→reveal formatting→check distinguish style source and show all formatting marks, deleting everything by wizard on left
3. Use find/replace function to delete tabs, paragraphs, and colons in text
   a. Rebuild paragraphs to create rows within a spreadsheet (setup of report A to be separated from report B) (as an example, Microsoft Excel)
      i. Rebuild text by separating all text with front and back colons (flanked colons to trap desired text into one cell within column). Depending on the origin of the report, the delimiters may be different (as an example, the a certain string of alphanumeric character followed by a comma, in this case the entire string can be searched for and replaced with a single colon to help the later application of an automated parser).
   b. Rebuild text a second time to create columns within a spreadsheet (set up text report to be parsed).
      i. The same text can be analyzed an additional time to set delimiters (key text: as examples, examination ID number or patient name) as the placeholders for parsing the data into separate cells on the same row. This allows parsing of data such as examination ID number, patient name, patient record number, date of exam, etc.
4. Run spreadsheet application
   a. Import and separate report A from report B
      i. As an example, in Microsoft Excel→data→import external data→import data→select delimited→delimiter=colon→text style→finish
   b. Import delimited text within report to be parsed within a row into separate cells/columns
      i. As an example, in Microsoft Excel→data→import external data→import data→select delimited→delimiter=pre-defined alphanumeric strings→text style→finish
      ii. The following additional text string examples can serve as the "replacer text" to allow standardization of report format
         1. HISTORY >>
         2. TECHNIQUE >>
         3. FINDINGS >>
         4. IMPRESSION >>

It is to be understood, of course, that while the exemplary methods detailed above are performed manually, the methods themselves can be performed in a more automated fashion by writing a simple script or other piece of code.

Stage 3

Figure 11:
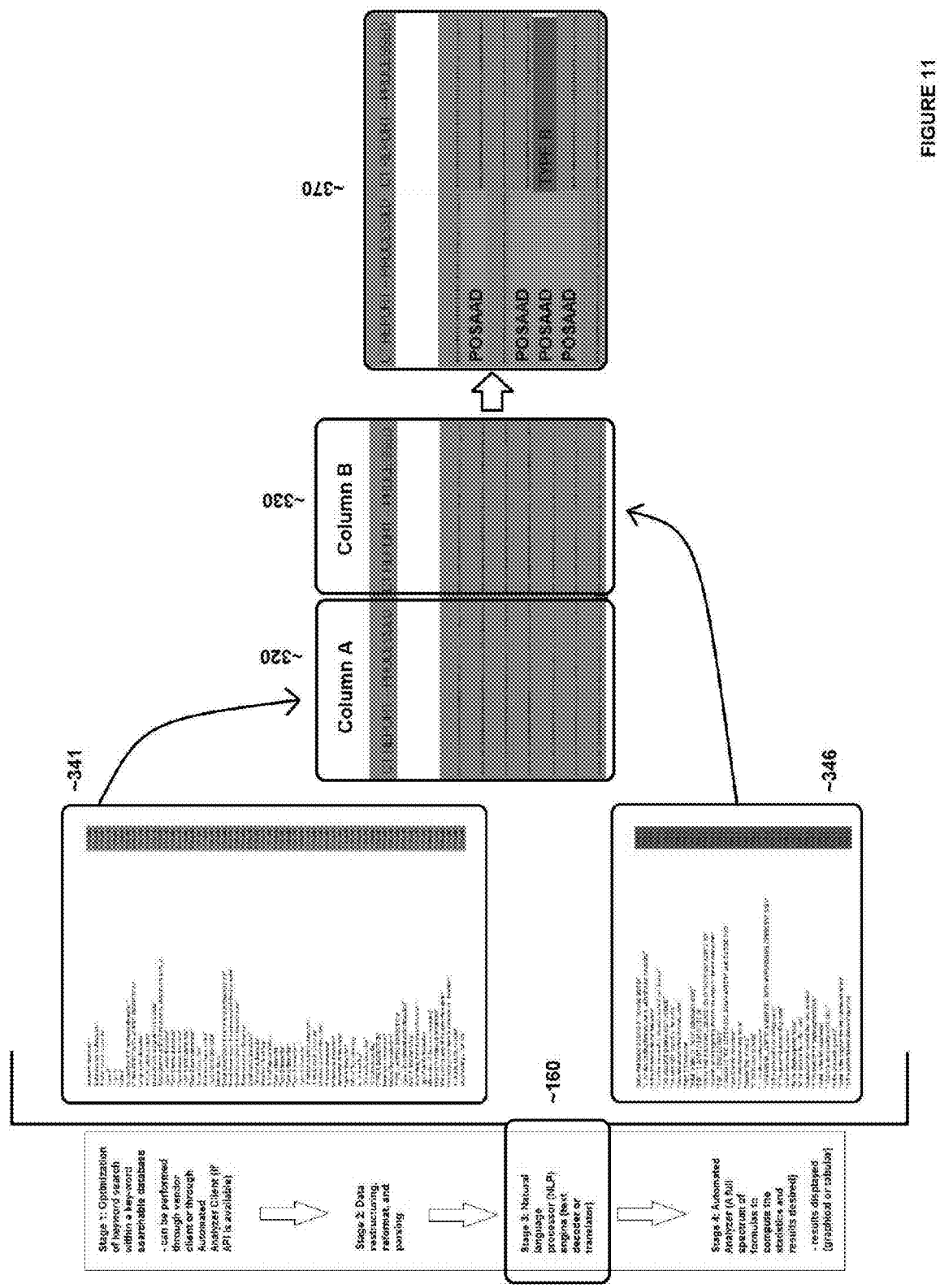
FIG. 11 is an illustration of a diagram showing an example of Stage 3 methods applied to multiple reports resulting in multiple color coded rows of a sample two column color coded database, to simplify understanding, according to an embodiment of the present invention.

Referring now to FIG. 11, Stage 3 methods (160) are shown as applied to multiple reports, specifically seven reports, resulting in seven color coded rows of a sample two column (Column A 320 and Column B 330) color coded database, to simplify understanding. As representative examples, two partial NLP engine tables (341 and 346, refer to FIGS. 13A and 14A for enlarged versions) are shown decoding or translating the text data (or alphanumeric string) within the cells or rows of both columns while simultaneously processing the same text data (or alphanumeric string) for application of secondary color coding. Specifically, partial NLP engine table 341 (decodes for positive AAD examinations) is applied to column A (320) and partial NLP engine table 346 (decodes for Type B examinations) is applied to column B (330). The result of applying the partial NLP engine tables to columns A and B are threefold. First, the two column database text data (or alphanumeric string) is decoded according to the single NLP engine table, as applied. Second, the two column database undergoes secondary color coding (fill color or background cell color, plus or minus bolding text) according to, and matched to, the previous text data (or alphanumeric string) decode step. Third, an iterative technique using successive steps of both text data (or alphanumeric string) decoding and application of secondary color coding provides a level of natural language understanding, inherent Quality Assurance, validation, and verification. In other words, decoding an examination as positive for AAD 20 times using 20 different markers yields more accuracy and confidence, in the technique than a single decoding step. In the example shown, a subtle yet important point to realize demonstrates the iterative power of the described technique. Application of partial NLP engine table 346 (decoded for Type B examinations) is only valid if executed after the application of partial NLP engine table 341 (decodes for positive AAD examinations). In other words, the examination must be decoded as positive for AAD before the same examination can be decoded as a subcategory (sub-classification or type) of AAD. When applied in succession and processed together, the additive effect of the single NLP decoding steps used in Stage 3 transform the database into a form of natural language understanding. The native text data (or alphanumeric string), text data (or alphanumeric string) without a decoded result, within each cell is still not visible to the human eye as the "shrink to fit" feature remains enabled thereby maintaining text data (or alphanumeric string) minimization to improve downstream processing. Further, the automated background color change from no (native or white) color to orange color (row directly below header title, 320 and 330) easily demonstrates that many cells now contain text data (or alphanumeric string) (or alphanumeric string(s)) representing a functioning Stage 2. Further, since some of the orange cells subsequently changed from orange fill color to a different color (from orange to green or red), the database also demonstrates a functioning Stage 3.

Referring now to FIG. 12, a representative screen shot of a NLP engine table (dissection protocol) is shown. The specific engine table displayed 340 decodes the report, or alphanumeric string, for dissection protocol. In other words, the NLP engine decodes the report to identify if the dissection protocol (in the context described, aortic dissection protocol CT is implied) was properly performed as designed.

The NLP engine is deciphering if in the event the dissection protocol was ordered was it performed correctly or incorrectly. If the dissection protocol was performed correctly and properly as designed, the remaining decode steps are executed. If the dissection protocol was performed incorrectly, improperly, not as designed, or was never actually ordered (220, refer to FIG. 3), then the same or a different NLP decode algorithm can be applied. As an example, sometimes when an aortic dissection protocol CT is ordered, a different imaging protocol is actually performed for a variety of reasons, As shown, an aneurysm protocol can be a possible anomaly or substitution and is easily identified by the secondary color coding applied, here the secondary color coding is "pink" compare to the "blue" dissection protocol). As can be inferred, one decoding step opens up a host of downstream processing or other NLP decoding steps.

Referring now to FIG. 13A, a representative screen shot of a NLP engine table (POSAAD) is shown. The specific engine table displayed 341 decodes the report, or alphanumeric string, for POSAAD, or positive AAD examinations. In other words, the NLP engine decodes the report to identify if the examination is positive for an acute aortic disorder (AAD). In the context described, aortic dissection protocol CT is implied, and should be decoded in an antecedent manner before 341 is considered as a valid next step in the succession of decoding steps or decoding algorithm. Although, note the preceding method of protocol A to diagnosis A is not a mutually exclusive algorithm or path. Decoding table 341 can be applied in different algorithms or decoding paths as necessary to identify, match, and assign a report as positive for AAD in the context of an alternative diagnosis from a non-aortic dissection specific imaging protocol.

Referring now to FIG. 13B, a second representative screen shot of a NLP engine table (POSAAD) is shown. The specific engine table displayed 342 is a continuation of 341 (refer to FIG. 13A) (the entire engine table is too large to display on a single screen shot).

Referring now to FIG. 13C, a third representative screen shot of a NLP engine table (POSAAD) is shown. The specific engine table displayed 343 is a continuation of 341 and 342 (refer to FIGS. 13A and 13B) (the entire engine table is too large to display on a single screen shot).

Referring now to FIG. 13D, a fourth representative screen shot of a NLP engine table (POSAAD) is shown. The specific engine table displayed 344 is a continuation of 341, 342, and 343 (refer to FIGS. 13A, 13B, and 13C) (the entire engine table is too large to display on a single screen shot).

Figure 13E:
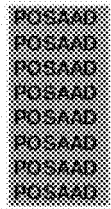
FIG. 13E is an example of a screen shot of a NLP engine table (POSAAD, cont'd.), according to an embodiment of the present invention.

Referring now to FIG. 13E, a fifth representative screen shot of a NLP engine table (POSAAD) is shown. The specific engine table displayed 345 is a continuation of 341, 342, 343, and 344 (refer to FIGS. 13A, 13B, 13C, and 13D) (the entire engine table is too large to display on a single screen shot).

Referring now to FIG. 14A, a representative screen shot of a NLP engine table (Type A and B) is shown (these are well described AAD subtypes in the literature). The specific engine table displayed (346 and 347) decodes the report, or alphanumeric string, for Type A and Type B, or positive subtypes of AAD examinations. In other words, the NLP engine decodes the report to identify if the examination is positive for a Type A or Type B acute aortic disorders (AAD). In the context described, aortic dissection protocol CT is implied, and should be decoded in an antecedent manner before 346 and/or 347 is considered as a valid next step in the succession of decoding steps or decoding algorithm. Although, the method of protocol A to diagnosis A to subtype A or B is not always mutually exclusive algorithm or path (for the example shown, the algorithm is mutually exclusive for single finding or diagnosis). Decoding table 346 and/or 347 can be applied in different algorithms or decoding paths as necessary to identify, match, and assign a report as positive for a Type A or Type B AAD in the context of an alternative diagnosis from a non-aortic dissection specific imaging protocol.

Figure 14B:
FIG. 14B is an example of a screen shot of a NLP engine table (Type A and B, cont'd.), according to an embodiment of the present invention.

Referring now to FIG. 14B, a second representative screen shot of a NLP engine table (Type B) is shown. The specific engine table displayed 348 is a continuation of 347, and more specifically 346 (refer to FIG. 14A). In reality, all three engine tables should be applied dynamically together as they collectively represent one large engine table. Further, Type A and Type B are mutually exclusive classifications when applied to a single finding or diagnosis (the entire engine table is too large to display on a single screen shot). Note that the portion of the NLP engine table displayed is for Type B only.

Referring now to FIG. 15A, a representative screen shot of a NLP engine table (Type 1, 2, and 3) is shown (these are well described AAD subtypes in the literature). The specific engine table displayed (349) decodes the report, or alphanumeric string, for Type 1 and Type 2, or Type 3 positive subtypes of AAD examinations. In other words, the NLP engine decodes the report to identify if the examination is positive for a Type 1, Type 2, or Type 3 acute aortic disorders (AAD). In the context described, aortic dissection protocol CT is implied, and should be decoded in an antecedent manner before 349 is considered as a valid next step in the succession of decoding steps or decoding algorithm. The method of diagnosis A to subtype 1 or 2 or 3 may or may not be a mutually exclusive algorithm or path (for the example shown, the algorithm is mutually exclusive for single finding or diagnosis). Decoding table 349 can be applied in different algorithms or decoding paths as necessary to identify, match, and assign a report as positive for a Type 1, Type 2, or Type 3 AAD in the context of an alternative diagnosis from a non-aortic dissection specific imaging protocol. In addition, the secondary color coding contains superimposed NLP or automated understanding. The cell background color refers to a different, yet to be described in said application, variant classification scheme based on the finding or diagnosis (five total variants, well describe in the literature for AAD). Green cell color corresponds to class 1 (351, refer to FIG. 16), orange cell color corresponds to class 2, blue cell color corresponds to class 3 (not shown), yellow cell color corresponds to class 4, and red cell color corresponds to class 5 (not shown). In the example of variant classification of AAD, some are and some are not mutually exclusive, thereby making AAD variants a proper prototype for said decoding ability descriptions.

Referring now to FIG. 15B, a second representative screen shot of a NLP engine table (Type 3) is shown. The specific engine table displayed 350 is a continuation of 349, and more specifically, Type 3 decoding within engine table 349 (refer to FIG. 15A). In reality, the two engine tables should be applied dynamically together as they collectively represent one large engine table. Further, Type 1, Type 2, and Type 3 are mutually exclusive classifications when applied to a single finding or diagnosis (the entire engine table is too large to display on a single screen shot). Note that the portion of the NLP engine table displayed is for Type 3 only.

Referring now to FIG. 16, a representative screen shot of a NLP engine table (CLASS 1) is shown (Class 1 is among five variant classes that are well described for AAD in the literature). The specific engine table displayed (351) decodes the report, or alphanumeric string, for variant Class 1 AAD examinations. In other words, the NLP engine decodes the report to identify if the examination is positive for a variant Class 1 acute aortic disorder (AAD). In the context described, aortic dissection protocol CT is implied, and should be decoded in an antecedent manner before 351 is considered as a valid next step in the succession of decoding steps or decoding algorithm. The method of diagnosis A to variant Class 1 or Class 2 or Class 3 or Class 4 or Class 5 may or may not be a mutually exclusive algorithm or path (for the example shown, the algorithm is a not mutually exclusive for single finding or diagnosis). Decoding table 351 can be applied in different algorithms or decoding paths as necessary to identify, match, and assign a report as positive for a variant Class 1, Class 2, Class 3, Class 4, or Class 5 AAD in the context of an alternative diagnosis from a non-aortic dissection specific imaging protocol. In addition, the secondary color coding contains superimposed NLP or automated understanding. The cell background color refers to the specific variant classification scheme as previously described (351) based on the finding or diagnosis. An additional layer of NLP generated automated understanding can be derived from the technique as shown, if more than one variant Class(es) is decoded in a single examination, thereby representing a variably described single finding versus variably described additional finding(s), the dominant finding (or finding with the greatest number of decoded hits) can be represented by the secondary color coding (as shown, CLASS 1 cells are green fill color) when applied to the variant Class column (the column with the header title Variant Class, in the example of AAD). Note that NLP engine tables representative of the remaining variant Classes are not shown, for simplicity. (There are five total variants, well described in the literature for AAD).

Referring now to FIG. 17A, a representative screen shot of a NLP engine table (NEG CLASS 1) is shown. The specific engine table displayed (352) decodes the report, or alphanumeric string, for negative variant Class 1 AAD examinations. In other words, the NLP engine decodes the report to identify if the examination is negative for a variant Class 1 acute aortic disorder (AAD). In the context described, aortic dissection protocol CT is implied, and should be decoded in an antecedent manner before 352 is considered as a valid next step in the succession of decoding steps or decoding algorithm. The method of diagnosis A to negative variant Class 1 or Class 2 or Class 3 or Class 4 or Class 5 may or may not be a mutually exclusive algorithm or path (for the example shown, the algorithm is a not mutually exclusive for single finding or diagnosis). Decoding table 352 can be applied in different algorithms or decoding paths as necessary to identify, match, and assign a report as positive for a negative variant Class 1, Class 2, Class 3, Class 4, or Class 5 AAD in the context of an alternative diagnosis, or lack thereof, from a non-aortic dissection specific imaging protocol. In addition, the secondary color coding contains superimposed NLP or automated understanding. The cell background color refers to the specific negative variant classification scheme, similar to previously described (351, refer to FIG. 16) based on the absence of a finding or diagnosis. An additional layer of NLP generated automated understanding can be derived from the technique as shown, if the absence of more than one variant Class(es) is decoded in a single examination, thereby representing a variably described absence of a single finding versus variably described absence of an additional finding(s), the dominant finding, or lack thereof (or finding with the greatest number of decoded negative hits) can be represented by the secondary color coding when applied to the negative variant Class column (the column with the header title Negative Variant Class, in the example of AAD). Note that NLP engine tables representative of the remaining negative variant Classes are not shown, for simplicity. (There are five total variants, well described in the literature for AAD).

Referring now to FIG. 17B, a second representative screen shot of a NLP engine table (NEG CLASS 1) is shown. The specific engine table displayed 353 is a continuation of 352 (refer to FIG. 17A). In reality, the two engine tables should be applied dynamically together as they collectively represent one large engine table (the entire engine table is too large to display on a single screen shot).

Referring now to FIG. 17C, a third representative screen shot of a NLP engine table (NEG CLASS 1) is shown. The specific engine table displayed 354 is a continuation of 352 and 353 (refer to FIGS. 17A and 17B). In reality, the three engine tables should be applied dynamically together as they collectively represent one large engine table (the entire engine table is too large to display on a single screen shot).

Referring now to FIG. 18, a representative screen shot of a NLP engine table (CLASS 2) is shown (Class 2 is among five variant classes that are well described for AAD in the literature). The specific engine table displayed (355) decodes the report, or alphanumeric string, for variant Class 2 AAD examinations. In other words, the NLP engine decodes the report to identify if the examination is positive for a variant Class 2 acute aortic disorder (AAD). In the context described, aortic dissection protocol CT is implied, and should be decoded in an antecedent manner before 355 is considered as a valid next step in the succession of decoding steps or decoding algorithm. The method of diagnosis A to variant Class 1 or Class 2 or Class 3 or Class 4 or Class 5 may or may not be a mutually exclusive algorithm or path (for the example shown, the algorithm is a not mutually exclusive for single finding or diagnosis). Decoding table 355 can be applied in different algorithms or decoding paths as necessary to identify, match, and assign a report as positive for a variant Class 1, Class 2, Class 3, Class 4, or Class 5 AAD in the context of an alternative diagnosis from a non-aortic dissection specific imaging protocol. In addition, the secondary color coding contains superimposed NLP or automated understanding. The cell background color refers to the specific variant classification scheme as previously described (351, refer to FIG. 16) based on the finding or diagnosis. An additional layer of NLP generated automated understanding can be derived from the technique as shown, if more than one variant Class(es) is decoded in a single examination, thereby representing a variably described single finding versus variably described additional finding(s), the dominant finding (or finding with the greatest number of decoded hits) can be represented by the secondary color coding (as shown, CLASS 2 cells are red fill color) when applied to the variant Class column (the column with the header title Variant Class, in the example of AAD). Note that NLP engine tables representative of the remaining variant Classes are not shown, for simplicity. (There are five total variants, well described in the literature for AAD).

Referring now to FIG. 19A, a representative screen shot of a NLP engine table (STABLE CLASS 2) is shown. The specific engine table displayed (356) decodes the report, or alphanumeric string, for stable variant Class 2 AAD examinations. In other words, the NLP engine decodes the report to identify if the examination is stable for a variant Class 2 acute aortic disorder (AAD). In the context described, aortic dissection protocol CT is implied, and should be decoded in an antecedent manner before 356 is considered as a valid next step in the succession of decoding steps or decoding algorithm. The method of diagnosis A to stable variant Class 1 or Class 2 or Class 3 or Class 4 or Class 5 may or may not be a mutually exclusive algorithm or path (for the example shown, the algorithm is a not mutually exclusive for single finding or diagnosis). Decoding table 356 can be applied in different algorithms or decoding paths as necessary to identify, match, and assign a report as positive for a stable variant Class 1, Class 2, Class 3, Class 4, or Class 5 AAD in the context of an alternative diagnosis, or lack thereof, from a non-aortic dissection specific imaging protocol. In addition, the secondary color coding contains superimposed NLP or automated understanding. The cell background color refers to the specific stable variant classification scheme, similar to previously described (351, refer to FIG. 16) based on the finding or diagnosis. An additional layer of NLP generated automated understanding can be derived from the technique as shown, if more than one stable variant Class(es) is decoded in a single examination, thereby representing a variably described presence/absence of a single finding versus variably described presence/absence of an additional finding(s), the dominant finding, or lack thereof (or finding with the greatest number of decoded hits) can be represented by the secondary color coding when applied to the stable variant Class column (the column with the header title Stable Variant Class, in the example of AAD). Note that NLP engine tables representative of the remaining stable variant Classes are not shown, for simplicity. (There are five total variants, well described in the literature for AAD).

Referring now to FIG. 19B, a second representative screen shot of a NLP engine table (STABLE CLASS 2) is shown. The specific engine table displayed 357 is a continuation of 356 (refer to FIG. 19A). In reality, the two engine tables should be applied dynamically together as they collectively represent one large engine table (the entire engine table is too large to display on a single screen shot).

Referring now to FIG. 19C, a third representative screen shot of a NLP engine table (STABLE CLASS 2) is shown. The specific engine table displayed 358 is a continuation of 356 and 357 (refer to FIGS. 19A and 19B). In reality, the three engine tables should be applied dynamically together as they collectively represent one large engine table (the entire engine table is too large to display on a single screen shot).

Referring now to FIG. 19D, a fourth representative screen shot of a NLP engine table (STABLE CLASS 2) is shown. The specific engine table displayed 359 is a continuation of 356, 357, and 358 (refer to FIGS. 19A, 19B, and 19C). In reality, the four engine tables should be applied dynamically together as they collectively represent one large engine table (the entire engine table is too large to display on a single screen shot).

Referring now to FIG. 19E, a fifth representative screen shot of a NLP engine table (STABLE CLASS 2) is shown. The specific engine table displayed 360 is a continuation of 356 through 359 (refer to FIG. 19A through 19D). In reality, the five engine tables should be applied dynamically together as they collectively represent one large engine table (the entire engine table is too large to display on a single screen shot).

Referring now to FIG. 19F, a sixth representative screen shot of a NLP engine table (STABLE CLASS 2) is shown. The specific engine table displayed 361 is a continuation of 356 through 360 (refer to FIG. 19A through 19E). In reality, the six engine tables should be applied dynamically together as they collectively represent one large engine table (the entire engine table is too large to display on a single screen shot).

Referring now to FIG. 19G, a seventh representative screen shot of a NLP engine table (STABLE CLASS 2) is shown. The specific engine table displayed 362 is a continuation of 356 through 361 (refer to FIG. 19A through 19F). In reality, the seven engine tables should be applied dynamically together as they collectively represent one large engine table (the entire engine table is too large to display on a single screen shot).

Referring now to FIG. 20A, a representative screen shot of a NLP engine table (NEG CLASS 2) is shown. The specific engine table displayed (363) decodes the report, or alphanumeric string, for negative variant Class 2 AAD examinations. In other words, the NLP engine decodes the report to identify if the examination is negative for a variant Class 2 acute aortic disorder (AAD). In the context described, aortic dissection protocol CT is implied, and should be decoded in an antecedent manner before 363 is considered as a valid next step in the succession of decoding steps or decoding algorithm. The method of diagnosis A to negative variant Class 1 or Class 2 or Class 3 or Class 4 or Class 5 may or may not be a mutually exclusive algorithm or path (for the example shown, the algorithm is a not mutually exclusive for single finding or diagnosis). Decoding table 363 can be applied in different algorithms or decoding paths as necessary to identify, match, and assign a report as positive for a negative variant Class 1, Class 2, Class 3, Class 4, or Class 5 AAD in the context of an alternative diagnosis, or lack thereof, from a non-aortic dissection specific imaging protocol. In addition, the secondary color coding contains superimposed NLP or automated understanding. The cell background color refers to the specific negative variant classification scheme, similar to previously described (351, refer to FIG. 16) based on the absence of a finding or diagnosis. An additional layer of NLP generated automated understanding can be derived from the technique as shown, if the absence of more than one variant Class(es) is decoded in a single examination, thereby representing a variably described absence of a single finding versus variably described absence of an additional finding(s), the dominant finding, or lack thereof (or finding with the greatest number of decoded negative hits) can be represented by the secondary color coding when applied to the negative variant Class column (the column with the header title Negative Variant Class, in the example of AAD). Note that NLP engine tables representative of the remaining negative variant Classes are not shown, for simplicity. (There are five total variants, well described in the literature for AAD).

Referring now to FIG. 20B, a second representative screen shot of a NLP engine table (NEG CLASS 2) is shown. The specific engine table displayed 364 is a continuation of 363 (refer to FIG. 20A). In reality, the two engine tables should be applied dynamically together as they collectively represent one large engine table (the entire engine table is too large to display on a single screen shot).

Referring now to FIG. 21A, a representative screen shot of a NLP engine table (ANEURYSM) is shown. The specific engine table displayed 365 decodes the report, or alphanumeric string, for ANEURYSM, or positive aneurysm examinations. In other words, the NLP engine decodes the report to identify if the examination is positive for an aneurysm, one of the acute aortic disorders (AAD). In the context described, aortic dissection protocol CT is not necessarily implied, and does not need to be decoded in an antecedent manner before 365 is considered as a valid next step in the succession of decoding steps or decoding algorithm. The preceding method of protocol A to diagnosis A is a mutually exclusive algorithm or path (in the context of aortic dissection protocol CT). Decoding table 365 can be applied in different algorithms or decoding paths as necessary to identify, match, and assign a report as positive for an aneurysm in the context of an alternative diagnosis from a non-aortic dissection specific imaging protocol.

Referring now to FIG. 21B, a second representative screen shot of a NLP engine table (ANEURYSM) is shown. The specific engine table displayed 366 is a continuation of 365 (refer to FIG. 21A) (the entire engine table is too large to display on a single screen shot).

Figure 22:
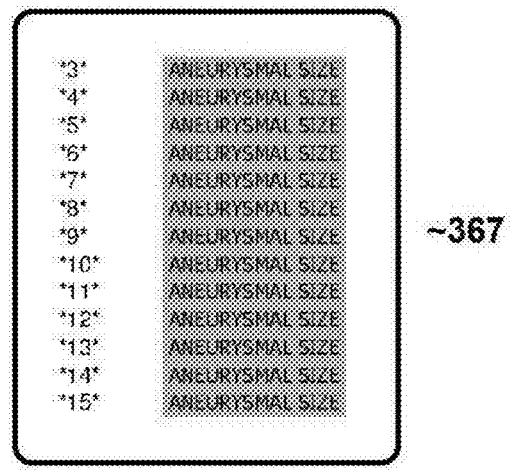
FIG. 22 is an example of a screen shot of a NLP engine table (ANEURYSMAL SIZE), according to an embodiment of the present invention.

Referring now to FIG. 22, a representative screen shot of a NLP engine table (ANEURYSMAL SIZE) is shown. The specific engine table displayed 367 decodes the report, or alphanumeric string, for ANEURYSMAL SIZE, or positive aneurysm examinations based on a described alphanumerical size. In other words, the NLP engine decodes the report to identify if the examination is positive for an aneurysm, one of the acute aortic disorders (AAD), based on an actual number or measurement. In the context described, aortic dissection protocol CT is not necessarily implied, but does not need to be decoded in an antecedent manner before 367 is considered as a valid next step in the succession of decoding steps or decoding algorithm. However, in the context described, an examination decoded positive for an aneurysm needs to occur antecedent or subsequent for 367 to be considered a valid decoding step. The preceding method of size (measurement or numerical value) A to diagnosis (or finding) A is a not mutually exclusive algorithm or path (in the context of aneurysmal size within aortic dissection protocol CT). Decoding table 367 can be applied in different algorithms or decoding paths as necessary to identify, match, and assign a report as positive for an aneurysmal size in the context of an alternative diagnosis from a non-aortic dissection specific imaging protocol. Further, and more importantly, the method of decoding size (measurement or numerical value) to aneurysmal size is not the only option using the described technique. The decoding table 367, or a similar decoding table, can be redefined, verified, and validated for different diagnoses and/or findings given the proper antecedent (or subsequent) decoding steps as required to provide the necessary diagnostic category (classification) or relevance (as examples, size or measurement of a lung nodule or displacement of a bone fracture).

Referring now to FIG. 23A, a representative screen shot of a NLP engine table (ANEURYSM LOCATIONS) is shown (aneurysmal location categories, and vascular dilatations not meeting aneurysmal size, are well described for AAD in the literature). The engine table categorizes newly diagnosed aneurysms into following: ascending thoracic aorta, descending thoracic aorta, and abdominal aorta. The engine table also recognizes aortic dilatation locations not meeting aneurysmal size. The specific engine table displayed (368) decodes the report, or alphanumeric string, for newly diagnosed aneurysmal (or vascular dilatation) locations (one of the categories of positive AAD examinations). Specifically, the decoder table defines locations according to the following locations: (NEW ASC TAA, NEW DES TAA, NEW AAA, NEW ASC DIL, and NEW DES DIL), where AAA refers to Abdominal Aortic Aneurysm. In other words, the NLP engine decodes the report to identify if the examination is positive for a new aneurysmal (or vascular dilatation) location acute aortic disorder (AAD). The engine table categorizes newly diagnosed aneurysms (or vascular dilatation) into following: ascending thoracic aorta, descending thoracic aorta, and abdominal aorta. The engine table also recognizes aortic dilatation locations not meeting aneurysmal size. Further, when decoding table 368 is applied in combination with decoding tables such as 366 and 367, decoding table 368 now generates and provides artificial and automated report understanding for a finding(s) location within the human body based on the given examination. In the context described, aortic dissection protocol CT is implied, but does not be decoded in an antecedent manner before 368 is considered as a valid next step in the succession of decoding steps or decoding algorithm. The method of diagnosis A to category A, B, C, D, or E, etc., may or may not be a mutually exclusive algorithm or path (for the example shown, the algorithm is a not mutually exclusive for single finding or diagnosis). Note that because the method, or algorithm, shown and described in not mutually exclusive for each category (NEW ASC TAA, NEW DES TAA, NEW AAA, NEW ASC DIL, and NEW DES DIL), each category needs to be reassigned into separate NLP engine decoding tables for the method to execute as designed. Decoding table 368 is shown, as an example, of what is considered an incorrectly designed decoding table in the context of an algorithm for categories that are not mutually exclusive. (Decoding table 368 can be applied in different algorithms or decoding paths as necessary to identify, match, and assign a report as positive for a new aneurysmal (or vascular dilatation) location AAD in the context of an alternative diagnosis from a non-aortic dissection specific imaging protocol. In addition, the secondary color coding contains superimposed NLP or automated understanding. The cell background color, as shown in decoder table 368, refers to the identification and sub-classification based on two categories: aneurysm (blue cell fill color) versus vascular dilatation (yellow cell fill color) based on the finding or diagnosis. As examples, also represented are the use single character wildcards, here in place of numerical values, as identified during the decoding step for aneurysmal (or vascular dilatation) location. Numerical values can also be identified as how far away, in single character increments within an alphanumeric string in a cell, they are from a keyword such aneurysm (or positive AAD) to denote level of confidence in the identified value being associated with said keyword. An additional layer of NLP generated automated understanding can be derived from the technique as shown, if more than one sub-classification is decoded in a single examination, thereby representing a variably described single finding versus variably described additional finding(s), the dominant finding (or finding with the greatest number of decoded hits) can be represented by the secondary color coding (as shown, NEW DES TAA cells are blue fill color) when applied to the aneurysm location column (the column with the header title Aneurysm Location, in the example of AAD).

Referring now to FIG. 23B, a second representative screen shot of a NLP engine table (ANEURYSM LOCATIONS) is shown (note that the subclassifcation for NEW DES DIL in not actually represented). The engine table categorizes newly diagnosed aneurysms into following: ascending thoracic aorta, descending thoracic aorta, and abdominal aorta. The engine table also recognizes aortic dilatation locations not meeting aneurysmal size. The specific engine table displayed 369 is a continuation of 368 (refer to FIG. 23A). In reality, the two engine tables should be applied dynamically together as they collectively represent one large engine table (the entire engine table is too large to display on a single screen shot).

Figure 24:
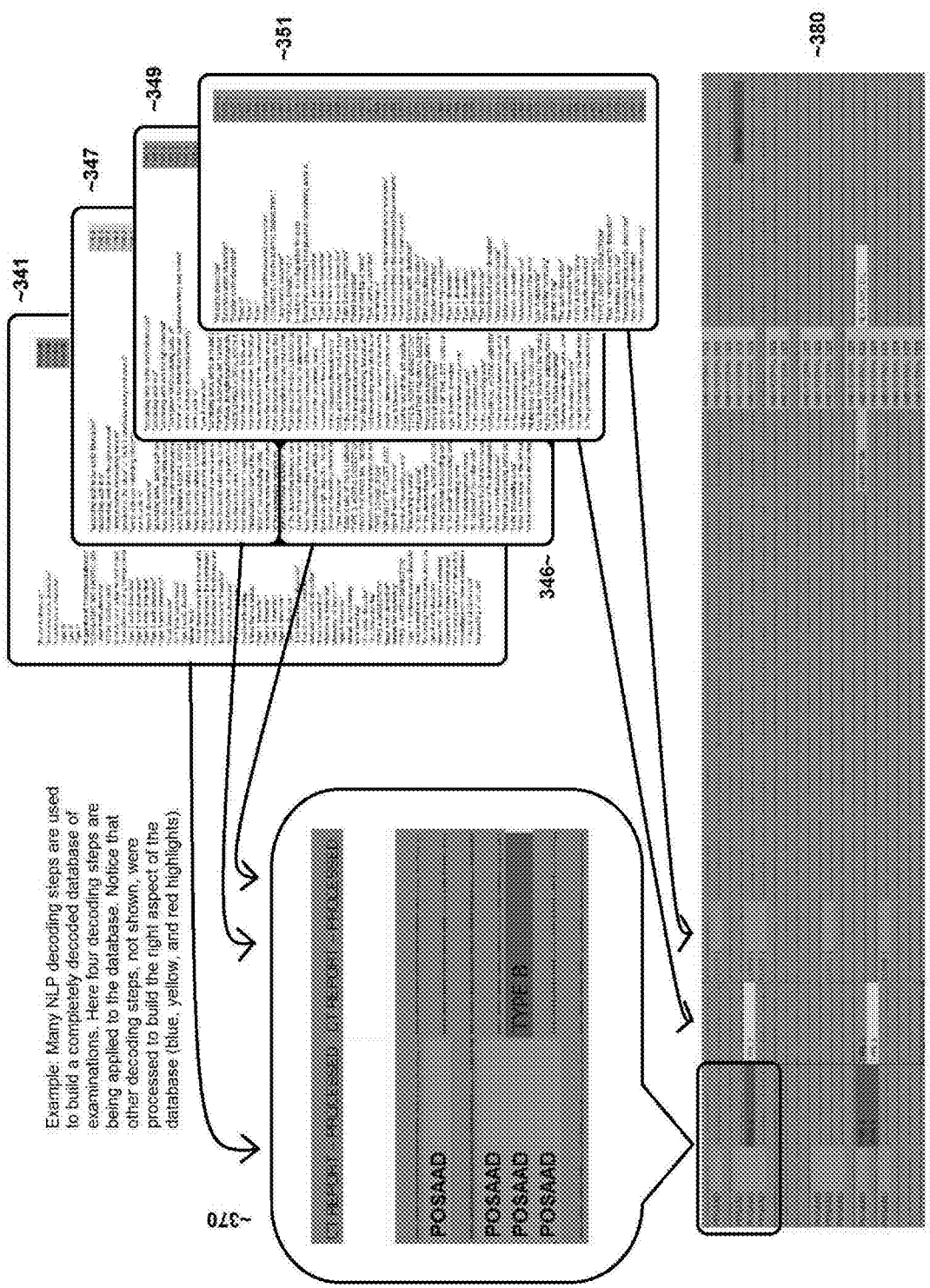
FIG. 24 is an illustration of a diagram showing an example of successive Stage 3 methods applied to multiple reports resulting in multiple color coded rows and columns, according to an embodiment of the present invention.

Referring now to FIG. 24, two minimized representative screen shots of two partial NLP engine tables (341, 346, 347, refer to FIGS. 13A and 14A for enlarged versions) as applied to a two column database corresponding to seven reports 370 (also refer to FIG. 11), are shown. The two column database, shown for simplicity and ease of understanding, represents a small section of a much larger database 380. Successive Stage 3 methods are applied to multiple reports resulting in multiple color coded rows and columns. As an example, four partial NLP engine tables are shown (341, 346, 347, 349, and 351, refer to FIGS. 13A, 14A, 15A, and 16 for enlarged versions) processing a larger representative section of the database 380 into decoded text with secondary color coding. As more columns containing parsed text are added to the database, more decoding steps can be applied. The result is a large database containing decoded text with secondary color coding 380 (refer to FIG. 25 for an enlarged version). Notice that other decoding steps, not shown, were processed to build the right aspect of the larger section of the database 380 (cells with blue, yellow, red fill color). The color coded cells enable downstream processing or visual programming. (Note that native text data (or alphanumeric string), text data (or alphanumeric string) without a decoded result, within each cell is not visible to the human eye because the text data (or alphanumeric string) remains minimized to improve downstream processing).

Figure 25:
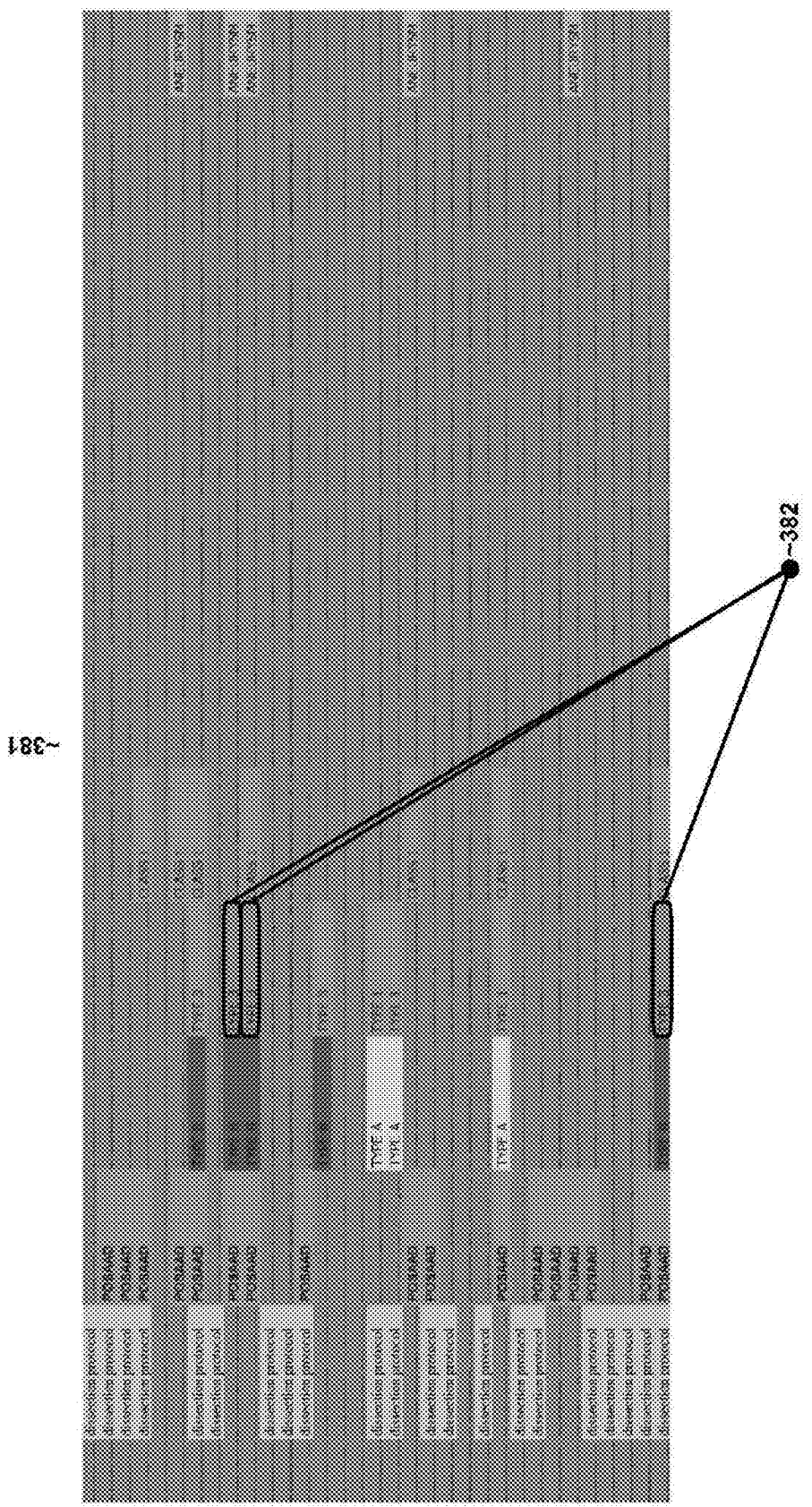
FIG. 25 is an example of a screen shot of a larger section of a database containing decoded text with secondary color coding, according to an embodiment of the present invention, noting that the actual completed decoded database is much larger, as only a small section is visible from a given standard computer screen.

Referring now to FIG. 25, a representative screen shot of a larger section of the decoded database 381 is shown. The section of decoded database 381 is shown containing several different columns, of many different reports or rows, of decoded text with secondary color coding. The actual completed decoded database is much larger. Even though decoded database 381 is enlarged compared to decoded database 380 (refer to FIG. 24), only a small section is visible from a given standard computer screen. Note that the exact sample section shown in decoded database 381 is of a different representative section than shown in decoded database 381 (refer to FIG. 24). The representative section of decoded database 381 is intentionally from a different section of the same decoded database as 380 to better illustrate the decoded text cells with secondary color coding, the larger text size is now readable. The change in color against the background orange color allows efficient identification of a working NLP engine as decoded text with secondary color coding. Alternatively, decoded text without the proper secondary color coding is difficult to identify efficiently illustrating the importance of secondary color coding. As an example, decoded text without proper secondary color coding is shown as "Type 3" with orange color coding against an orange color coded background (382). With reference and acclimation to 340, 380, and 381 (refer to FIGS. 10, 24, and 25) the reader can now appreciate the difference between NLP engine text decoding yields if 340 is considered as "no yield" (in reality the NLP engine was not applied to 340, if it was applied then the QA engineer should consider the possibility that the NLP engine was not executing properly), 380 is considered as "low yield," and 381 is considered as "high yield." The differences in NLP engine text decoding yields are only efficiently identified by the human eye by focusing on the secondary color coding. The color coded cells enable this method of human processing, or visual programming, during QA analysis or other manual analysis. (Note that native text data (or alphanumeric string), text data (or alphanumeric string) without a decoded result, within each cell is still not visible to the human eye because the text data (or alphanumeric string) remains minimized to improve downstream processing).

Referring now to FIGS. 11 through 25, or Stage 3 methods collectively, the natural tendency for radiology reporting (or clinical reporting in general) is not to identify a protocol/report as positive or negative for disease, instead the prose is intentionally somewhere in the middle of the spectrum for a variety of reasons (legal, knowledge base, certainty, examination quality, goal of examination, etc.). This creates difficulty for traditional NLP text decoding algorithms as the text to be decoded is not simply a binary result of positive or negative as in other forms of human language and medical information. The methods as described in FIGS. 11 through 23B address the problems not solved by other more traditional NLP methods or techniques.

As an example, the detailed steps for Stage 3: Natural language processor (NLP) engine (text decoder or translator) as applied to the radiology or medical language, are as follows:

1. Create a reference standard for comparison by manually searching previously verified and validated imaging reports to find key terms (these terms serve as the "find" phrases in the generic batch find and replace program). As an example, reference to the aortic dissection protocol MDCT database comprised of positive, negative, and indeterminate imaging reports derived from IDX 2002 (373 examinations) and IDX 2004 (475 examinations), previously verified and validated by a manual process, is hereby incorporated in subsequent steps as the reference standard.
2. Using the key terms identified in Step 1, create decoder tables (translation tables) as appropriate (as examples, decoder tables for positive, negative, and Type A aortic dissection protocol CT examinations).
3. Apply wildcard flanks to all key terms in the search column of each decoder table as follows (347, refer to FIG. 14A):
   a. As an example, the find term "ascending arch to the aortic bifurcation" appears as follows: "*ascending arch to the aortic bifurcation*" in row 1 in column A
   b. As an example, the replace term "Type A" appears as follows: "Type A" with any formatting specified (as an example, yellow cell fill color) in row 1 in column B
4. Starting from the end product (result) from Stage 2, the text (alphanumeric string) database containing parsed data, with the last column containing the processed reports to be decoded/translated, copy entire the column:
   a. As an example, consider the given spreadsheet database file name: aortic dissection protocol MDCT.xls containing column T in 290 (refer to FIG. 8), here column T contains one row of sample text data in row 2 (a single cell with a single Stage 2 processed report)
   b. Select column T data
   c. Copy column T data (as an example, Ctrl+C)
   d. Close said spreadsheet file (as an example, aortic dissection protocol MDCT.xls)
5. Open a new blank spreadsheet (as an example, temporary file.xls) and then paste copied column T from Step 4c into the said spreadsheet. Save file. Close file.
6. Download and install a generic batch find and replace program. As an example, Useful File Utilities Batch Replacer (UFU) for Microsoft (MS) Excel is hereby incorporated as reference as the generic batch find and replace program, all subsequent steps are specific to UFU execution (instructions available through UFU are hereby incorporated as reference for further detail).
7. Open generic batch find and replace program (UFU)
8. Follow generic batch find and replace program instructions and replace file with alphanumeric strings placed in decoder table (translation table), specifically:
   a. Enable the following options/settings:
      i. Browse to and then right click given file (spreadsheet or database, as an example, temporary file.xls from Step 6) to be decoded so that the file is highlighted red
      ii. Send selected file to basket (may or may not need this option enabled depending on program version)
      iii. Select "batch replacer for MS Excel"
      iv. Browse to appropriate translation table
      v. Select the following parameters: "whole cell" and search in "values"
      vi. Click "Advanced Options"
      vii. Check all appropriate options under "formatting for the replace with text" and set "Where to make changes" to "make changes in the original file and create backup file" or "save changes to a new file whose name is generated by the Mask:" and input the appropriate file name into the Mask: C:\desktop\temporary file.xls, and then Click "ok"
      viii. Click "Start Replace".
9. Reopen decoded spreadsheet file (as an example, resulting temporary file.xls from Step 8 sub-step vii) and then copy the decoded column (as an example, the decoded column is now located in column A), specifically:
   a. Select column A and then copy (Ctrl+C) within temporary file.xls
10. Reopen database file (as an example, aortic dissection protocol CT.xls from Step 4a) and then paste the decoded column A into column U in reference to 290 (refer to FIG. 8), or the next empty column to the right. Column U is now considered an NLP engine processed column compared to raw (non-decoded, but Stage 2 processed) text data in column T. Save updated database file.
11. Repeat Steps 4 and 5. There should now be a fresh copy of the processed reports in Column A to be decoded (translated) within a new file (as an example, temporary file. version2.xls).
12. Repeat Steps 7 through 10 while applying a different NLP engine decoder table as appropriate.
13. Repeat above steps as necessary to fulfill the number of desired decoding (translation steps). The end result is a completed database containing an unlimited number of decoded (translated) report columns that are ready for analysis using the Automated Analyzer, as described in Stage 4. In other words, in a repetitive and iterative fashion apply the created decoder tables (NLP engine tables) from Steps 1-3 by using a generic batch find and replace program to as applied to a text data (or alphanumeric string) database created by Stages 1 through 2. As an example, for aortic dissection protocol MDCT, 23 distinct decoder tables were created (refer to the detailed description of FIG. 8, and 340 through 369, refer to FIGS. 12 through 23B). The 23 distinct decoder tables represent 23 separate NLP decoding steps containing a total of 4821 iterative phrases to decode (translate) a given report with near 100% accuracy. The result is a completely decoded report that is automatically categorized into 23 separate categories (as an example, the category in question can be disease X, disease sub-category X, disease location X, disease timing X, disease size X, etc.) depending on the report findings. (Note the application of decoder tables using a generic batch find and replace program can be applied to either Stage 2 processed (restructured and parsed) reports containing delimiters or to Stage 2 unprocessed reports (thereby bypassing Stage 2) without delimiters; however, the capability of Stage 3 and 4 decreases when Stage 2 processing is not applied).
  a. As an example, first apply the negative decoder table, then apply the positive decoder table, and then apply the Type A decoder table, etc.
14. Verify the steps performed properly by visually identifying the secondary color coding changes, as previously described.

As an example, further detailed steps for Stage 3: Natural language processor (NLP) engine (text decoder or translator) as applied to the radiology or medical language, are as follows:
1. To increase the accuracy of the NLP engine (decoding/translation process) successive sub-steps are used to find the phrase in question and replace the "word", rather than the "cell", in an iterative fashion. (As an example, using UFU parlance setting the parameters to "whole word" rather than "whole cell"). The resulting cell (containing the multi-step decoded report) may have several "find phrases" corresponding to "replaced phrases." The summation of all of these "replaced phrases" within the single cell can be split in a binary fashion, as follows:
  a. If positive (as an example, the "replaced phrase" corresponds to positive for aortic dissection) the "replaced phrase" can be set to equal 1 (counted as 1 value).
  b. If negative (as an example, the "replaced phrase" corresponds to negative for aortic dissection) the "replaced phrase" can be set to equal 0 (counted as 1 value).
  c. The sum total of all "replaced phrases" can be calculated and divided by the total number of values ("1" or "0" replaced phrases) to yield a decimal (or fraction).
  d. The resulting decimal (or fraction) can be considered how positive or negative the overall report is for the finding category in question (as an example, the category in question can be disease X, disease sub-category X, disease location X, disease timing X, disease size X, etc.)
    i. 1.0=positive
    ii. 0.7=Likely positive
    iii. 0.5=indeterminate
    iv. 0.3=likely negative
    v. 0=negative
  e. The incorporation of these sub-steps to decode (translate) each finding category allows the approximation of actual meaning within a text report. This sub-step method allows decoding (translation) of reports even when the text contradicts itself in different areas within the same report (in instances of inaccurate voice transcription or typographical errors). The method also allows decoding (translation) of text when the report is intentionally vague in cases of truly questionable or indeterminate findings (typically referred to "hedging" by a radiologist).
2. To increase the accuracy of the NLP engine (decoding/translation process) successive sub-steps are used in an alternative approach compared to the concept described in Step 1 (refer to further detailed steps for Stage 3). Using an alternative approach, accuracy can be further improved by applying the sub-steps as described to the "whole cell" rather than the "whole word" (refer to the detailed description of FIG. 11). Using these parameters allows application of the previously described secondary color coding to be utilized. The downside to altering the parameters to "whole cell" when performing accuracy improvement is that a new (fresh, non-decoded) source text data column is required for each successive decoding step, and more importantly, only a single batch find phrase and replace phrase can be used at each decoding step.
3. To increase the accuracy of the NLP engine, a different step involving the counting of characters representing numerical values and counting how far away in terms of single character spaces they are from keywords can be applied, specifically:
  a. As an example, the numerical value "5" is seven characters away from the keyword "aneurysm" (or 9 spaces and characters away) in the following alphanumeric string ("5 cm sized aneurysm").
4. As an example, certain data is required in order to create billing code decoder tables. Typical billing codes are in reference to examination details defined in ADT data or imaging report headings (as an example, with or without contrast). When provided, the billing code can be used as source data to create standard "replace" phrases when the defined ADT "find" phrases are identified.
5. As an example, the capability and accuracy of the NLP engine can be verified and validated using aortic dissection protocol MDCT and the following steps:
  a. Using the reference standard aortic dissection protocol MDCT positive, negative, and indeterminate imaging reports derived from IDX 2002 (373 examinations) and IDX 2004 (475 examinations), previously verified and validated by a manual process, all 23 NLP decoding tables were applied to Stages 1 through 2 processed imaging reports from IDX 2002 and IDX 2004, as previously described in detail. The NLP engine results were highly accurate.
6. As an example, the broad and generalized capability and accuracy of the NLP engine can applied to renal stone protocol MDCT using the following steps:
  a. Create a reference standard for comparison by manually searching previously verified and validated imaging reports to find key terms (these terms serve as the "find" phrases in the generic batch find and replace program). As an example, renal stone protocol MDCT positive, negative, and indeterminate imaging reports derived from calendar year 2011 (257 examinations) and calendar year 2012 (300 examinations), previously verified and validated by a manual process, is hereby incorporated in subsequent steps as the reference standard.
  b. Using the reference standard from Step "a" containing renal stone protocol MDCT positive, negative, and indeterminate imaging reports, 10 NLP decoding tables were applied, using Steps 2 through 15 (refer to the detailed Steps for Stage 3), to Stages 1 through 2 processed imaging reports from calendar year 2011 (257 examinations) and calendar year 2012 (300 examinations) for renal stone protocol MDCT, while taking into account the appropriate alterations (the given protocol is renal stone protocol MDCT rather than aortic dissection protocol MDCT), as previously described in detail. The NLP engine results were highly accurate.

7. As examples, other categories, besides AAD classifications from positive aortic dissection protocol MDCT examinations or positive, negative, and indeterminate renal stone protocol MDCT examinations, that can be decoded are as follows:
   a. Demographics (DEMO) from ADT data within several reports types.
   b. Vital Signs (V/S) from clinical reports—an example of automated Blood Pressure (BP) analysis.
   c. Signs and Symptoms (Si/Sx) from clinical reports—an example of a variety of pain locations, and signs such as unequal BP in the upper extremities, with automated analysis.
   d. PMH from clinical reports—examples of automated analysis on medical syndromes such as Marfan's and Ehler Danlos, as well as a variety of surgical aortic repairs and valve repairs.
   e. Electrocardiogram (EKG) reports—example of automated analysis of associated EKGs. This also demonstrates the NLP engine decoder can be applied to non-imaging tests to extract understanding.
   f. Chest x-ray imaging reports (CXR)—Another example of the NLP engine decoder as applied on a different radiology examination.
   g. Surgical notes and reports.

It is to be understood, of course, that while the exemplary methods detailed above are performed manually, the methods themselves can be performed in a more automated fashion by writing a simple script or other piece of code.

Stage 4

Figure 26:
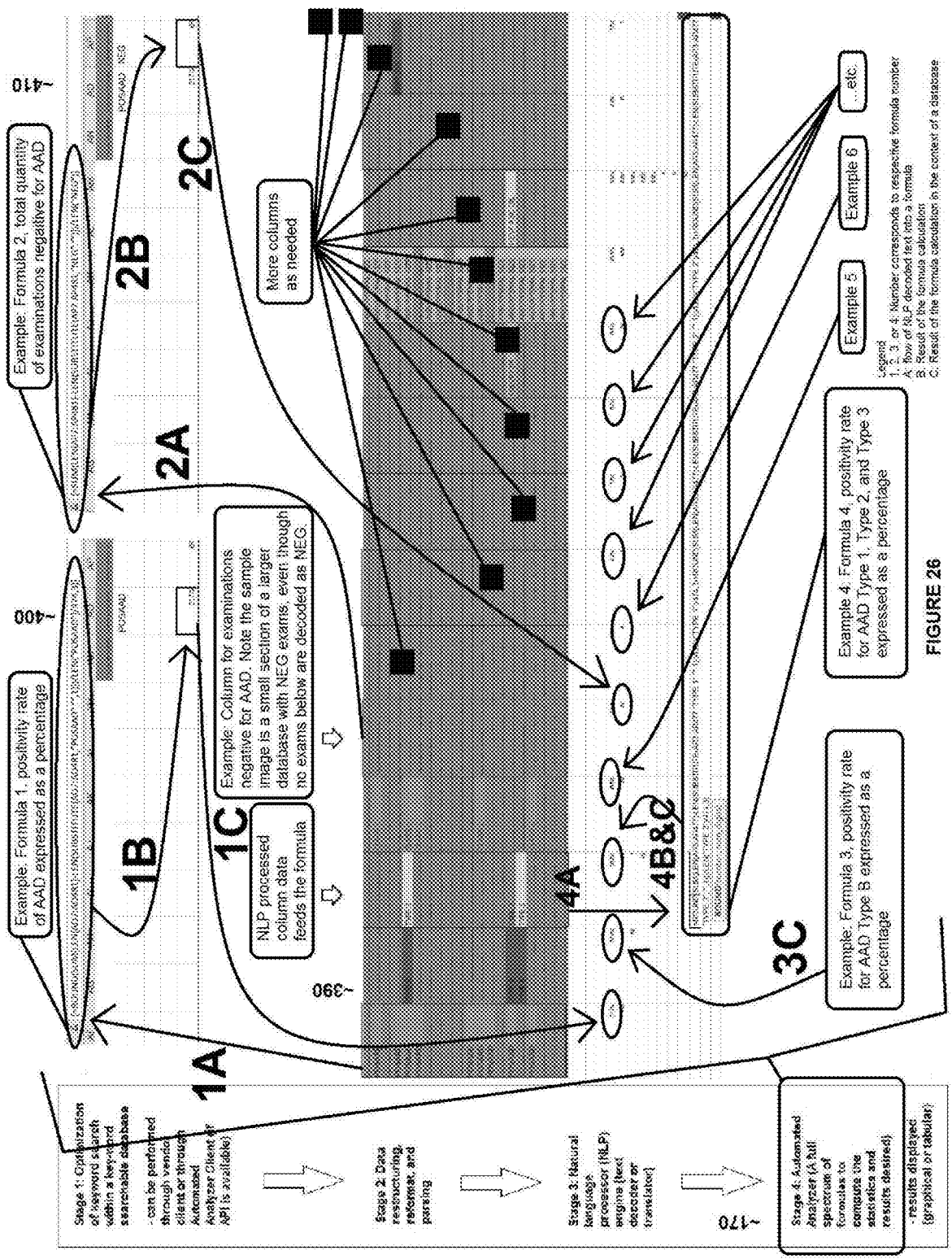
FIG. 26 is an illustration of a diagram showing an example of successive Stage 4 methods applied to a section of a decoded database, according to an embodiment of the present invention.

Referring now to FIG. 26, a comprehensive diagram with representative examples of successive Stage 4 methods (170) as applied to a section of a decoded database 390, is shown. The section of decoded database 390 shown is actually the same database section in 380 (refer to FIG. 24) with the addition of several example formulas displayed surrounding the database 400 and 410 (refer to FIG. 27 for enlarged versions). Several example formula results are also shown below database 390 (refer to FIG. 28 for an enlarged version), as applied to the entire decoded database (too large to practically illustrate). As an example (400), an entire column of decoded text within the database is fed into formula 1 (1A), analyzed by formula 1 (1B), and then the result is displayed (1C). As an additional example (410), an entire column of decoded text within the database is fed into formula 2 (2A), analyzed by formula 2 (2B), and then the result is displayed (2C). As sample portions of additional examples, the result from formula 3 analyzing a different decoded column is displayed (3C), the result from formula 4 analyzing yet another decoded column is displayed (4A, 4B, to 4C), and so on and so forth. As more columns containing parsed text are added to the database, and more decoding steps are applied, more advanced automated analytics can also be applied. The result is a large decoded database with a variety of automated analytics 390 (refer to FIG. 28 for an enlarged version). (Note that native text data (or alphanumeric string), text data (or alphanumeric string) without a decoded result, within each cell is not visible to the human eye because the text data (or alphanumeric string) remains minimized to improve downstream processing).

Figure 27:
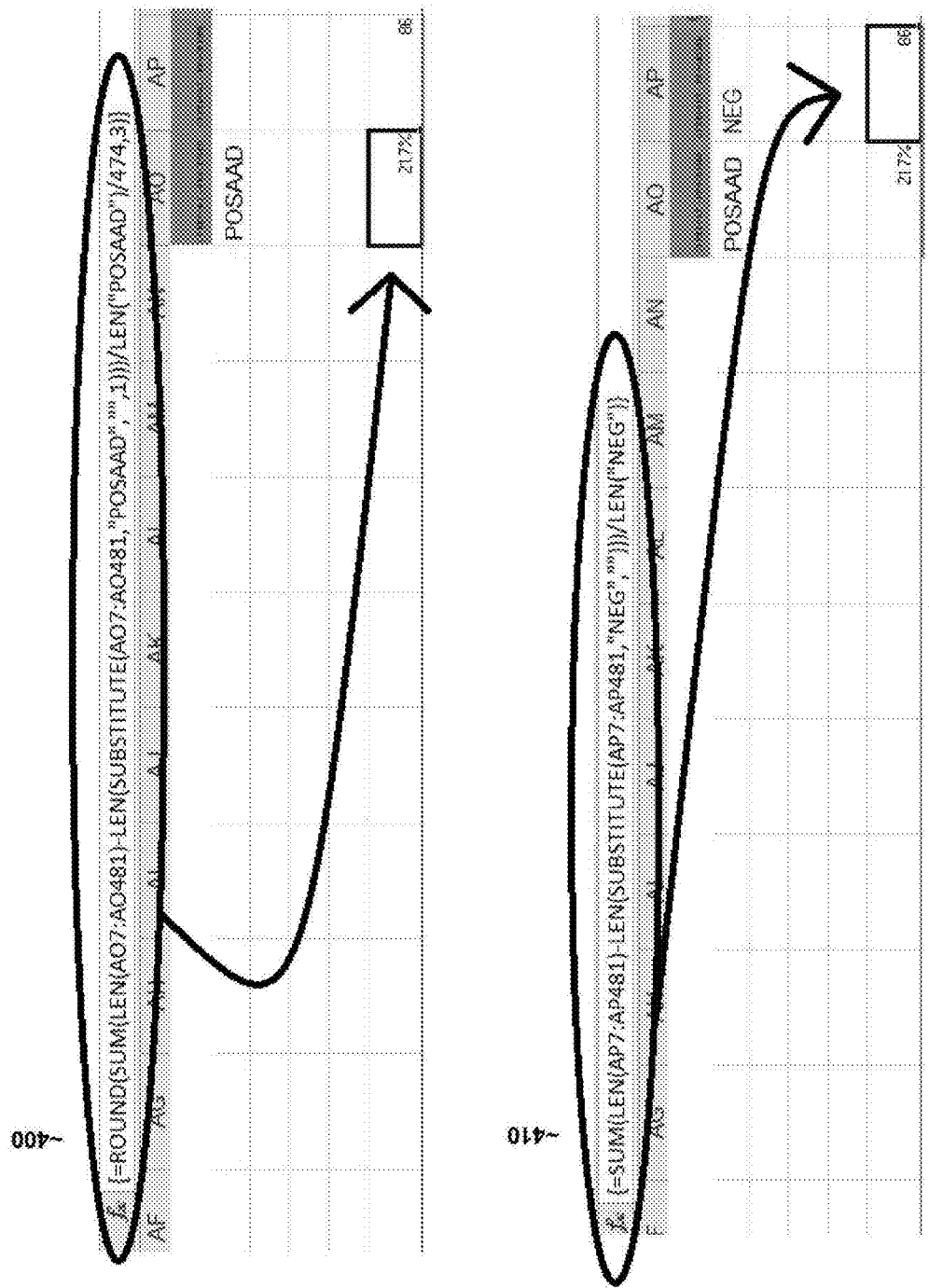
FIG. 27 are examples of screen shots of formula 1 and formula 2, according to an embodiment of the present invention.

Referring now to FIG. 27, two representative screen shots of two example formulas, formula 1 (400) and formula 2 (410), are shown. Formula 1 and formula 2 are outlined and diagramed while analyzing the decoded text within the database. Specifically, formula 1 (400) analyzes decoded text for the positivity rate of AAD and displays the result as a percentage. Further, formula 2 (410) analyzes decoded text for examinations negative for AAD and displays the result as a number.

Figure 28:
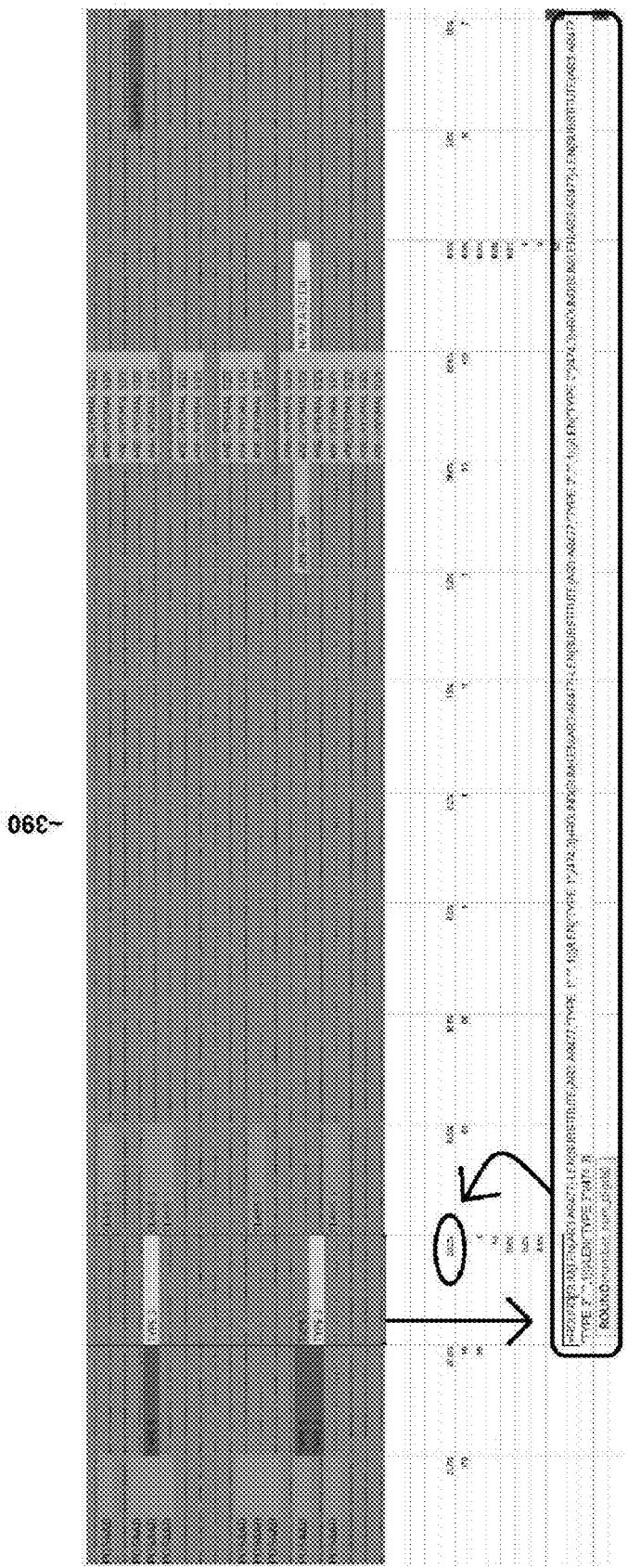
FIG. 28 is an example of a screen shot displaying a variety of formula results as displayed below a section of a decoded database, according to an embodiment of the present invention.

Referring now to FIG. 28, a representative screen shot displaying a variety of formula results below a section of a decoded database (390), is shown. Specifically, formula 4 (4A, 4B, & 4C, refer to FIG. 26) is enlarged and outlined to display the flow of Stage 4 analytic processing: NLP decoded text data (or alphanumeric string) is delivered to the formula, the data is analyzed, and then the result is displayed.

Figure 29:
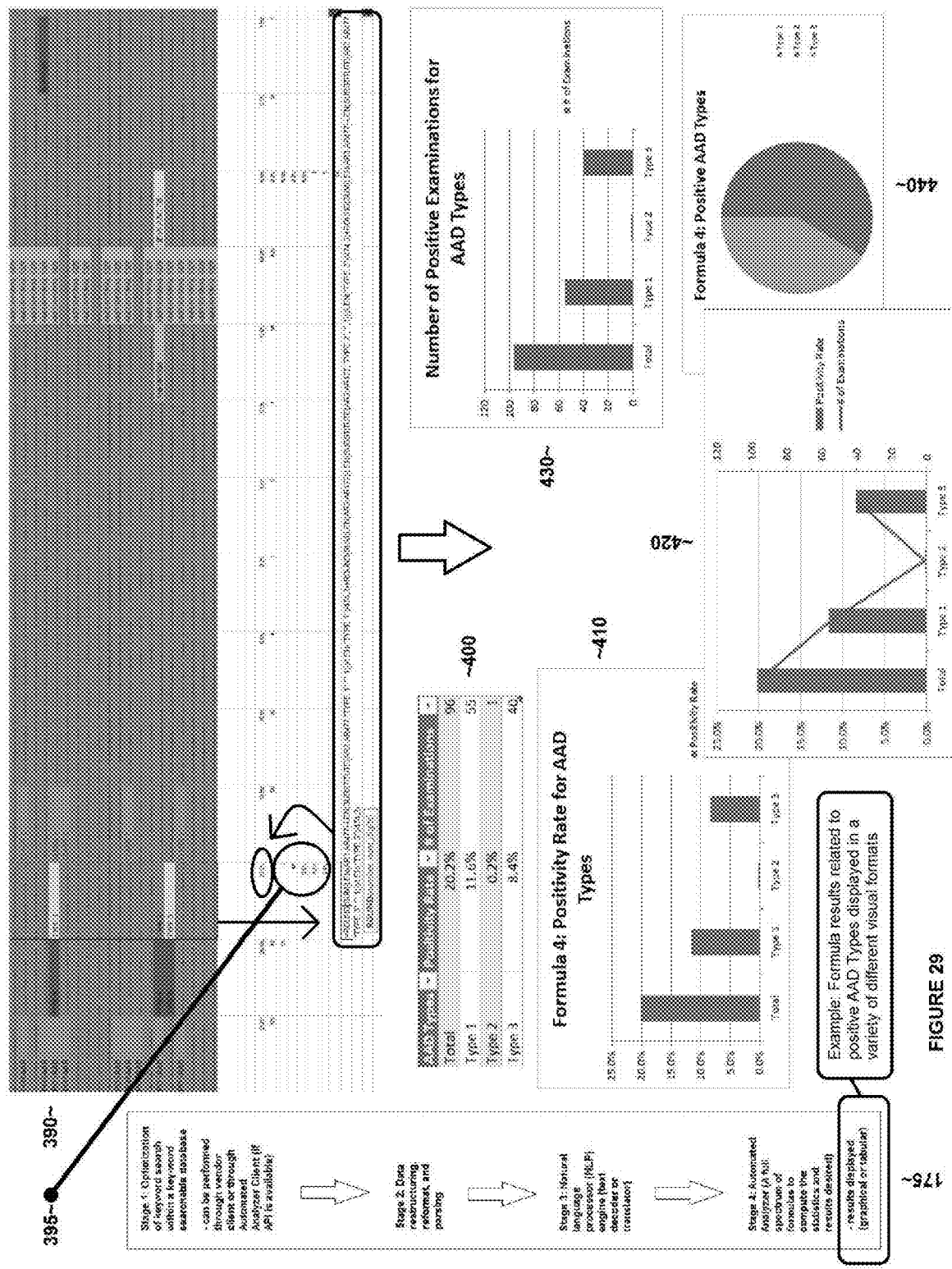
FIG. 29 are examples of screen shots displaying sample tabular and graphical visual representations of the variety of formula results as displayed below a section of a decoded database, according to an embodiment of the present invention.

Referring now to FIG. 29, several representative screen shots displaying sample tabular and graphical visual representations (175) of the variety of Stage 4 formula results as displayed below a section of a decoded database (390), are shown. As examples, the result from formula 4 (refer to FIGS. 26 and 28) and the results from related formulas (395) can be visually displayed as a color table, a color bar graph with percentages, a color combination bar/line graph with percentages and numbers, a color pie chart, or a color bar graph with only numbers. The visual representation of automated Stage 4 analytics enables additional understanding of the results.

Referring now to FIG. 30, several representative tables showing 2×2 contingency tables for Multi-Detector CT (MDCT) imaging protocol validation (450 and 460), are shown. Specifically, positive, indeterminate, and negative MDCT examination are shown in a 2×2 matrix (450) with corresponding odds, likelihood ratios, and probabilities (460). As an example, three "Judgment Calls" (refer to FIG. 30) are shown in progress: (1) Assign a pre-test probability: Should you image a patient using the Aortic Dissection Protocol MDCT if your pre-test probability is 25%? (2) Set cut-off: set Intermediate and Positive MDCT tests as the cut-off (consider my patient as a positive test if found to be in one of these categories). (3) Set threshold for decision change: Threshold will be set at 90%, because surgery is not benign. Now, using Bayes' Theorem: the Pre-test probability is 25%=0.25, Pre-test odds=p/1−p=0.25/1−0.25=0.33, Post-test odds=pre-test odds×LR. Also set LR=Likelihood ratio derived from validation data given our cut-off where LR=a/a+c/b/b+d=disease/no disease=sensitivity/1−specificity. Now calculate the LR for all test result categories (refer to FIG. 30). Using these LR's you can calculate the resulting post-test odds of disease where Post-test probability=posttest odds/1+posttest odds. Now interpret the results. Since we considered either an Indeterminate or Positive MDCT as a Positive Case we will add the post-test probabilities of the two. 0.99+0=0.99=99%. Since our cut-off for outcome change was 90%, this result is important. The important point is, using our three Judgment Calls and Validation Data for MDCT, that the post-test probability of Positive Disease given our criteria positive (Pos) or indeterminate (Indeterm) for a test result is 99%. Since our first Judgment Call was a pre-test probability of 25%, and our third Judgment call for treatment was a cut-off of 90%, the fact that a proper result on the test can boost this probability of 25% to 99% is significant. This ability of a Positive or Indeterminate test result on MDCT to change our treatment plan provides sufficient evidence to warrant the use of MDCT imaging protocol in question. In other words, the usual process of diagnosis involves data retrieval, assigning of relative importance to each data point, and then deriving a differential diagnosis. Each diagnosis in the differential diagnosis list is excluded one by one as assessment using experience based diagnostic "feelings" and/or "impressions" regarding a patient's evaluation is processed (subjective data).

Referring now to FIG. 31, several representative tables for treatment decision making analysis according to a loss matrix (470 and 480) and an opportunity loss matrix (490), are shown. Progression of logic is shown as flowing from 470, to 480, and to 490. As an example, the total probability in population P(A)=0.95 and P(B)=0.05 with a Patient Power indifferent up to $1000 loss is displayed in 470 and 480. The use of an opportunity loss matrix (490) in decision making helps with identification of AVOIDABLE losses that do not change the optimal decision. According to the analysis in 490, the optimal choice for Cause A is no treatment (No Tx), but for Cause B is treatment (Tx), when opportunity cost is factored into the decision making process.

Referring now to FIG. 32A, a representative table for test utilization in decision making analysis according to factoring in probability assessment as applied to a loss matrix (500), is shown. Progression of logic is shown flowing in 500. In the example of the first test (500), given the probabilities shown, the cheaper decision for a positive test is to provide treatment and for a negative test is not to provide treatment. Consider a lab test that costs $10 where Sensitivity=85% and Specificity=90%. Now referring to 500, the Expected Value of the Test=Cheapest Decision for each Test Result×Probability=($63.45×0.1375)+($20.38× 0.8625)=$26.31. However, the Expected Value of not utilizing a Test=$35.95.

Referring now to FIG. 32B, a representative table for test utilization in decision making analysis according to factoring in probability assessment as applied to a loss matrix (510), is shown. Progression of logic is shown flowing in 510. In the example of the second test (510), given the probabilities shown, the cheaper decision for a positive test is still to provide treatment and for a negative test is still not to provide treatment. Note the fact that the optimal choice according to the two example loss matrices did not change even though the sensitivity and specificity for the first test (500) and the second test (510) are drastically different. However, the sensitivity and specificity of a test still provides the basis for the optimal choice. Consider a lab test that costs $30 where Sensitivity=100% and Specificity=100%.

Now referring to 510, the Expected Value of Test=(0.05× $80)+(0.95×$35)=$37.25. The test shown, second test can be considered a perfect test based on the high sensitivity and specificity. Therefore the expected value of the second test is $37.25, of the first test is $26.31, and of no test utilization is $35.95. Further, consider the concept of a cost free Perfect Test where the expected value of such as test is $7.25. Using logic, a physician would likely turn $7.25 into an Opportunity Loss, where no test utilization would have an expected value of $28.70 (this represents the most one should pay for a perfect test as it was an Opportunity Loss).

Referring now to FIG. 32C, a representative table for test utilization in decision making analysis according to factoring in probability assessment as applied to a loss matrix (520), is shown. Progression of logic is shown flowing in 520. In the example of the third test (520), given the probabilities shown, the cheaper decision for a positive test is to not provide treatment and for a negative test is also not to provide treatment. Note in comparison the first test 500 and second test 510 (refer to FIGS. 32A and 32B) the optimal choice did change as the sensitivity and specificity for the test shown (520) is different. Even though the sensitivity and specificity of a test still provides the basis for the optimal choice, cost combined with total population probabilities remains considerations. Now consider a third test with a Cost=$1, Sensitivity=60%, and Specificity=60%. Now referring to 510, the Expected Value of this third test=(0.41×$51.18)+(0.59×$26.42)=$36.57. In comparison, the expected value of the second test was $37.25, the first test was $26.31, and no test utilization was $35.95. Remembering that value is the same as cost, the overall optimal choice now becomes the first test 500 because no test is free of cost.

As an example, the detailed methods for Stage 4: Automated Analyzer (A full spectrum of formulas to compute the statistics and results desired), are as follows:

Stage 4 involves a full spectrum of formulas to automatically calculate desired statistics and results (as an example, these formulas can be written as functions and stored in excel to be later applied to spreadsheets in an automated fashion as each spreadsheet in is created from Stage 3: NLP engine). Work originally performed on various files dated Dec. 11, 2005 to Mar. 27, 2006. The formulas can be calculated without a unit of time as a denominator to provide an overall rate without reference to time. A given calculation can refer to the total tabulated within a database irrespective of time. As an assumption, 0.1% is standard for inadequate for a variety of reasons, usually a technical limitation. (As an example, improper timing of contrast administration during imaging protocol scan acquisition). With reference to Automated Analyzer Follow-Up, in instances where patients who did not have a the scan in question, a surrogate maker can be searched for including but not limited to imaging, operation/procedure/surgical note, clinical note of death, etc.

Array Formulas as applied within the Automated Analyzer—Array formulas to perform this automation were created. Positivity rate and number of negative scans were automatically calculated. As an example 400 (refer to FIG. 27), the following formula was used to auto-calculate the positivity rate for Positive Acute Aortic Disorders (POSAAD).

1. =ROUND(SUM(LEN(AO7:AO481)-LEN(SUBSTITUTE(AO7:AO481,"POSAAD","",1)))/LEN("POSAAD")/474,3)

As an example 410 (refer to FIG. 27), the following formula was used to auto-calculate the number of negative scans (NEG).

2. =SUM(LEN(AP7:AP481)-LEN(SUBSTITUTE(AP7:AP481,"NEG","")))/LEN("NEG")

Modification and improvement to Array Formulas—Improved automated calculation run where total positive acute aortic disorders (POSAAD) was 37.8%. The POSAAD decoder was checked for accuracy by comparing the decoded results against a verified and validated reference standard, and subsequently found to be highly accurate.

Further improvement of NLP engine and the Automated analyzer—Analyzing decoded radiology language into a percentage using a single-cell one-dimensional vertical array formula. On Oct. 27, 2006, found that Aortic dissection protocol MDCT use increased each subsequent year. The acute aortic disorder positive scan rate in 2004 was 37.8%

Sample size determination for reference standard statistical significance—Formula to required sample size or number of report to achieve necessary error bound B and a 95% confidence interval, to verify number of examinations needed within the reference standard for statistical significance. Given a defined positivity rate of 18% from the previously published 2002/2003 database (whereby reference to the following is now incorporated, Radiology. 2006 March; 238(3):841-52. Epub 2006 February 1.). Further, hereby reference to Information Technology, Learning, and Performance Journal. 2001, 19(1) 43-50 is now incorporated for mathematical details:

---

1. B = error bound = 1/sq (N)
2. if N = 400, then B = 5% with 95% CI
   V = variance = 18% as above
   N = sample size needed
   B = Error bound
3. N = 4V/B pwr2 = 4(.18)/.05 power (2) = 388 sample size for 95% CI
   or
   B = 5%
   N = 400 gives B = 5% or CI = 95%
4. B = error bound = 1/squareroot (N)
   if N = 400, then B = 5% with 95% CI

---

Automated Analyzer—imaging protocol verification (post imaging protocol A examination)—The NLP engine can be applied to a database to find/replace any mention of acceptable terms defining the desired imaging protocol A. The NLP engine can then be applied an additional time to a copy of the database to find/replace mention of inadequate/incomplete imaging protocol A examinations (as an example, the aortic dissection protocol CT requires first a non-contrast scan, and then a contrast scan). The resulting databases from steps "a" and "b" can compared, combined, then be parsed/coded into (A) reports from the desired imaging protocol A that were adequately completed and (B) reports from other undesirable imaging protocols or inadequate/incomplete imaging protocol A examinations. The reports from any other undesirable imaging protocols or inadequate/incomplete imaging protocol A examinations can either be deleted from the database or ignored from all subsequent analysis. As an additional measure of quality control, the use of a variety of phrase "find" iterations to define imaging protocol A can be employed if inadequate application of Stage 1 methods were utilized. As examples, aortic dissection protocol MDCT and AAA protocol MDCT. Note that this fact alone can be exploited in instances where a pre-existing keyword searchable database does not exist and cannot be used to search a clinical database. The generic power of Stages 2 through 4 can override the deficit of Stage 1.

Automated Analyzer—Appropriateness Gauge (pre or post imaging protocol A examination)—This capability allows automated indication (Chief Complaint (CC), history, clinical history, history of present illness) analysis for requested/written imaging protocols. Note that many of these methods as described can also be applied to an Automated Analyzer Follow-Up, as described below. The NLP engine can be applied to a database containing imaging reports and clinical notes to extract acceptable indications PRIOR to (in a real-time manner) performing an imaging protocol. In a similar fashion, the decoding engine can be applied to a database containing imaging reports and clinical notes to extract acceptable indications AFTER (in a retrospective manner) performing an imaging protocol. Acceptable indications for an imaging protocol can mirror standard criteria as published in the literature. The results for the decoded imaging protocol indication can then be subjected to successive steps (as mentioned previously, Stage 3, Step 11-d) to find the phrase in question and replace the word, rather than cell, in an iterative fashion. The resulting cell (containing the multi-step decoded report) may have "several phrases" corresponding to "replaced phrases." The summation of all of these "replaced phrases" within the single cell can be split in a binary fashion (as mentioned previously, Stage 3, Step 11-d) providing a decimal "grade" of how likely the indication is based on how many times "the find phrase" is mentioned throughout the clinical record (emergency medicine note, clinic notes, consultant notes, admission notes, etc.) immediately preceding the requested imaging protocol in chronological time. This allows the percentage grading of each acceptable indication (by ACR appropriateness criteria, as an example) for the requested imaging protocol to be analyzed in an automated manner either before, or after, the requested imaging protocol is completed. The analyzed results can be combined and displayed as an overall "appropriateness gauge" for the imaging protocol in question to any individual (requesting physician, referring physician, radiology technician, radiologist, etc.) to serve as a quick check if the imaging protocol is meets standard appropriateness criteria. As an example, some ordering physicians do not order the appropriate radiologic examination based on the indication provided. As an example method, the terms "CT head" for an indication of either Cerebrovascular Accident (CVA) or mass can be searched and the terms "MR head" for an indication of either CVA or mass can be searched. As an example method, all emergency patients with clinical symptoms and signs suggesting appendicitis during 2008 and 2009 can be searched as applied to the EMR. As an example method, cross-reference MR examinations performed with the indication provided by the ordering physician; A subset of MR examinations performed, such as Magnetic Resonance Cholangiopancreatography (MRCP), can be compared to the indication provided. As an example method, ER orders for radiologic examinations include well defined indications, ER orders for admission and discharge also include well defined diagnoses, sometimes the indications for radiology examination and final diagnoses for admission and discharge are discrepant therefore the indication within the radiology report can be compared to the ER admission and discharge diagnoses. As examples of actionable results obtained from the methods described, (A) The resulting data can help provide feedback to referring physician who routinely order inappropriate examinations based on the indication. (B) Overall improvement in patient care will be supported by ensuring only appropriate examinations are performed. (C) The results are also mandatory for the formulas in the automated positivity gauge category and automated validation imaging protocol A category to function appropriately and accurately. (D) The resulting data will demonstrate how frequent the indication for a radiologic examination and the admission or discharge diagnoses are discrepant and appropriate action can be taken to ensure the ER does not order radiologic examinations when they are not indicated.

Automated Analyzer—imaging protocol gauges—The capability is based on the fact that imaging protocols are designed to accurately diagnose one particular disease or spectrum of diseases (as an example, aortic dissection protocol CT) unless the imaging protocol design is generalized to focus on speed, efficiency, and screening for a wide spectrum of unrelated diseases (As an example, non-contrast protocol CT of the abdomen and pelvis in emergency cases with little to no preceding clinical workup). Positive scan rates (positivity rates) can be generated for all imaging protocols, provided the design intent is understood. To simplify creation of positivity rates, all imaging protocols can be categorized as positive or negative for an abnormal finding, this allows for extraction of serendipitous identified positive findings (those findings that are either not the focus of the protocol or non-acute in timing of disease). In addition, the concept of stability is used in radiology when an imaging finding is similar in characterization when compared to any prior imaging. This can be searched for to further sub-categorize positive imaging findings. As an example, aortic dissection protocol CT is designed to diagnose acute aortic diseases (AAD) including aortic dissection, intramural hematoma, penetrating aortic ulcer, aortic aneurysms, and aortic rupture. All of the diseases may be identified in any combination and at any time point on the natural disease course. The natural disease course is usually categorized as acute, sub-acute, or chronic. Further, serendipitously identified diseases such as Renal Cell Carcinoma (RCC) may be diagnosed, but the protocol designed is not optimized to properly and completely diagnose this disease. Regardless, the finding and partial diagnosis of RCC made possible by using the aortic dissection protocol CT can allow the overall imaging examination to be categorized as a positive scan, however positive for a chronic finding and/or an alternate finding/diagnosis. This alternate diagnosis may or may not actually represent the source/etiology of the patient's Chief Complaint or correspond to the referring physician's original indication for ordering the imaging protocol. The radiology literature suggests that these alternative findings be categorized as alternate diagnoses and as positive scans, but clearly labeled as positive scans for alternative diagnoses, not positive for disease A when the imaging protocol B is not designed to properly and completely diagnose that given disease A (as an example, imaging protocol B is designed to diagnose disease B, not disease A).

Automated Analyzer—imaging protocol performance rate—This capability is based on calculating the imaging protocol accuracy as compared to a reference standard (as an example, aortic dissection protocol CT compared to surgical reports and/or pathology reports).

Automated Analyzer—imaging protocol performance gauge—This capability is based on calculating the imaging protocol accuracy as compared to a reference standard (for gauge normalization, hereby normalization applies to all subsequent reference to gauges).

Automated Analyzer—requested/written imaging protocol positivity gauge—This capability is based on calculating the requested/written imaging protocol positivity rate as compared to a reference standard.

Automated Analyzer—imaging protocol positivity gauge—This capability is based on calculating the imaging protocol positivity rate as compared to a reference standard. This gauge may only be relevant for advanced imaging protocol such as MDCT and magnetic resonance imaging (MRI).

Automated Analyzer—imaging protocol overall positivity gauge—This capability is based on calculating the imaging protocol overall positivity rate as compared to a reference standard.

Example formulas/functions include:
1. Actual quantity of requested/written imaging protocol A=(quantity of requested/written imaging protocol A)−(accepted standard % for inadequate imaging protocol A×quantity of requested/written imaging protocol A)−(quantity of requested/written imaging protocol A that did not have imaging protocol A performed)
2. Actual quantity of requested/written imaging protocol=quantity of requested/written imaging protocol that was actually scanned or completed
3. Actual quantity of requested/written imaging protocol A/quantity of requested/written imaging protocol A=Performance rate for requested/written protocol A Performance rate for requested/written protocol A also referred to as "imaging protocol performance rate" or "imaging protocol performance gauge."

4. Number of positive scans from imaging protocol A/Actual quantity of requested/written imaging protocol A=Positive scan rate for imaging protocol A Positive scan rate for imaging protocol A referred to as positivity rate for imaging protocol A, "imaging protocol positivity rate," or "imaging protocol positivity gauge."

5. Positive scan rate for imaging protocol A+Positive alternative diagnosis rate for imaging protocol A=Overall positive scan rate for imaging protocol A="imaging protocol overall positivity gauge"
6. Number of positive scans from imaging protocol A/quantity of requested/written imaging protocol A=Positive scan rate for requested/written imaging protocol A Positive scan rate for requested/written imaging protocol A referred to as positivity rate for requested/written imaging protocol A, or "requested imaging protocol positivity rate," or "requested/written imaging protocol positivity gauge."

The result "positivity rate for requested/written protocol A" can be limited or expanded in scope:

7. If limited to a referring physician: positivity rate for requested/written protocol A=positivity rate for requested/written protocol A for that particular referrer=Referrer positivity rate
8. Referrer positivity rate=Referrer positivity gauge for imaging protocol A As examples, the utilization (positivity rate) of imaging protocols by ordering/referring physician. As an example method, appendicitis protocol CT can be searched for and the positivity rate identified. As example results, the values obtained can be limited to radiologist X, department X, hospital X, referring physician, etc. As an example method, lower extremity protocol CT (in the setting of trauma) is trending towards over-utilization as a result of the ease of ordering CT to rule-out a highly morbid condition after negative radiographs, indeterminate radiographs, or no prior imaging. As example results, the values obtained can be limited to radiologist X, department X, hospital X, referring physician, etc.

Automated Analyzer—referral tracking—This capability is based on referrer imaging protocol A scan volume. As conceptual examples, radiology administration and marketing managers do not want to wait an entire month or quarter to identify decreases in referrals of high-dollar modalities such as MRI and CT. As a conceptual example, departmental chairmen want to be able to identify physicians who over-utilize or underutilize imaging protocols in their diagnostic evaluations. As an example method, search, restructure/parse, decode, and analyze (Stages 1-4) to identify all referring clinicians by volume, date and modality. As examples of a method and the result, in Quality Improvement (QI) and/or Quality Assurance (QA) for referring physicians on imaging protocol use Stages 1-4 and identify referring physicians who order unnecessary imaging protocols for simple headache as identified in the EMR. As examples of a method and the result, Stages 1-4 can be used to identify referring physicians who order pulmonary embolism protocol CT without prior documentation of moderate or high pre-test probability of disease. As examples of a method and the result, Stages 1-4 can be used to identify avoidance of routine pre-operative chest radiographs in ambulatory patients with an unremarkable history and physical examination. As examples of a method and the result, Stages 1-4 can be used to identify and encourage avoidance of appendicitis protocol CT in patients less than 18 years old without initial consideration of ultrasound examination. As examples of a method and the result, Stages 1-4 can be used to identify and encourage avoidance of follow-up imaging protocol examination of uncomplicated clinically incidental adnexal cysts.

Automated Analyzer—Referrer scan volume for imaging protocol A—This capability is based on referrer scan volume for imaging protocol A, the result contains important trend information. The scan volume is a surrogate marker for the combined effects of the personal threshold for requesting imaging protocol A, the clinical severity, and the true incidence of disease in the given population.

9. Referrer scan volume="threshold for request/written imaging protocol A"+clinical severity+true incidence of suspected disease
10. If limited to a radiology department: positivity rate for requested/written protocol A=positivity rate for requested/written protocol A for that particular radiology department=radiology department positivity rate
11. Radiology department positivity rate=radiology department positivity gauge for imaging protocol A
12. Imaging protocol A scan volume trends over a given period of time within the same population (department, as an example) demonstrate either referrer threshold changes, clinical severity changes (a random change), or true changes in incidence of disease within a population.
13. If limited to a region or city: positivity rate for requested/written protocol A=positivity rate for requested/written protocol A for that particular region or city=Regional or city positivity rate
14. Regional or city positivity rate=regional or city positivity rate for imaging protocol A When "A" is defined as a given disease entity (as an example, aortic dissection) then the following can be applied: If this imaging protocol A has had proper validation study performed, then the regional or city positivity rate can serve as a surrogate marker for the incidence of disease A in that particular region or city. In this context, incidence is defined as the number of new instances of disease A per unit time in that particular region. If this imaging protocol has had proper validation study performed, then the Regional or city positivity rate can serve as a surrogate marker for the prevalence of disease A in that particular region or city. Whereby prevalence is defined as the total number of disease cases A in that particular region. If the positivity rate for requested/written protocol A from hospital X is compared to the positivity rate for requested/written protocol A from hospital Y, the difference can be calculated:

15. (positivity rate for requested/written protocol A from hospital X)−(positivity rate for requested/written protocol A from hospital Y)=positivity rate difference The closer the positivity rate difference is to zero, the more equivalent the utilization for imaging protocol A are for hospital X and hospital Y. Whereby the positivity rate for requested/written protocol A from hospital X is referred to as the "imaging protocol A utilization rate from hospital X." The positivity rate for requested/written protocol A from hospital Y is referred to as the "imaging protocol A utilization rate from hospital Y." The difference is referred to as the "imaging protocol A utilization rate difference between hospital X and hospital Y." As an example, the difference in utilization rate between hospitals can serve to demonstrate where imaging protocol is over-utilized, under-utilized, or appropriately utilized when three or more hospitals are compared.

16. (Total quantity of requested/written imaging protocol A from hospital X)−(Total quantity of requested/written imaging protocol A from hospital Y)=utilization difference of imaging protocol A between hospital X and hospital Y The result "positivity rate for imaging protocol A" can be limited or expanded in scope:

17. If limited to radiologist Z: positivity rate for imaging protocol A=positivity rate for imaging protocol A for radiologist Z=Total positivity rate for radiologist Z for imaging protocol A
18. If limited to radiologist D: positivity rate for imaging protocol A=positivity rate for imaging protocol A for radiologist D=Total positivity rate for radiologist D for imaging protocol A Now we can compare either the total positive scans (when the actual quantity of requested/written imaging protocol A read is not given) and/or the total positivity rate (when the actual quantity of requested/written imaging protocol A read for radiologist D and radiologist Z is given) for radiologist D and radiologist Z for imaging protocol A.

19. (Total positive scans for radiologist Z for imaging protocol A)−(Total positive scans for radiologist D for imaging protocol A)=Total positive scan difference between radiologist Z and radiologist D for imaging protocol A Now we can compare the total positivity rate for radiologist D and radiologist Z for imaging protocol A.

20. (Total positivity rate for radiologist Z for imaging protocol A)−(Total positivity rate for radiologist D for imaging protocol A)=Total positivity rate difference between radiologist Z and radiologist D for imaging protocol A The concept can be expanded to create a reading radiologist Receiver Operating Characteristic (ROC) curve for QI purposes when the positivity rate and negativity rate are plotted.

21. Imaging protocol positivity rate for department (per year) compared to radiologist ROC
22. Imaging protocol positivity rate for department (per year) compared to ER physician imaging protocol utilization Automated Analyzer—process for validation of each imaging protocol—This capability is based on a method to address problems with defining sensitivity, specificity, positive predictive value, negative predictive value, and accuracy for each imaging protocol, in an efficient manner. When Stages 1-4 are applied to given imaging protocol with comparison to a more accepted reference standard such as findings within a surgical or pathology report, the validation can be performed.

Automated Analyzer—problems with defining "requested/written imaging protocol A"=suspected cases (patients) disease A. This capability is based on the following assumption that some referring physicians favor speed for patient evaluation at the expense of appropriate imaging. The result is that some requested/written imaging protocol A has no clinically appropriate indication to undergo imaging protocol A. So even though inadequate imaging protocol A+performed imaging protocol A=requested/written imaging protocol A, this is not the total cases of suspected disease A. Even though using logic the aforementioned holds true mathematically, but human error does occur and the requested/written imaging protocol is not appropriate for the suspected disease. This error effects the Automated Analyzer validation of imaging protocol A. Specifically, the error alters positivity rate or positive scans for imaging protocol A. To adjust for the concept of "inappropriate indication", the adjusted formula is:

23. inadequate imaging protocol A+performed imaging protocol A=requested/written imaging protocol A
24. (reasonable CC/indication)/(requested/written imaging protocol A)=appropriate requested/written imaging protocol A Now more accurate calculations for validation imaging protocol A can be performed. Now calculate automated positivity rate or positive scans imaging protocol A with 2×2 contingency statistics and accuracy compared to reference standards (any follow-up imaging, surgical notes, pathological notes, clinical notes, etc.) When a given imaging protocol A is not considered to be the diagnostic reference standard for disease A, an automated validation analysis of the imaging protocol can be performed by comparing the entire database (hospital, department, clinic . . . etc.) of imaging protocol A to the EMR. By working backwards from the specific imaging protocol A examination identified in the original analysis to create the total positivity rate, the same Medical Record Number (MRN), or patient name, can be used to identify the corresponding record in the EMR. Once this correlation is completed, an analysis of the entire clinical record for that MRN/patient/case can be decoded and analyzed for disease A by applying the NLP decoding engine to the EMR. Specific areas that would be analyzed include, but are not limited to, all follow-up/subsequent imaging, surgical notes, pathology notes, clinical notes, discharge summaries, discharge diagnosis, discharge International Classification of Diseases (ICD) codes, etc. This analysis allows automatic creation of a 2×2 contingency table and calculation of the overall accuracy for a diagnosis for a given imaging protocol A after all corresponding MRN/patient/cases are analyzed. The resulting 2×2 contingency table defines the number of true positives, false positives, false negatives, and true negatives for that particular imaging protocol when assessing for disease A. The result is an automated process for validation of each imaging protocol.

The aforementioned concept of error introduced by inappropriate requested/written imaging protocol A can also be applied to the concept of error introduced by inadequate imaging protocol examinations as well (as an example, when a non-contrast examination is performed when a contrast examination is appropriate). If the same concept to automate the validation statistics for an imaging protocol is limited in scope and only applied to particular radiologists, a 2×2 contingency table, and overall accuracy for a diagnosis, for that radiologist can be created. Specifically, when limited to radiologist Z for imaging protocol A, the number of true positives, false positives, false negatives, true negatives, and overall accuracy can be defined. Automation of above the described process for a summative ROC curve and/or overall accuracy analysis for diagnosis A for radiologist Z can then be applied. When the same concept is applied to every imaging protocol radiologist Z reads, a series of data points corresponding to sensitivity (true positivity rate) and (1—specificity, or false positivity rate) can be created and plotted where sensitivity corresponds to the Y axis and (1—specificity) corresponds to the X axis. In a similar fashion, Positive Predictive Value (PPV) and Negative Predictive Value (NPV) can be calculated. The result is automated and summative ROC curve, and overall accuracy for diagnosis A, for radiologist Z.

25. Where PPV=true positive/(true positive+false positive)
26. NPV=true negative/(true negative+false negative)

When same concept is expanded in scope to department Z for imaging protocol A, the number of true positives, false positives, false negatives, true negatives, and overall accuracy can be defined for department Z. When the same concept is limited in scope and applied separately to each radiologist for a given department (as an example) for given imaging protocol A, a series of data points corresponding to sensitivity (true positivity rate) and (1—specificity, or false positivity rate) for each radiologist for imaging protocol A can be created and plotted where sensitivity corresponds to the Y axis and (1—specificity) corresponds to the X axis. In a similar fashion, Positive Predictive Value (PPV) and Negative Predictive Value (NPV) can be calculated (as shown above). The result is automated and summative ROC curve for imaging protocol A for the entire department. In other words, a location specific sensitivity and specificity for a given imaging protocol can be created and automated, thus allowing referring physicians to see real time what the true value of an imaging protocol is prior to ordering/requesting the imaging protocol for a patient. When this information is provided and taken into consideration with the pre-test probability of disease A (or pre-test odds) for given patient/case, most of the biostatistics in medicine become far more usable and can realistically guide further guide medical decision making in real-time. Further, a 2×2 contingency table, and overall accuracy can be defined for department Z. The primary limitation of the above methods of creating an imaging protocol positivity gauge is that projection of the resulting data to other populations may be confounded by a different incidence rate for a given disease.

Automated Analyzer—Automated follow-up analysis—This capability is based on the fact that the result "positive scans from imaging protocol A" can be categorized according to each positive scan (MRN/patient/case). Each patient (MRN/patient/case) can then have their EMR searched for any corresponding follow-up (including imaging protocol A, any other imaging protocol, clinical notes, emergency medicine notes, surgical or procedural notes, pathology notes, etc.) data mined (searched) for the same (or similar) diagnosis using the NLP decoding engine. Those patients (MRN/patient/case) without follow-up of any kind can be identified (especially when diagnosis A is considered life-threatening or potentially life-threatening at a more advanced stage). Once identified, these patients can be referred back to the original corresponding referrer, a new more appropriate physician, insurance provider, or even a family member for follow-up clinical or surgical care as needed. As examples, diagnoses with potential need for further follow-up diagnostic imaging or interventional radiology procedures:

27. Osteoporosis screening such as Dual-Energy X-ray Absorptiometry (DEXA) scanning in the elderly
28. Inferior Vena Cava (IVC) filter placement follow-up (cases for that lack needed placement or follow-up for potential removal
29. Abdominal aortic aneurysm or other acute aortic disorder without follow-up diagnostic imaging or vascular repair
30. Following up imaging on pulmonary nodules of appropriate size or imaging characteristics based on standard criteria
31. Follow-up on mammographic imaging (MAM)
32. Diagnoses identified from a search of the entire EMR without the following recommended neurosurgical/orthopedic procedural care (as examples, discectomies, laminectomies, vertebral corpectomies, and insertion/repair of neurostimulators)

Patients diagnosed as obese, or as having elevated an Body Mass Index (BMI), or elevated body weight, without a history of the following possible procedures can be identified by searching the entire EMR and referred back to the Primary Care Physician on record or other appropriate caregiver to potentially have the following procedures performed (if necessary after appropriate consultation). As examples, hernias (epigastric/incisional/inguinal), laparoscopic cholecystectomies, and laparoscopies (gastric banding).

Patients diagnosed with high grade orthopedic disease (such as high grade Anterior Cruciate Ligament (ACL) injury, as an example) by clinical or imaging examinations after searching the EMR with the NLP decoding engine who do not have clinical, surgical/procedural, or imaging follow-up after a given period of time can be identified and referred back to the original referring physician, primary care giver, or other appropriate care giver. As examples, femorotibial joint pathology, glenohumeral joint pathology, and bone tumors.

Patients identified from a search of the entire EMR/RIS/PACS with known clinical or radiologically diagnosed disease severity warranting imaging or procedural follow-up care. As examples, diagnoses with potential need for further follow-up diagnostic imaging or interventional radiology procedures. As an example, an automated virtual safety net can be created using Stages 1-4 to identify cases for QA Coordinator/Clerical Support/Referring Clinician where both immediate and 12 month follow up is warranted. As an example, using Stages 1-4 a virtual referral analyzer can be created for patients with risk factors for a high morbidity or mortality disease can be identified by a keyword search of the EMR/RIS/PACS and follow-up can be provided by alerting the Primary Care Physician (PCP) of recommended diagnostic or interventional care. In addition, recent and emerging recommendations can be added and included. As a detailed example, patients with known risk factors for Alzheimer's disease (advanced age, family history, etc.) can be identified and new recommendations for Positron Emission Tomography (PET) screening can sent to the PCP 33. After identifying Imaging protocol A positive cases (as detailed above)→look for positive cases without any form of follow-up As an example, using Stages 1-4 the term carotid ultrasound and percentage (grade) stenosis can be identified. As an example, diagnoses identified from a search of the entire EMR without the following recommended neurosurgical/orthopedic procedural care. As an example, diagnoses of risk factors such as smoking in males over the age of 65 (65-75) without AAA screening in the HIS/EMR can be flagged and referred back to their PCPs for need of appropriate diagnostic imaging for disease prevention/screening. Patients diagnosed as obese without a history of weight reducing procedures can be identified by searching the entire EMR and referred back to the PCP to have the procedures performed. Patients diagnosed with high grade orthopedic disease after searching the EMR with the NLP decoding engine who do not have any follow-up after a given period of time can be identified and referred back to the original referring physician.

As an example, using Stages 1-4 to identify follow-up imaging in EMR/PACS/RIS for a given patient, the results can be compared to the prior imaging report for agreement/concordance. This concept does not require the same exact prior imaging protocol as the initial imaging protocol may be designed for screening only. Further, the same exact imaging protocol may not always be performed by the same department across hospitals. As an example, cardiac imaging may not be performed in radiology, sometimes Transthoracic Echocardiogram (TTE) or Transesophageal Echocardiogram (TEE) is done by cardiology in a separate database and fed via HL7 into the EMR.

Automated Analyzer—prevention analyzer—This capability is based on referring to known well established prevention imaging recommendations as a knowledge base. As a detailed example, using Stage 1-4 to identify men with the following parameters: a given age, and known smoker, coupled with this a search within the radiology PACS/RIS for lack of needed imaging. The results can be the basis for referrals to radiology for AAA ultrasound imaging (US) (or a DEXA scan for women, MAM, etc.) The results serve as both Quality Improvement and increased reimbursement/incentives for diagnostic imaging departments or hospitals.

Automated Analyzer—Automated disease progression tracker—This capability is based on disease diagnosed in radiology reports in a patient-centric manner, (as an example, comparing prior radiology report to a more recent radiology report). As an example, cross-reference bone scan results with Prostate-Specific Antigen (PSA) levels. First incorporate a separate patient laboratory database containing PSA levels, where the term PSA can be searched, then the term bone scan be searched in PACS/RIS. The results can be cross-referenced to compare bone scan results with PSA levels thereby improving radiology report quality overtime through QA measures.

Automated Analyzer—Automated ionizing imaging protocol repetition tracker. This capability is based on redundant and/or unnecessary radiology procedures ordered, leading to overexposure to the patient and potentially uncompensated costs. An appropriate need for follow-up warrants escalation of communication efforts to guarantee the patient receives care. As an example method, using Stages 1-4 to identify all reports with "Recommend Follow-up" in the Impression section, the results can be quickly scanned for appropriateness of findings. Those radiologists or referring clinicians with undesirable trends can be identified and coached for improvement. Further, patient follow-up can also be incorporated at this point. As an example, using Stages 1-4 identification of "standards of follow-up" can be defined for radiologic examinations for a given diagnosis. As an example, patients with known nephrolithiasis can be analyzed to determine the average number of follow-up examinations over a 3 month period. As an example method, using Stages 1-4 to identity the term nephrolithiasis and the resulting examinations over a 3 month time frame can be further analyzed based on how many follow up examinations were performed and the results can then compared. The results will demonstrate the range in the number of follow-up radiologic examinations and help define the average. A guideline to help future follow-up examinations can be implemented.

Automated Analyzer—unnecessary follow-up—This capability is based on the fact that patients identified from a search of the entire EMR/RIS/PACS with an immediate history of interventional surgical procedure and with negative clinical or imaging protocol follow-up may not need further imaging or clinical follow-up. As an example, using Stages 1-4 to identify post percutaneous Transthoracic Needle Biopsy (TNB) patients who do not reveal a pneumothorax immediately post procedure and the results can be analyzed for trends for procedures where the current standard for imaging protocol follow-up may be unnecessary. As an example result, if all of the above TNB cases have negative long-term imaging follow-up with or without short-term nurse monitoring, then both short-term imaging protocol and long-term imaging follow-up may be considered unnecessary.

Automated Analyzer—Automated radiation dose tracker—This capability is based on tracking radiation dose levels over time or tracking radiation dose levels per examination will improve patient safety as this data is not currently monitored routinely, however is extremely important given recent high profile hospital failure and lawsuits nationally.

34. Automated imaging radiation dose tracker per patient (for accumulated dose)

Automated Analyzer—Radiation trends—This capability is based on accumulated radiation dose to ensure safe radiation dosage levels by tracking patients who have had multiple scans performed over the course of three months. A determination if all the scans were necessary is made and a determination if CT is over-utilized in the emergency room/setting (ER) is made. As examples, the following imaging protocols can be assessed: Renal Stone protocol CT, Pulmonary Embolism protocol CT, and CVA protocol CT. As an example method, using Stages 1-4 to identify the following parameters over a three month period, patients where the above imaging protocol were used, referring physician, and disease progression. The following function/formula is then applied:

35. Accumulative radiation dose/patient/time=Ensuring safe radiation dosage levels by tracking patients who have had multiple scans performed over the course of given time period
36. Radiation exposure per examination compared to expected levels As an example, the resulting data may show that some spikes in imaging are necessary for tracking disease progression in the ER, but other spikes are caused by different physicians ordering similar studies. Appropriate administrative action can then be taken based on actual "in house" hospital data, not outside published data.

As an example, radiation exposure or examination QI/QA where the correct amount of radiation exposure is important. In order for a chest radiograph to be diagnostic, a certain amount of radiation is needed. Too little yields a non-diagnostic exam. Too much yields a non-diagnostic exam and unnecessary patient exposure. As an example method, using Stages 1-4 to identify the radiation dose for each examination in the DICOM, over a given time period, each examination can be categorized as utilizing too little, appropriate, or too much radiation. As an example of the results, Quality Assurance for appropriate patient exposure during chest radiographs can be analyzed. Further, appropriate action can be taken to improve or maintain chest radiograph Quality Assurance.

37. Automated imaging radiation dose for desired range

As an example, using Stages 1-4 to identify fluoroscopic examinations (FL) that result in highest patient radiation exposure over a given time period both the final fluoroscopic time and the final patient radiation dose in units of dose area product (yGy*m2) can be calculated. As an example of the results, the examinations with both the highest fluoroscopic time and radiation dose can be presented to the appropriate personnel to improve awareness regarding high risk procedures that historically result in higher fluoroscopy times and radiation doses to help reverse radiation trends.

Automated Analyzer—imaging efficiency measures (primarily outpatient)—This capability is based on imaging efficiency as compared to known standards. As an example, mammography follow-up rates have a defined appropriated level. As an example method, using Stages 1-4 to identify patients with a Diagnostic Mammography or Ultrasound of the Breast study following a Screening Mammography Study, the resulting percentage can be calculated. Using these results, a reading radiologist's inability to adequately determine when additional imaging is necessary can be determined.

38. Mammography Follow-Up Rate=Patients with a Diagnostic Mammography or Ultrasound of the Breast Study following a Screening Mammography (given time period)/Patients with a Screening Mammography study As an example, using Stages 1-4 to identify contrast use during Abdomen CT the resulting percentage of contrast to non-contrast examinations can be calculated. As an example result, a higher value indicates a high use of contrast examinations and raises questions of inefficient ordering of imaging protocols. Note this concept only applies to screening protocol examinations.

39. Percentage of contrast enhanced Abdomen CT=The number of Abdomen CT studies with contrast (or combined with and without contrast)/The number of Abdomen CT studies performed (with contrast, without contrast, and both combined)

As an example, using Stages 1-4 to identify contrast use during Chest CT the resulting percentage of contrast to non-contrast examinations can be calculated. As an example result, a higher value indicates a high use of contrast examinations and raises questions of inefficient ordering of imaging protocols. Note this concept only applies to screening protocol examinations.

40. Percentage of contrast enhanced Chest CT=the number of Thorax CT studies with contrast (or combined with and without contrast)/the number of Thorax CT studies performed (with contrast, without contrast, or both combined)

Automated Analyzer—Centers for Medicare & Medicaid Services (CMS) Quality Measures—This capability is based on meeting known reporting requirements for reimbursement. As an example, using Stages 1-4 to identify and analyze the following terms: (A) MRI and Low back pain, (B) CT with contrast and without contrast, (C) CT with contrast and without contrast in patients over 60 years old, and (D) mammogram in patients over 60 years old. These results can then be compared to any follow-up examinations corresponding to the same patient over a given time frame where the call-back rate can be calculated. As an example, using Stages 1-4 the terms breast ultrasound and probably benign in the same report can be identified and the rate of breast ultrasounds with the impression of probably benign can be calculated. As an example, using Stages 1-4, the terms CT and MRI head for an indication of either CVA or mass can be identified and positivity rates calculated. As an example, using Stages 1-4 the terms pneumothorax, lung biopsy, and thoracentesis can be identified and positivity rates calculated. As an example, using Stages 1-4 the terms contrast extravasation can be identified. As an example, using Stages 1-4 the term carotid ultrasound and % stenosis can be searched where positive cases can be categorized as to how the positive findings are reported (which criteria are used).

Automated Analyzer—Automated imaging protocol costs—This capability is based on the fact that a disease can diagnosed by multiple imaging protocol and all costs can be rounded to the nearest dollar using the Arithmetic Rounding algorithm. As reference for the following, the Disease to be diagnosed is "disease C" by either "imaging protocol A" or "imaging protocol B." Using this concept, the following formulas/functions can be applied:

41. Actual hospital cost per imaging protocol=actual variable direct cost per unit+actual fixed direct cost per unit+actual fixed indirect cost per unit
42. Actual hospital cost per imaging protocol×quantity of cases/unit time=Actual hospital cost for imaging protocol to evaluate suspected cases during a given unit time
43. Where quantity of cases=# of cases the imaging protocol was requested by a referring physician, Unit time=calendar year (as an example)
44. Actual hospital cost for imaging protocol A to evaluate suspected cases during a given unit time−Actual hospital cost for imaging protocol B to evaluate suspected cases during a given unit time=difference in imaging protocol cost during a given unit time
45. (Actual hospital cost per imaging protocol A)×(quantity of cases/unit time)/positive scan rate=Actual hospital cost for diagnosing disease C using imaging protocol A during a given unit time
46. (Actual hospital cost per imaging protocol B)×(quantity of cases/unit time)/positive scan rate=Actual hospital cost for diagnosing disease C using imaging protocol B during a given unit time
47. Actual hospital cost for diagnosing disease using imaging protocol A during a given unit time)−(Actual hospital cost for diagnosing disease using imaging protocol B during a given unit time)=Cost difference of diagnosing disease using imaging protocol A compared to imaging protocol B during a given unit time=Imaging cost savings to diagnosis disease C Automated Analyzer—Automated imaging protocol billing/coding—This capability is based on the fact that billing errors include not billing for all examination performed or billing for the wrong examination results in lost revenue within the department of radiology. As an example method, using Stages 1-4 to identify the radiologic examination as routinely reported within the "examination" or "study" header within the radiology report and the type of radiologic examination (imaging protocol A, as an example) is also included within the examination field entered by the radiology technician available through the RIS/PACS. The billed examination is located in a separate field based on ICD coding. Then identify the examination performed and compare this to the type of examination actually billed for chest CTs during a given time period. As an example method, using Stages 1-4 to identify the type of MRI examination performed in included within the radiology report as compared to the type of MRI examination billed in included with a separate billing database. The results containing discrepant billing can be presented. The comparison of examinations performed and billed examinations will assure appropriate billing and avoid lost revenue. Further, measures can be implemented to improve MRI billing when the exact causes of incorrect billing are identified.

Automated Analyzer—decrease professional/general liability risk exposure and increase quality of medical care/ Quality Improvement (QI)—This capability is based on meeting known Quality Improvement and Quality Assurance initiatives (QI/QA). As an example, detailed case logs for all radiology residents are a national requirement. As an example method, using Stages 1-4 to identify all modalities by time frame, by body part, and by radiologist the results can automatically serve as a case log. This information can be placed into a spreadsheet and organized by level of detail required.

Automated Analyzer—Centers for Medicare & Medicaid Services (CMS) Physician Quality Reporting Initiatives (PQRI)—This capability is based on the fact that CMS Physician Quality Reporting Initiatives (PQRI) reporting is currently accomplished manually at most hospitals. As an example method, using Stages 1-4 to identify the terms "Fluoroscopy time" can be searched during a given time period and the results can be categorized by examination type and then analyzed for each examination category. As an example method, using Stages 1-4 to identify the terms "breast ultrasound" and "probably benign" can be searched during a given time period and the rate of breast ultrasounds with the impression of "probably benign" can be calculated. When data from a reference billing department database during the same time period is used as a comparison standard, the accuracy can be analyzed. As an example method, using Stages 1-4 to identify the terms MRI and Low back pain, the terms CT with contrast and without contrast, the terms CT with contrast and without contrast in patients over 60 years old, and the terms mammogram in patients over 60 years old can be identified.

As an example method, using Stages 1-4 to identify Stroke and Stroke Rehabilitation as applied to CT or Magnetic Resonance Imaging (MRI) Reports where the percentage of final reports for CT or MRI studies of the brain performed either: (A) In the hospital within 24 hours of arrival or (B) In an outpatient imaging center to confirm initial diagnosis of stroke, transient ischemic attack (TIA) or intracranial hemorrhage are calculated. This concept can be applied to patients aged 18 years and older with either a diagnosis of ischemic stroke, TIA, intracranial hemorrhage, or at least one documented symptom consistent with ischemic stroke, TIA, or intracranial hemorrhage that includes documentation of the presence or absence of each of the following: hemorrhage, mass lesion, and acute infarction.

Automated Analyzer—documentation of radiology exposure time in reports for procedures using fluoroscopy—This capability is based on the fact that the analyzer can decode numerical values. As an example method, using Stages 1-4 the percentage of final reports for procedures using fluoroscopy that include documentation of radiation exposure or exposure time can be calculated. As an example method, using Stages 1-4 to identify the inappropriate use of "Probably Benign" assessment category in mammography screening the percentage of final reports for screening mammograms that are classified as "probably benign" can be calculated. As an example method, using Stages 1-4 to identify in Nuclear Medicine the correlation with existing imaging studies for all patients undergoing bone scintigraphy by calculating the percentage of final reports for all patients, regardless of age, undergoing bone scintigraphy that include physician documentation of correlation with existing relevant imaging studies (e.g., x-ray, MRI, CT, etc.) that were performed. As an example method, using Stages 1-4 to identify stenosis measurement in carotid imaging studies by calculating the percentage of final reports for all patients, regardless of age, for carotid imaging studies (neck MR angiography [MRA], neck CT angiography [CTA], neck duplex ultrasound, carotid angiogram) performed that include direct or indirect reference to measurements of distal internal carotid diameter as the denominator for stenosis measurement.

Automated Analyzer—Automated preliminary radiology report discrepancy tracker—This capability is based on the analyzer decoding and analyzing discrepant reports when created by a non-attending radiologist. This will ensure finalized impressions are reported to ordering physicians will improve communication/hand-offs to ordering physicians and provide an easy method to monitor further Quality Improvement in radiology report communication. As an example, report discrepancies (preliminary reports) between radiology resident and radiology attending the results can be categorized and presented for tracking preliminary radiology report discrepancies to ensure finalized impressions are reported to ordering physicians. As an example method, using Stages 1-4 to identify key text describing a report as discrepant the entire PACS database can be searched during a given period to analyze the frequency of discrepant reports. The results can be categorized according to post graduate year in training to help residents and fellows identify areas of weakness for continued improvement, improve accuracy in preliminary reports, and improve departmental and hospital administration confidence in the QA of radiology resident reports.

An as example, analysis of the severity of discrepant resident reports with respect to changes in patient management using a standard Radiology Peer Review System (RADPEER) scoring system on a group of cases with discrepant diagnostic interpretations and to compare these data with published norms. In the RADPEER system, a score of 1 is defined as agreement between radiologists, a score of 2 is a difficult diagnosis not expected to be made, a score of 3 is a diagnosis that should be made most of the time, and a score of 4 is a diagnosis that should be made almost every time. The overall percentage of discrepant reports can then be compared to published norms and further simplified into "under-reads" to "over-reads."

Automated Analyzer—Key Performance Indicators (KPI)—This capability is based on the analyzer calculating on-going metrics, or outcome measures, for achieving Quality Improvement (QI). Lapses in performance can have consequences of increased cost and increased patient morbidity and mortality. Often it is difficult to identify problems, consequences, implement changes, and reassess for improvement in a measurable fashion. Some common KPIs are: (A) Contrast reactions, screening, and treatment (B) Contrast extravasations, appropriate IV placement, follow-up, and treatment (C) Pneumothorax after a procedure (as an example, the terms pneumothorax, lung biopsy, and thoracentesis can be identified with Stages 1-4) (D) Emergency Department Turn-Around-Times, emergency imaging protocol completion rate (not all ordered imaging protocols are completed [refer to previous description of performance rate for requested/written protocol A], read, and reported to the ED physician within a given time frame), and stroke protocol imaging standard compliance and (E) Report accuracy rates with recognition software reporting errors such as the words "ascending" and "descending" and "no" vs. "new".

Overview of the Application of Bayes' Theorem within the Automated Analyzer—All tests have limitations. Given a pre-test probability (a subjective measure) while factoring in the probability of the opposite conclusion. Using this method, the probabilities are accounted for while factoring in the objective limits of the test in question given known data from prior validation studies. The result is a post-test probability given this test specific objective data. The goal is to objectify a subjective number to aid in the appropriate utilization of a given test. Once the post-test probability is calculated you can make a more informed decision on using a particular test. Three judgment calls need to be made prior to using this theorem: What is the pre-test probability (as an example, 25%)? What is the cut-off to be applied to the validation data of the test (an example, Intermediate cases+ Positives cases=consider as positive)? What is your threshold for an outcome change (as an example, in the case of medical tests, treatment vs. no treatment)? (As an example, treatment only if post-test probability is 80% or higher for disease). Overall, the result provides realistic guidance for medical decision making, possibly in real-time.

Basic concepts used in medical diagnosis can be simplified into three steps and applied within the Automated Analyzer—First, the symptom complex, or patient presentation. Second, medical knowledge is primarily obtained through validation studies showing a given diagnosis and the spectrum of symptoms and signs that result. Third, the application of Symbolic Logic (see below).

Two Mathematical Disciplines Used in Medical Diagnosis—Symbolic Logic and Probability as applied with the Automated Analyzer. For symbolic logic, the relationship between datasets is often illustrated with a Venn diagram in which sets are represented by regions in a plane. For two sets S and T that are not separate and are not a subset of the other, the intersection can be described as /S∩T/ (refer to any standard mathematical text for a full description). This counting method is called the general addition rule for two sets where the yield is four combinations of attributes. For probability, the total probability equals the ratio of the number of patients with the attribute in question to the total number of randomly selected patients. And conditional probability refers to the ratio is to a subpopulation of patients. The fundamental problem is as follows: Medical Knowledge is taught and understood as linear from diagnosis to symptoms and/or signs. However, during medical diagnosis the clinical thought pattern is backwards and flows from symptoms and/or signs to diagnosis. This transition is accounted for by using Bayes' Theorem.

Assumptions required for application of Bayes' Theorem as applied within the Automate Analyzer—The flow from diagnosis to symptoms/signs in acquisition of medical knowledge is dependent on primarily pathophysiology. The pathophysiology data obtained from the medical knowledge base (literature) can be extrapolated to the current population. Since symptoms/signs and diagnosis are binary attributes, the concept does not account for fuzzy logic, severity, time, location, or uncertainty. Incomplete penetrance is the norm for some attributes. Further the concept as described of 1 Dx (diagnosis)→1 Si/Sx (Sign/Symptom) assumes the Dx is within medical knowledge base.

Bayes' Probability as applied within the Automated Analyzer—Similar to the Odds Method the goal is to objectify initial subjective data to produce a result that may yield a significantly different outcome to aid clinical decision making (hereby reference to Lu, Ying. Advanced medical statistics. River Edge, N.J. [u.a.]: World Scientific, 2003, is now incorporated for mathematical and statistical details). As an example, Posterior Probability=equals Total (prior) Probability multiplied by the Conditional Probability divided by a normalizing constant. Further, the Total Probability accounts for a population having a Dx regardless of Si/Sx. The Conditional Probability accounts for the medical knowledge concept described previously (Dx→Si/Sx). Where the Normalizing Constant accounts for objective data obtained from prior validation studies on the given Dx→Si/Sx. And where the Posterior Probability (or probability of disease given the Si/Sx) equals P(pos Dx|Si)=Si→Dx Posterior Probability=Prior Probability×LR/Evidence.

If LR/Evidence~LR*→then the following is true:

Posterior Probability=Prior Probability×LR*→then continue updating with each new data point to yield new LR*

Additional Assumptions for Bayes' Thereon as applied with the Automated Analyzer—Independence of attributes referring to mutually exclusive, where:

1Si→1Dx not 1Si→2 differ Dx

In the later example, it is required to combine the two different diagnoses; otherwise Bayes' will not function. In addition, the medical knowledge base is required to be exhaustive, with little to no omissions. Further, the following data must exist: validation data for the given diagnosis, the probability or odds of each Si/Sx for the given diagnosis, and the total probability if not starting from time equal to zero.

Bayes' Probability and Constant Adjustment as applied within the Automated Analyzer—Both total and conditional probabilities are in constantly under adjustment as older cases become irrelevant to the current population. The current population is accounted for in the new set of objective data within the medical knowledge base.

Bayes' versus Scoring as applied within the Automated Analyzer—Both are methods are binary, if not using Likard Scale (refer to a standard statistical text for mathematical details). The primary difference is that Bayes' has a prior probability component taking into account the clinical "feeling" or professional experience prior to factoring in objective data. Example scoring methods are as described previously.

Bayes' versus Logic Tree Branching (or algorithm) as applied within the Automated Analyzer—Logic Tree Branching is very similar when looked at as a series of individual decisions. The primary difference is that Logic Tree Branching does not have a prior (pre-test) probability component. Examples of Logic Tree Branching are as described previously.

Conditional Independence as applied within the Automated Analyzer—When the assumption that the probability of observing the conjunction of attributes is equal to the product of the individual probabilities is made, the attributes can be described as having no relationship to each other, as previously described.

Linear Regression as applied within the Automated Analyzer—The method attempts to model the relationship between two variables by fitting a linear equation to observed data. One variable is an explanatory variable and the other is a dependent variable. Before attempting to fit a linear model to observed data, a determination is made regarding is presence of a relationship between the variables of interest. The relationship does not imply a causative relationship, only a significant association between the two variables (refer to a standard statistical text for mathematical details).

Logistic Regression or Regression Analysis as applied within the Automated Analyzer—The goal is to find a subset of all the explanatory variables that can be combined to predict the value of the outcome variable. The outcome is a regression equation having the outcome variable on the left hand side and a combination of the explanatory variables on the right. For any future patient, the values of their explanatory variables can be fed into the equation to predict the value of their outcome variable. Further, logistic regression is a variation of ordinary regression which is used when the dependent (or response) variable is a dichotomous variable (requires only two values, which usually represent the occurrence or non-occurrence of some outcome event, usually coded as 0 or 1) and the independent (input) variables are continuous, categorical, or both (refer to a standard statistical text for mathematical details).

Comparison between Bayes' and Logistic Regression as applied within the Automated Analyzer—Bayes' converges in O (log(n)) cycles, but the asymptomatic error is greater than Logistic Regression. Logistic regression converges in O(n) updates. Comparing both algorithms, the differentiating feature is that for a smaller number of examples Bayes' performs better, but for large number of examples Logistic Regression performs better (refer to a standard statistical text for mathematical details).

Least-Squares Regression as applied within the Automated Analyzer—A method for fitting a regression line is the method of least-squares where minimizing the sum of the squares of the vertical deviations from each data point to the line is calculated. Because the deviations are first squared, then summed, there are no cancellations between positive and negative values. The measures of correlation infer the same thing as measures in the study of regression (refer to a standard statistical text for mathematical details).

Solving the regression equation as applied within the Automated Analyzer—The general regression equation can be written as y=a+b x. In order to predict a variable, the mean, variance, and standard deviation of the values of x and y need to be found. Mean is defined as the average value calculated by taking the sum of all values and dividing by the total number of values. Variance is defined as the sum of squares of deviations from the mean, divided by the N. Standard Deviation is defined as the square root of the average of the squared deviation(s) from the mean. Related concepts such as outliers, residuals, lurking variables, and avoidance of extrapolation, can also be employed (refer to a standard statistical text for mathematical details).

Order entry support as applied within the Automated Analyzer—If the automated analyzer is directed and set to extract meaning from previously described decoded reports and corresponding column categories (as examples, see following a to f) then the said described analysis can be utilized to serve as appropriateness criteria before an imaging order is requested 200 (refer to FIG. 3). The said method allows additional decision making support at the time of imaging order request 200:

a. Demographics (DEMO)

b. V/S—example of automated BP analysis c. Si/Sx—example of a variety of pain locations, and signs such as unequal BP in the upper extremities with automated analysis from the EMR.

d. PMH—examples of automated analysis on medical syndromes such as Marfan's and Ehler Danlos, as well as a variety of surgical aortic repairs and valve repairs.

e. EKG—example of automated analysis of associated EKGs. This also demonstrates the NLP/decoder can be run on non-imaging tests to extract meaning
f. CXR—Another example of NLP/decoder run on a different radiology examination.
g. Surgical reports and notes Decision support at the time of report creation—If the automated analyzer is directed and set to extract meaning from previously described decoded reports and corresponding column categories with application of dynamic report decoding and subsequent analytics prior to imaging report sign-off, said analyzer will serve as real time decision making support for reading radiologist (and to assist in proper reporting for billing purposes) in the context of a primary finding, alternative finding, and/or critical finding.

Decision support at the time of report creation—If the automated analyzer is directed and set to extract meaning from previously described decoded reports and corresponding column categories with application of dynamic report decoding and subsequent analytics prior to imaging report sign-off, said analyzer will serve as real time decision making support for reading radiologist (and to assist in proper reporting for billing purposes) in the context of potential or possible textual errors.

Decision support at the time of report creation—If the automated analyzer is directed and set to extract meaning from previously described decoded reports and corresponding column categories with application of dynamic report decoding and subsequent analytics prior to imaging report sign-off, said analyzer will serve as real time decision making support for reading radiologist (and to assist in proper reporting for billing purposes) in the context of suggested report structure according to a pre-determined database.

In general, any goal can divided into component parts and processed using Stages 1-4:
GOAL: any area of concern can be searched (KPI) (STAGE 1)
RESTRUCTURE AND PARSE DATA (STAGE 2)
RUN NLP ENGINE TO DECODE DATA (STAGE 3)
APPLY AUTOMATED ANALYZER (STAGE 4)
CHANGE PROCESS: based on results from automated analyzer
REDO GOAL SEARCH: same area of concern can be searched again (KPI) (STAGE 1)
RESTRUCTURE AND PARSE DATA (STAGE 2)
RUN NLP ENGINE TO DECODE DATA (STAGE 3)
APPLY AUTOMATED ANALYZER (STAGE 4): are results improved from after process change?

It is to be understood, of course, that while the exemplary methods detailed above are performed manually, the methods themselves can be performed in a more automated fashion by writing a simple script or other piece of code. Thus the methods can be combined into a single broad software application thereby achieving natural language understanding and auto analytics.

And, it is to be understood, of course, that all of the above methods may be validated using improved reference standards as they become available from improved verified diagnostics in imaging, pathology, or laboratory analysis hereby allowing production of contingency tables (as an example, a process for validation of each imaging protocol).

In the foregoing description, the method and apparatus of the present invention have been described with reference to specific examples. It is to be understood and expected that variations in the principles of the method and apparatus herein disclosed may be made by one skilled in the art and it is intended that such modifications, changes, and substitutions are to be included within the scope of the present invention as set forth in the appended claims. The specification and the drawings are accordingly to be regarded in an illustrative rather than in a restrictive sense.

What is claimed is:

1. A computer implemented method for the display of radiology, clinical, pathology, and laboratory reports as a single comprehensive medical report on a non-transitory computer-readable medium in a text, graphical or tabular format to assist in a proper diagnosis of a patient, the method comprising executing on a processor the steps of:

optimizing a keyword search within a keyword searchable database of text data representing the radiology, clinical, pathology, and laboratory reports;

restructuring and parsing the text data in the database to create spreadsheets corresponding to specific patient information taken from the radiology, clinical, pathology, and laboratory reports, wherein this step further comprises executing on a further processor the steps of:

using a find/replace function to delete tabs, paragraphs, and colons in text;

rebuilding paragraphs, or text data (or alphanumeric string), corresponding to specific patient information taken from the radiology, clinical, pathology, and laboratory reports, to create rows within a spreadsheet;

reprocessing the same string of text data (or alphanumeric string) to create delimiters as placeholders for parsing the data into separate cells on the same row, each cell corresponding to one of the radiology, clinical, pathology, and laboratory reports;

uploading and importing the rebuilt and processed text data (or alphanumeric string) into a spreadsheet application;

directing the spreadsheet application to select the appropriate delimiters and text style;

directing the spreadsheet application to select the appropriate pre-defined alphanumeric strings and text style;

directing the spreadsheet application to batch replace pre-defined alphanumeric strings to allow standardization of report format;

dynamically restructuring and parsing reports into text data (or alphanumeric string) (or alphanumeric strings) within cells across columns whereby the source text data (or alphanumeric string) is matched to a given row and the column content is matched as described by the column headings;

dynamically enabling the "shrink to fit" feature and applying said feature to the text data (or alphanumeric string) (or alphanumeric strings) within a spreadsheet or database;

dynamically using the "shrink to fit" feature when enabled as applied to text data (or alphanumeric string) (or alphanumeric string(s)) to analyze a spreadsheet or database efficiently;

dynamically enabling the "fill color" feature, or background cell color, and applying said feature to all cells, and specifically only those cells, containing text data (or alphanumeric string) (or alphanumeric strings) within a spreadsheet or database;

identifying cells within a spreadsheet or database by color coding to enable downstream processing or visual programming;

associating cells containing text data (or alphanumeric string) (or alphanumeric strings) using said color coding;

assigning a given background cell color to identify or classify the text data (or alphanumeric string) (or alphanumeric string(s)) contained within said cell;

assigning a given background color to identify or classify the absence of text data (or alphanumeric string) (or alphanumeric string(s)) contained within cell;

dynamically comparing the background color of a cell to another cell to generate or derive knowledge or understanding;

matching of text data (or alphanumeric string) (or alphanumeric string(s)) contained within a cell, row, and/or column to a descriptive header term within a spreadsheet or database;

classifying of text data (or alphanumeric string) (or alphanumeric string(s)) contained within a cell, row, and/or column to a descriptive header term within a spreadsheet or database;

removing of any protected health information from said database in situations where de-identified patient data is required; and, dynamically applying the said methods to successive cells, rows, and/or columns of text data (or alphanumeric string(s)) in a spreadsheet or database;

creating and applying a natural language processing engine to the database of spreadsheets for identification and translation of medical terminology contained in the spreadsheets; and applying a comprehensive automated analyzer to the natural language processed database of spreadsheets to identify and collate related medical information, wherein a result from the automated analyzer can then be viewed as the single comprehensive medical report in the text, graphical or tabular format on one of a computer or hand-held device to assist in a proper diagnosis of the patient.

2. The method according to claim 1, wherein the step of optimizing a keyword search within the keyword searchable database further comprises the step of:

using bootstrapping and jackknifing techniques on at least one of:

a radiologist (physician) verified and confirmed reference standard to validate keyword search criteria for each imaging protocol;

a pathologist (physician) verified and confirmed reference standard to validate keyword search criteria for each diagnostic protocol;

a clinician (physician) verified and confirmed reference standard to validate keyword search criteria for each diagnosis; and, a clinician (physician) verified and confirmed reference standard to validate keyword or key-number search criteria for each laboratory protocol and parameter.

3. The method according to claim 1, wherein the step of optimizing a keyword search within the keyword searchable database further comprises the steps of:

improving the accuracy of the search results by using optimized boolean and power search techniques for queries based on at least one of:
the imaging protocol in question;
the diagnostic protocol in question;
the diagnosis in question;
the laboratory protocol or laboratory parameter in question; and repeatedly applying the search techniques to continuously improve the accuracy of the keyword search criteria to further optimize results in an effort to retrieve all records with true hits (relevant hits) while minimizing retrieval of false hits based on confounding variables.

4. The method according to claim 1, wherein the step of optimizing a keyword search within the keyword searchable database further comprises the step of uploading the optimized results (records or reports) to a server for further processing.

5. A computer implemented method for the display of radiology, clinical, pathology, and laboratory reports as a single comprehensive medical report in a text, graphical or tabular format on a non-transitory computer-readable medium to assist in a proper diagnosis of a patient, the method comprising executing on a processor the steps of:

optimizing a keyword search within a keyword searchable database of text data representing the radiology, clinical, pathology, and laboratory reports;

restructuring and parsing the text data in the database into spreadsheets wherein the rows, columns and cells represent specific patient information taken from the radiology, clinical, pathology, and laboratory reports;

creating and applying a natural language processing engine to the database of spreadsheets of specific patient information for identification and translation of medical terminology, wherein this step further comprises executing on a further processor the steps of:

uploading a generic batch find/replace application capable of executing such task on at least one of a text file, digital document, spreadsheet, and database;

applying said generic batch find/replace application to a text data (or alphanumeric string) (or alphanumeric string(s)) database;

generating key text phrases, text data (or alphanumeric string) (or alphanumeric string(s)) verified as valid by a qualified professional representative to serve as a basis of a decoder table;

matching the key text phrases or text data (or alphanumeric string), with or without the use of single or multi-character wildcards, to generate a decode table, decode columns, translation table, or translation columns;

identifying numerical values as how far away, in single character increments within an alphanumeric string in a cell, the identified value is from a keyword (or positive AAD) to denote a level of confidence in the identified value being associated with said keyword; and, dynamically generating similar text phrases (or alphanumeric string(s)) in a repetitive manner using one of a manual input and function (formula) derivation; and, applying a comprehensive automated analyzer to the natural language processed database of spreadsheets of the patient information taken from the radiology, clinical, pathology, and laboratory reports to identify and collate related medical information, wherein a result from the automated analyzer can then be viewed as a single comprehensive medical report in the text, graphical or tabular format on one of a computer or hand-held device to assist in a proper diagnosis of the patient.

6. The method according to claim 5, further comprising at least one of the steps of:

analyzing the dynamically generated text phrases, manually or artificially derived, by a qualified professional representative to serve as the basis of a decoder table; and analyzing the dynamically generated text phrases, manually or artificially derived, by a qualified professional representative to ensure accuracy of the decoder table or translation table.

7. The method according to claim 6, further comprising the steps of:
generating at least one of a secondary color coding, a cell fill color, a background fill color, a text font or a style change to key text phrases (text data (or alphanumeric string) or alphanumeric string(s)) to serve as the basis of a decoder table;
matching the at least one secondary color coding, cell fill color, background fill color, text font or style changes to the key text phrases to generate at least one of a decode table, decode columns, translation table, or translation columns; and,
dynamically generating at least one of a similar secondary color coding, cell fill color, background fill color, text font or style change to key text phrases in a repetitive manner using at least one of manual input or function (formula) derivation.

8. The method according to claim 7, further comprising the steps of:
analyzing such dynamically generated secondary color coding, or cell fill color, or background fill color, and/or text font or style changes to key text phrases, manually or artificially derived, by a qualified professional representative to serve as the basis of a decoder table; and,
analyzing such dynamically generated secondary color coding, or cell fill color, or background fill color, and/or text font or style changes to key text phrases, manually or artificially derived, by a qualified professional representative to ensure accuracy of the decoder table or translation table.

9. The method according to claim 8, further comprising the steps of:
dynamically applying each of the previous steps in an iterative fashion using at least one of:
a different decode or translation alphanumeric string used at each step; and
a binary decision making step before execution of the next step (if cell A is decoded as positive then proceed to application of decode table B to the adjacent cell),
wherein the successive steps of both text data (or alphanumeric string) decoding and application of secondary color coding provides a level of natural language understanding, Quality Assurance, validation, and verification; and,
dynamically changing the algorithm that decides which decoding step occurs in succession relative to the answer or result from the previous decoding step.

10. The method according to claim 9, further comprising the steps of:
dynamically decoding reports (or alphanumeric string(s)) for proper or complete performance, or performance as designed, of a diagnostic protocol based on a given reference;
identifying decoded diagnostic reports as correctly performed or incorrectly performed as designed;
classifying decoded diagnostic reports as correctly performed or incorrectly performed as designed; and,
reclassifying incorrectly performed diagnostic reports to a correct classification.

11. The method according to claim 10, further comprising the step of:
dynamically decoding diagnostic reports, or other reports, as positive, negative, or indeterminate for a diagnosis or disease.

12. The method according to claim 10, further comprising the step of:
dynamically decoding diagnostic reports, or other reports, as positive, negative, or indeterminate, based on a calculated mean or statistical numerical average of a given number of similarly decoded cells for a single report, for a diagnosis or disease.

13. The method according to claim 10, further comprising the step of:
dynamically decoding diagnostic reports, or other reports, as according to known subtypes (subcategories or subclasses, both mutually exclusive and/or non-mutually exclusive) for a diagnosis or disease.

14. The method according to claim 10, further comprising at least one of the steps of:
dynamically decoding diagnostic reports, or other reports, as according to known subtypes (subcategories or subclasses, both mutually exclusive and/or non-mutually exclusive) for a diagnosis or disease:
based on a calculated mean or statistical numerical average of a given number of similarly decoded cells for a single report; or
by assigning secondary color coding as generated by superimposed NLP (or automated understanding);
dynamically decoding diagnostic reports, or other reports, as according to known subtypes (subcategories or subclasses, both mutually exclusive and/or non-mutually exclusive) based on a calculated mean or statistical numerical average of a given number of similarly decoded cells for a single report, for a diagnosis or disease, by assigning secondary color coding as generated by superimposed NLP (or automated understanding);
dynamically decoding diagnostic reports, or other reports, as according to known subtypes (subcategories or subclasses, both mutually exclusive and/or non-mutually exclusive) for a diagnosis (or alternative diagnosis), disease, or finding within a single cell (or examination) by assigning secondary color coding as generated by superimposed NLP (or automated understanding), thereby representing a variably described single finding versus variably described additional finding(s), the dominant finding (or finding with the greatest number of decoded hits) can be represented by said secondary color coding;
dynamically decoding diagnostic reports, or other reports, as according to known subtypes (subcategories or subclasses, both mutually exclusive and/or non-mutually exclusive) for a diagnosis (or alternative diagnosis), disease, or finding within a single cell (or examination) based on a calculated mean or statistical numerical average of a given number of similarly decoded cells for a single report, thereby representing a variably described single finding versus variably described additional finding(s), the dominant finding (or finding with the greatest number of decoded hits);
dynamically decoding diagnostic reports, or other reports, as according to known subtypes (subcategories or subclasses, both mutually exclusive and/or non-mutually exclusive) for a diagnosis (or alternative diagnosis), disease, or finding within a single cell (or examination) by assigning a different secondary color coding as generated by superimposed NLP (or automated understanding), thereby representing a variably described absence/lack of a single finding versus variably described absence/lack of an additional finding(s), the dominant finding, or lack thereof (or finding with the greatest number of decoded negative hits) can be represented by said secondary color coding;

dynamically decoding diagnostic reports, or other reports, as according to known subtypes (subcategories or subclasses, both mutually exclusive and/or non-mutually exclusive)) for a diagnosis (or alternative diagnosis), disease, or finding within a single cell (or examination) based on a calculated mean or statistical numerical average of a given number of similarly decoded cells for a single report, thereby representing a variably described absence/lack of a single finding versus variably described absence/lack of an additional finding(s), the dominant finding, or lack thereof (or finding with the greatest number of decoded negative hits);

dynamically decoding diagnostic reports, or other reports, as according to known subtypes (subcategories or subclasses, both mutually exclusive and/or non-mutually exclusive) for a diagnosis (or alternative diagnosis), disease, or finding within a single cell (or examination) by assigning a different secondary color coding as generated by superimposed NLP (or automated understanding), thereby representing a variably described stability (versus absence/lack) of a single finding versus variably described stability (versus absence/lack) of an additional finding(s), the dominant finding, or lack thereof (or finding with the greatest number of decoded negative hits) can be represented by said secondary color coding;

dynamically decoding diagnostic reports, or other reports, as according to known subtypes (subcategories or subclasses, both mutually exclusive and/or non-mutually exclusive) for a diagnosis (or alternative diagnosis), disease, or finding within a single cell (or examination) based on a calculated mean or statistical numerical average of a given number of similarly decoded cells for a single report, thereby representing a variably described stability (versus absence/lack) of a single finding versus variably described stability (versus absence/lack) of an additional finding(s), the dominant finding, or lack thereof (or finding with the greatest number of decoded negative hits);

dynamically decoding diagnostic reports, or other reports, as according to known subtypes (subcategories or subclasses, both mutually exclusive and/or non-mutually exclusive) for a diagnosis (or alternative diagnosis), disease, finding, finding location (location within the human body), within a single cell (or examination) based on an identified numerical value (measurement or described alphanumerical size) by assigning either a predefined category (value, classification, absence or presence of disease, or other alphanumerical string) or different secondary color coding as generated by superimposed NLP (or automated understanding), thereby representing a variably described presence or stability (versus absence/lack) of a single finding versus variably described presence or stability (versus absence/lack) of an additional finding(s), the dominant finding, or lack thereof (or finding with the greatest number of decoded positive or negative hits) can be represented by an assigned category (as example, value identified meets definition of aneurysmal size) or a secondary color coding;

dynamically decoding diagnostic reports, or other reports, as according to known subtypes (subcategories or subclasses, both mutually exclusive and/or non-mutually exclusive) for a diagnosis (or alternative diagnosis), disease, finding, or finding location (location within the human body) within a single cell (or examination) according to a calculated mean or statistical numerical average of a given number of similarly decoded cells for a single report, based on an identified numerical value (measurement or described alphanumerical size) by assigning either a predefined category (value, classification, absence or presence of disease, or other alphanumerical string) or different secondary color coding as generated by superimposed NLP (or automated understanding), thereby representing a variably described presence or stability (versus absence/lack) of a single finding versus variably described presence or stability (versus absence/lack) of an additional finding(s), the dominant finding, or lack thereof (or finding with the greatest number of decoded positive or negative hits) can be represented by an assigned category (as example, value identified meets definition of aneurysmal size) or a secondary color coding;

dynamically applying above said secondary color coding to the concept of NLP engine decoding yields thereby allowing efficient human processing or visual programming; and, dynamically applying at least one of the previous steps to successive cells, rows, and/or columns of text data (or alphanumeric string) (or alphanumeric string(s)) in a spreadsheet or database.

* * * * *